US006634576B2

(12) United States Patent
Verhoff et al.

(10) Patent No.: US 6,634,576 B2
(45) Date of Patent: Oct. 21, 2003

(54) MILLED PARTICLES

(75) Inventors: Frank Verhoff, Cincinnati, OH (US); Gary W. Pace, Winchester, MA (US); Robert A. Snow, West Chester, PA (US); Fay Millar, Ladson, SC (US)

(73) Assignee: RTP Pharma Inc., Durham, NC (US)

( * ) Notice: Subject to any disclaimer, the term of this patent is extended or adjusted under 35 U.S.C. 154(b) by 72 days.

(21) Appl. No.: 09/940,864

(22) Filed: Aug. 29, 2001

(65) Prior Publication Data

US 2002/0047058 A1 Apr. 25, 2002

Related U.S. Application Data

(60) Provisional application No. 60/229,042, filed on Aug. 31, 2000.

(51) Int. Cl.$^7$ .............................................. B02C 12/14
(52) U.S. Cl. ........................................ 241/21; 241/184
(58) Field of Search ........................ 241/21, 184, 171, 241/172, 23, 24.12

(56) References Cited

U.S. PATENT DOCUMENTS

| | | | |
|---|---|---|---|
| 2,803,582 A | 8/1957 | Cherney | |
| 3,137,631 A | 6/1964 | Soloway | |
| 3,216,897 A | 11/1965 | Krantz | |
| 3,274,063 A | 9/1966 | Nieper et al. | |
| 3,521,825 A | 7/1970 | Morcom | |
| 3,594,476 A | 7/1971 | Merrill | |
| 3,715,432 A | 2/1973 | Merrill | |
| 3,755,557 A | 8/1973 | Jacobs | |
| 3,794,476 A | 2/1974 | Michalik et al. | |
| 3,937,668 A | 2/1976 | Zolle | |
| 3,960,757 A | 6/1976 | Morishita et al. | |
| 3,965,255 A | 6/1976 | Bloch et al. | |
| 3,995,817 A | 12/1976 | Brociner | |
| 3,998,753 A | 12/1976 | Antoshkiw et al. | |
| 4,006,025 A | 2/1977 | Swank et al. | |
| 4,016,100 A | 4/1977 | Suzuki et al. | |
| 4,053,585 A | 10/1977 | Allison et al. | |
| 4,056,635 A | 11/1977 | Glen et al. | |
| 4,073,943 A | 2/1978 | Wretlind et al. | |
| 4,078,052 A | 3/1978 | Papahadjopoulos | |
| 4,089,801 A | 5/1978 | Schneider | |
| 4,102,806 A | 7/1978 | Kondo et al. | |
| 4,107,288 A | 8/1978 | Oppenheim et al. | |
| 4,133,874 A | 1/1979 | Miller et al. | |
| 4,145,410 A | 3/1979 | Sears | |
| 4,147,767 A | 4/1979 | Yapel, Jr. | |
| 4,186,183 A | 1/1980 | Steck et al. | |
| 4,219,548 A | 8/1980 | Reller | |
| 4,235,871 A | 11/1980 | Papahadjopoulos et al. | |
| 4,241,046 A | 12/1980 | Papahadjopoulos et al. | |
| 4,271,196 A | 6/1981 | Schmidt | |
| 4,294,916 A | 10/1981 | Postle et al. | |
| 4,294,917 A | 10/1981 | Postle et al. | |
| 4,297,744 A | 10/1981 | Hoffmann et al. | |
| 4,298,594 A | 11/1981 | Sears et al. | |
| 4,302,459 A | 11/1981 | Steck et al. | |
| 4,308,166 A | 12/1981 | Marchetti et al. | |
| 4,309,421 A | 1/1982 | Ghyczy et al. | |
| 4,316,884 A | 2/1982 | Alam et al. | |

(List continued on next page.)

FOREIGN PATENT DOCUMENTS

| | | |
|---|---|---|
| DE | 1291607 B | 3/1969 |
| DE | 2 513 797 | 10/1975 |
| DE | 2 938 807 | 11/1980 |
| DE | 3837412 A1 | 11/1988 |
| EP | 0 600 528 A | 11/1980 |
| EP | 0 052 322 | 5/1982 |
| EP | 0 129 893 A | 1/1985 |
| EP | 0 272 091 | 6/1988 |

(List continued on next page.)

OTHER PUBLICATIONS

"Derived Diameters and Distribution Statistics," from an unknown web–site, 6 pages.
"Getting Started", Man 0106, Issue 1.0, (Jan. 1996), *Malvern Instruments Ltd.*, England, pp. 7.1–7.7.
Bangham et al., "Diffusion of Univalent Ions Across the Lamellae of Swollen Phospholipids", *J. Mol. Biol.* (1965) 13, pp. 238–252.

(List continued on next page.)

*Primary Examiner*—Mark Rosenbaum
(74) *Attorney, Agent, or Firm*—Edwards & Angell, LLP

(57) ABSTRACT

A process for milling a solid substrate in the milling chamber of a dispersion or media mill in the presence of a two or more compositions of milling media bodies is disclosed wherein all milling media bodies contribute to the grinding of the solid substrate and wherein at least one composition of media bodies provides fragments of milling media bodies that are retained with the milled solid substrate particles in the form of a synergetic commixture produced in the milling process. More specifically, a process is disclosed for preparing a synergetic commixture comprising small particles of a solid substrate and small particulates of a first material of a desired size comprising the steps of (a) providing to the milling chamber of a media mill a contents comprising a pre-mix of a solid substrate, a fluid carrier, a plurality of milling bodies of a first material having a fracture toughness $K_{c1}$, and a plurality of milling bodies of a second material having a fracture toughness $K_{c2}$; (b) operating the media mill to grind the solid substrate and degrade at least a portion of the milling bodies of first material to produce a dispersion in the fluid carrier comprising a synergetic commixture of small particulates of the first material and small particles of the solid substrate having a desired size equal to or less than a size Sp; (c) separating the dispersion from any milling bodies and solid substrate particles having a size larger than $S_p$; and (d) optionally removing the fluid carrier from the dispersion to form a synergetic commixture free of fluid and comprising the particles and the small particulates, wherein $K_{C2}$ is greater than $K_{C1}$.

47 Claims, No Drawings

U.S. PATENT DOCUMENTS

| | | |
|---|---|---|
| 4,320,121 A | 3/1982 | Sears |
| 4,325,871 A | 4/1982 | Sasaki et al. |
| 4,328,222 A | 5/1982 | Schmidt |
| 4,329,332 A | 5/1982 | Couvreur et al. |
| 4,331,654 A | 5/1982 | Morris |
| 4,332,795 A | 6/1982 | Ghyczy et al. |
| 4,332,796 A | 6/1982 | Los |
| 4,340,594 A | 7/1982 | Mizushima et al. |
| 4,345,588 A | 8/1982 | Widder et al. |
| 4,351,831 A | 9/1982 | Growdon et al. |
| 4,356,167 A | 10/1982 | Kelly |
| 4,369,182 A | 1/1983 | Ghyczy et al. |
| 4,378,354 A | 3/1983 | Ghyczy et al. |
| 4,394,372 A | 7/1983 | Taylor |
| 4,397,846 A | 8/1983 | Weiner et al. |
| 4,411,894 A | 10/1983 | Schrank et al. |
| 4,421,747 A | 12/1983 | Ghyczy et al. |
| 4,427,649 A | 1/1984 | Dingle et al. |
| 4,448,765 A | 5/1984 | Ash et al. |
| 4,454,152 A | 6/1984 | Barry et al. |
| 4,483,847 A | 11/1984 | Augart |
| 4,485,054 A | 11/1984 | Mezei et al. |
| 4,489,055 A | 12/1984 | Couvreur et al. |
| 4,492,720 A | 1/1985 | Mosier |
| 4,515,736 A | 5/1985 | Deamer |
| 4,522,743 A | 6/1985 | Horn et al. |
| 4,529,561 A | 7/1985 | Hunt et al. |
| 4,532,089 A | 7/1985 | MacDonald |
| 4,540,602 A | 9/1985 | Motoyama et al. |
| 4,610,868 A | 9/1986 | Fountain et al. |
| 4,613,505 A | 9/1986 | Mizushima et al. |
| 4,622,219 A | 11/1986 | Haynes |
| 4,623,364 A | 11/1986 | Cottringer et al. |
| 4,624,418 A | 11/1986 | Szkaradek |
| 4,675,236 A | 6/1987 | Ohkawara et al. |
| 4,687,762 A | 8/1987 | Fukushima et al. |
| 4,717,565 A | 1/1988 | Denick, Jr. |
| 4,725,442 A | 2/1988 | Haynes |
| 4,756,910 A | 7/1988 | Yagi et al. |
| 4,761,288 A | 8/1988 | Mezei |
| 4,762,720 A | 8/1988 | Jizomoto |
| 4,766,046 A | 8/1988 | Abra et al. |
| 4,772,627 A | 9/1988 | Matsui et al. |
| 4,775,393 A | 10/1988 | Boecker et al. |
| 4,776,991 A | 10/1988 | Farmer et al. |
| 4,783,484 A | 11/1988 | Violante et al. |
| 4,801,455 A | 1/1989 | List et al. |
| 4,803,070 A | 2/1989 | Cantrell et al. |
| 4,806,350 A | 2/1989 | Gerber |
| 4,806,352 A | 2/1989 | Cantrell |
| 4,826,687 A | 5/1989 | Nerome et al. |
| 4,826,689 A | 5/1989 | Violanto et al. |
| 4,839,111 A | 6/1989 | Huang |
| 4,849,210 A | 7/1989 | Widder |
| 4,851,421 A | 7/1989 | Iwasaki et al. |
| 4,880,634 A | 11/1989 | Speiser |
| 4,927,744 A | 5/1990 | Henzel et al. |
| 4,940,654 A | 7/1990 | Diehl et al. |
| 4,945,121 A | 7/1990 | Micale et al. |
| 4,950,586 A | 8/1990 | Diehl et al. |
| 4,968,435 A | 11/1990 | Neff et al. |
| 4,973,465 A | 11/1990 | Baurain et al. |
| 4,989,794 A | 2/1991 | Askew et al. |
| 5,022,592 A | 6/1991 | Zakheim et al. |
| 5,030,453 A | 7/1991 | Lenk et al. |
| 5,076,507 A | 12/1991 | Graf |
| 5,083,712 A | 1/1992 | Askew et al. |
| 5,091,187 A | 2/1992 | Haynes |
| 5,091,188 A | 2/1992 | Haynes |
| 5,092,711 A | 3/1992 | Langner |
| 5,100,591 A | 3/1992 | Leclef et al. |
| 5,139,719 A | 8/1992 | Winder |
| 5,145,684 A | 9/1992 | Liversidge et al. |
| 5,246,707 A | 9/1993 | Haynes |
| 5,257,742 A | 11/1993 | Yashima et al. |
| 5,272,137 A | 12/1993 | Blase et al. |
| 5,302,401 A | 4/1994 | Liversidge et al. |
| 5,318,767 A | 6/1994 | Liversidge et al. |
| 5,320,906 A | 6/1994 | Eley et al. |
| 5,336,507 A | 8/1994 | Na et al. |
| 5,383,945 A | 1/1995 | Cottringer et al. |
| 5,470,583 A | 11/1995 | Na et al. |
| 5,478,705 A | 12/1995 | Czekai et al. |
| 5,500,331 A | 3/1996 | Czekai et al. |
| 5,513,803 A * | 5/1996 | Czekai et al. .................. 241/16 |
| 5,518,187 A | 5/1996 | Bruno et al. |
| 5,534,270 A | 7/1996 | De Castro |
| RE35,338 E | 9/1996 | Haynes |
| 5,552,160 A | 9/1996 | Liversidge et al. |
| 5,560,931 A | 10/1996 | Eickhoff et al. |
| 5,565,188 A | 10/1996 | Wong et al. |
| 5,585,108 A | 12/1996 | Ruddy et al. |
| 5,611,829 A | 3/1997 | Monroe et al. |
| 5,637,625 A | 6/1997 | Haynes |
| 5,657,931 A | 8/1997 | Nair et al. |
| 5,662,279 A | 9/1997 | Czekai et al. |
| 5,674,616 A | 10/1997 | Balcar |
| 5,679,138 A | 10/1997 | Bishop et al. |
| 5,700,471 A | 12/1997 | End et al. |
| 5,704,556 A | 1/1998 | Mc Laughlin |
| 5,718,388 A | 2/1998 | Czekai et al. |
| 5,718,919 A | 2/1998 | Ruddy et al. |
| 5,736,121 A | 4/1998 | Unger |
| 5,747,001 A | 5/1998 | Wiedmann et al. |
| 5,834,025 A | 11/1998 | de Garavilla et al. |
| 5,858,410 A | 1/1999 | Muller et al. |
| 5,862,999 A | 1/1999 | Czekai et al. |
| 5,902,711 A | 5/1999 | Smith et al. |
| 5,922,355 A | 7/1999 | Parikh et al. |
| 2002/0003179 A1 | 1/2002 | Verhoff et al. |
| 2002/0012704 A1 | 1/2002 | Pace et al. |

FOREIGN PATENT DOCUMENTS

| | | |
|---|---|---|
| EP | 0 153 926 | 2/1991 |
| EP | 0 418 153 | 3/1991 |
| EP | 0 533 690 | 10/1991 |
| EP | 0 498 482 | 8/1992 |
| EP | 0 499 299 | 8/1992 |
| EP | 0 456 764 | 9/1993 |
| EP | 0 456 670 | 11/1993 |
| GB | 1570362 | 3/1977 |
| GB | 2046094 | 11/1980 |
| JP | 56167616 | 5/1980 |
| JP | 1502590 | 11/1980 |
| JP | 55141407 | 11/1980 |
| JP | 60208910 | 11/1980 |
| JP | 63233915 | 10/1985 |
| WO | WO 8500011 | 1/1985 |
| WO | WO 8704592 | 8/1987 |
| WO | WO 88/04924 | 7/1988 |
| WO | WO 9104011 | 4/1991 |
| WO | WO 9116068 | 10/1991 |
| WO | WO 9502394 A | 1/1995 |
| WO | WO 9714407 | 4/1997 |
| WO | WO 9939700 | 8/1999 |
| WO | WO 0180828 | 11/2001 |
| WO | WO 0185345 A | 11/2001 |

OTHER PUBLICATIONS

Bamzai et al., "Investigations on Indentation Induces Hardness and Fracture Mechanism in Flux Grown DyAlO$_3$ Crystals", *Appl Surf Sci*, 133 [3], 1998, Abstract.

Becker et al., "Comminution of Ceramics in Stirred Media Mills and Wear of Grinding Beads", *Powder Technology* 105 (1999), p. 374 (Abstract).

Benz et al., "Electrical Capacity of Black Lipid Films and of Lipid Bilayers Made from Monolayers", *Biochem. Biophys. Acta*, (1975) vol. 394, pp. 323–334.

Bergmann, Ludwig, *Der Ultraschall*, 5 Aufl., (1949), Stuttgart, S. 551–564, 672f.

Bernhardt et al., "Influence of Suspension: Properties on Ultra–Fine Grinding in Stirred Ball Mills", *Powder Technology* 105 (1999), p. 357 (Abstract).

Bittman, Robert, "Sterol–Polyene Antibiotic Complexation: Probe of Membrane Structure," *Lipids*, vol. 13, No. 10, pp. 686–691 (1978).

Boccaccini, Aldo R., "The Relationship Between Wear Behavior and Brittleness Index in Engineering Ceramics and Dispersion–Reinforced Ceramic Composites", *Interceram*, 48 [3], 1999. Abstract.

Buchmuller et al., "Cryopel:Ein neus Verfahren zum Pelletieren und Frosten Biologischer Substrate," *Gas Aktuell*, 35, 1989, pp. 10–13.

Calvor et al., "Production of Microparticles by High Pressure etc.", *Pharm. Dev. Tech.*, 3(3), 297–205, 1998.

Charles et al., Vickers Micromechanical Indentation of Sodium Antimony Fluoride (NaSb$_2$F$_7$ and Na$_3$F$_{15}$) Single Crystals, *J Mater Sci Lett*, 9[2], 1990. Abstract.

Cherney, L.S., "Tetracaine Hydroiodide: A Long Lasting Local Anesthetic Agent for the Relief of Postoperative Pain", *Anesth. Analg.* (1963) vol. 42, No. 4, pp. 477–481.

Chulia et al., Powder Technology and Pharmaceutical Processes, (1994), pp. 66–67.

Cudd et al., "Liposomes Injected Intravenously into Mice Associate with Liver Mitochondria," *Biochem. Biophys. Acta*, (1984) vol. 774, pp. 169–180.

Friedrich, Klaus, "Erosive Wear of Polymer Surfaces by Steel Ball Blasting", *J Mater Sci*, 21 [9], 1986. Abstract.

Gennaro et al., "Sustained–Release Drug Therapy," *Remington's Pharmaceutical Sciences*, 17$^{th}$ Ed., (1985), p. 1645.

Gock et al., "Eccentric Vibratory Mills–Theory and Practice", *Powder Technology* 105 (1999), p. 302 (Abstract).

Goodman and Gillman's, "The Pharmacological Basis of Therapeutics," 7$^{th}$ Ed., *MacMillan Publishing Co.*, New York (1985) Chap. 15, p. 312.

Gregoriadis, Gregory, "The Carrier Potential of Liposomes in Biology and Medicine", *New Engl. J. Med.*, (1976), vol. 295, No. 13, pp. 704–710.

Gutsche et al., Fracture Kinetics of Particle Bed Comminution–Ramificatin for Fines Productin and Mill Optimization, *Powder Technology* 105 (1999), p. 113 (Abstract).

Guzman et al., 'Formation and Characterization of Cyclosporine–Loaded Nanoparticles', *1088 J. Pharm. Sci* 82 (1993) No. 5 pp. 498–502.

Haynes et al., "Metal–Ligand Interactions in Organic Chemistry and Biochemistry", *B. Pullman and N. Goldblum* (eds), part 2, (1977), pp. 189–122.

Haynes et al., "Ultra–Long Duration Local Anesthesia Produced by Injection of Lecithin–coated Methoxyflurane Microdroplets", *Anesthesiology* (1985) vol. 63, No. 5, pp. 490–499.

Haynes et al., "Ultra–Long Duration Local Anesthesia Produced by Intra–Dermal Injection of Lecithin–Coated Methoxyflurane Microdroplets", *Proceed. Intern. Symp. Control. Rel. Bioact. Mater.*, (1987) vol. 14, pp. 293–294.

Herbert A. Leiberman and Leon Lachman, Eds., *Pharmaceutical Dosage Forms*, Tablets, vol. 1, (1980), p. 13.

Hogg, R., "Breakage Mechanisms in Mill Performance in Ultrafine Grinding", *Powder Technology* 105 (1999), p. 135 (Abstract).

Huang et al., "Interaction of the N–terminus of Sterol Carrier Protein 2 with Membranes: Role of Membrane Curvature", *Biochem. J*, (1999) vol. 8, pp. 593–603.

Kerr et al., "Comparative Grinding Kinetics and Grinding Energy During Ball Milling and Attrition Milling", *Laboratory Report*, vol. 71, No. 12 (1992), p. 1809 (Abstract).

Kirkpatrick et al., "Local Anesthetic Efficacy of Methoxyflurane Microdroplets in Man," *Anesthesiology* (1987) 67(3A): A254.

Kwade, Arno, "Determination of the Most Important Grinding Mechanism in Stirred Media Mills by Calculating Stress Intensity and Stress Number", *Powder Technology* 105 (1999), p. 382 (Abstract).

Kwade, Arno, "West Comminution in Stirred Media Mills–Research and its Practical Application", *Powder Technology* (105), p. 14 (Abstract).

La Fuma, Francoise, "The Role of Water–Soluble Polymers at the Solid/Liquid Interface in the Mechanisms of Flocculation/Stabilization of Aqueous Colloidal Suspensions", *Polimery*, 1998 43 nr 2, 104–108.

Lehninger Biochemistry, "The Molecular Basis of Cell Structure and Function", (1970) Chapter 10.

Lourenco et al., "Steric Stabilization of Nanoparticles: Size and Surface Properties", *Int. J. of Pharm.* 138 (1996), 1–12.

Luckham, "The Physical Stability of Suspension Concentrates with Particular etc.", *Pestic. Sci.*, 1989, 25, 25–34.

Mishra et al., "Scientifically Speaking: Novel Injectable Formulations of Water–Insoluble Drugs", *Controlled Release Newsletter*, vol. 17, Issue 2, (Jun. 2000), pp. 21–30.

Miyajima, Koichiro, "Role of Saccharides for the Freeze–Thawing and Freeze–Drying of Liposome", *Advanced Drug Delivery Review*, vol. 24, (1997), pp. 151–159.

Muller et al., "Nanosuspensions for the I.V. Administration of Poorly Soluble Drugs–Stability During Sterilization and Long–Term Storage", Dept. of Pharmaceutics, *Biopharmaceutics and Biotechnology*, The Free University of Berlin, Kelchstraβe 31, D–12169 Berlin, Germany.

Muller et al., Emulsions and Nanosuspensions, Chap. 9 (1998) p. 163.

Napper, Donald, "Polymeric Stabilizations of Colloidal Dispersions", (1983).

Pace et al., "Novel Injectable Formulations of Insoluble Drugs", *Pharmaceutical Technology*, vol. 23, No. 3, (Mar. 1999), pp. 116–134.

Padden et al., "Grinding Kinetics and Media Wear", *Laboratory Report*, vol. 72, No. 3 (1993), p. 101.

Park et al., "Effect of Carbides on the Microstructure and Properties of Ti(C,N)–Based Ceramics", *J Am Ceram Soc.*, 82 [11], (1999), p. 3150–3154.

Rompp's Chemie Lexikon, 2 Aufl., Bd. 1, (1950), Stichwort, "Emulsion".

Ross et al., "Aqueous Solutions of Surface–Active Solutes", *Colloidal Systems and Interfaces*, ©1988, pp. 148–151.

Sande et al., "Antimicrobial Agents: Antifungal and Antiviral Agents", pp. 1219–1222.

Siekmann et al., "Melt–homogenized Solid Lipid Nanparticles Stabilized by the Non–Ionic Surfactant Tyloxapol", *Pharm. Pharmacol Lett* (1994) 3:225–228.

Summers, Wade, 'Broad Scope Particle Size Reduction by Means of Vibratory Grinding', *Ceramic Bulletin* (1982), p. 212.

Theuerkauf et al., 'Theroretical and Experimental Investigation of Particle and Fluid Motion in Stirred Media Mills', *Powder Technology* 105 (1999), p. 406 (Abstract).

Varinot et al., 'Prediction of the Product Size Distribution in Association of Stirred Bead Mills', *Powder Technology* 105 (1999), p. 228 (Abstract).

Website http://userpage.fu–berlin.de/~kayser/nanosuspensionen.htm.

Wu et al., "Pharmacokinetics of Methoxyflurane After Its Intra–Dermal Injection as Lecithin–Coated Microdroplets," *Journal of Controlled Release*, (1989), vol. 9, pp. 1–12.

Zuidam et al., "Sterilization of Liposomes by Heat Treatment", *Pharmaceutical Research*, vol. 10, No. 11, 1993, p. 1591–1596.

* cited by examiner

MILLED PARTICLES

This application claims the benefit of Provisional Application 60/229,042, filed Jul. 31, 2000.

FIELD OF THE INVENTION

This invention relates to compositions of small particles of milled solid materials synergetically commixed with small particulates of milling media of comparable or smaller size, and to milling processes for their preparation employing combinations of two or more milling media materials selected according to their relative fracture toughness, hardness, and brittleness index values.

BACKGROUND OF THE INVENTION

Size reduction to produce small particles of crystalline and amorphous solid materials, now widely used in a variety of industries, can be accomplished by mechanical means using dry or wet milling techniques including jet milling, ball milling, media milling, and homogenization.

Small particles of a solid material, and in particular small particles of a poorly soluble or essentially insoluble solid, find beneficial use in numerous applications related to the increase in surface area achieved as a result of size reduction. When incorporated into a mixture, formula, composition, chemical reaction, dispersion, coating, powder, lyophilizate, suspension, matrix, and the like, a solid material in the form of small particles exhibits greater homogeneity in macroscopic or static properties such as observed or perceived color and uniformity of distribution, and improved microscopic or kinetic properties such as increased rate of dissolution into a volume of solvent or a volume of liquid including a pseudo-infinite solvent pool volume.

In one aspect, with respect to a solid drug substance, a volume of liquid can be a volume of liquid used in or administered with a dosage form of the drug such as from about 100 microliters to about 100 milliliters, often 1 milliliter to about 50 milliliters. In another aspect, with respect to a solid drug substance, a volume of liquid can be a volume of liquid found in a patient to which a dosage form of the drug is administered. For example, the volume of liquid can include the volume of blood in a patient, the volume of urine in a patient, the plasma volume in a patient, the volume of lymph in a patient, the volume of liquid in the stomach of a patient, the volume of liquid in the gastrointestinal tract of a patient, ascites fluid volume in a patient, the volume of liquid in a cyst in a patient, the volume of liquid in the eye of a patient, the volume of liquid in the lung of a patient, and the like. The volume may be the entire volume of a specific kind of fluid or liquid or it can be an aliquot or less than 100% of the total volume.

Small particles of a solid material often require the presence of one or more surface-active substance particularly on the surface of the particles to achieve or augment particle stability especially with respect to particle size increase and stability of a suspension of particles without agglomeration or aggregation in a liquid.

In recent years there has been a transition to the use of small milling media in conventional media mill processes of solid substrates for the preparation of various paints, pigment dispersions, photographic dispersions, pharmaceutical dispersions, and the like. The advantages obtained with the use of smaller size media include faster rates of solid substrate particle size reduction and more rapid attainment of smaller solid substrate particle size distributions as products of the milling process, i.e., more efficient comminution. Improvements in conventional media mill designs such as in Netzsch LMC mills and Drais DCP mills have incorporated smaller screen opening dimensions that allow physical separation (e.g., filtration) of larger milling media from milled substrate particles as small as 250 to 300 micrometers or less. However, even with the best machine designs available, it is generally not possible to use milling media bodies smaller than about 250 to 300 micrometers due to separator screen plugging proximal to the milling chamber and unacceptable pressure build-up due to hydraulic packing of the media. Commonly, for commercial applications, a grinding media size of 350 micrometers is considered the practical lower limit for media particle retention due to media separator screen limitations.

In applications such as pharmaceutical applications it is often desirable to prepare dry formulations of small particles of a solid optionally containing one or more additional ingredients such as an excipient. The ease of resuspension of individual particles rather than agglomerates of particles from dry dosage forms such as capsules, wafers, tablets and powders into fluids such as bodily fluids, for example gastrointestinal fluids and mucosal fluids, and into liquids such as water often in the form of a volume used to administer or comprise a dosage form of a drug is often improved by the presence of such excipients. The subsequent rate of dissolution of drug from resuspended particles in such formulations, and often the bioavailability of a poorly water soluble drug in the form of a resuspended particle rather than as an agglomerate, can increase as a function of increasing surface area and decreasing particle size. Small particles of a solid drug intimately dispersed in a formulation containing one or more excipients can function as isolated sources of the solid substance especially when the particles do not agglomerate or associate strongly with each other to form clusters or agglomerates of small particles. While small particles can sometimes be mixed in bulk formulation processes with other formulation ingredients such as excipients in a pharmaceutical process, it is not always the case that uniform distributions of all ingredients are achieved. In mixing processes involving small particles, it is not always possible to achieve complete separation of small particles that are present in agglomerates or in associated clusters to produce a formulation of separated small particles surrounded by other components of the formulation. Generation of pharmaceutically acceptable excipient particles of molecular clusters or pieces or fragments of excipient during a size reduction process can offer a potential improvement over prior art.

The advantages in drug delivery of water-insoluble drugs formulated as small particles have been described in a review by Pace et al., "Novel injectable formulations of insoluble drugs," in Pharmaceutical Technology, March 1999 the contents of which are hereby incorporated by reference.

There has been a bias in the pharmaceutical art against wet milling due to concerns associated with contamination from fragments of non-pharmaceutically acceptable or toxic milling media bodies. Contamination by milling media body fragments can introduce non-biocompatible materials into pharmaceutical formulations to produce toxic effects in patients. For example, contamination can produce deleterious effects if formulations containing relatively large size fragments of solid materials (i.e., greater than about 10 microns) are administered by injection and block capillary vessels. Other effects of contamination by media and fragments of media include the introduction of heavy metal ions such as yttrium, and pH changes caused by the introduction of metal oxides that can in turn promote changes in drug substance during storage related to catalyzed reactions such as hydrolysis, oxidation, radical reactions, electron transfer reactions, condensation reactions, and other types of chemical reactions.

Czekai et al. in U.S. Pat. Nos. 5,513,803 and 5,718,388 disclose the use of ultrafine milling media for the preparation of fine particles useful in imaging elements, pigments and pharmaceuticals. Czekai et al. also disclosed simultaneous use of a mixture of large and small size milling media of identical composition wherein the larger size media were retained in the milling chamber while the smaller size media were not retained within the milling chamber. Grinding media in a preferred embodiment comprise particles of a polymeric resin. The use of polymers that are biodegradable is also disclosed with the stated advantage that contaminants from the media can advantageously metabolize in vivo into biologically acceptable products which can be eliminated from the body.

Liversidge et al. in U.S. Pat. No. 5,145,684 and in European Patent Application 498,492 describe dispersible particles consisting of a drug substance or an x-ray contrast agent having a surface modifier adsorbed on the surface thereof in an amount sufficient to maintain an effective average particle size of less than about 400 nm. The particles are prepared by dispersing a drug substance or imaging agent in a liquid dispersion medium and wet grinding in the presence of rigid grinding media.

Beneficial effects of incorporation of fragments or debris from milling media into a milled substrate have been reported. For example, Cottringer et al. in U.S. Pat. Nos. 4,623,364 and 5,383,945 describe a method for preparing high density sintered polycrystalline alpha alumina abrasive grits from non-alpha alumina gels by introduction of seed material during wet vibratory milling with alpha alumina media prior to firing. Particulate matter or debris worn from alumina grinding media is introduced from the milling media and effects seeding of the crystallization of alpha alumina during firing. Additionally, it is suggested that other impurities such as $SiO_2$, $Cr_2O_3$, MgO, and $ZrO_2$ introduced in the milling step may serve as grain growth inhibitors and inhibit crystal growth of the final product by their presence at grain boundaries between alpha alumina particles. However, no mention was made of using more than one type of milling media in this process.

Park et al. in "Effect of carbides on the microstructure and properties of Ti(C,N)-based ceramics," J. Am. Ceram. Soc. (1999), 82(11), 3150–3154 studied powdered Ti(C0.5N0.5) that was premixed with powdered NbC, TaC, WC, or $Mo_2C$ and then milled, dried, pressed, and sintered. Metal impurities introduced from the milling media (especially from WC—Co alloy balls) were sufficient to promote densification in sintering. Only one type of media was used.

The simultaneous use in a mill of milling media of mixed sizes and shapes is widely known. For example, U.S. Pat. No. 5,611,829 discloses the milling of an alpha-alumina seed sol in an alumina ball mill with a mixture of alumina mill media of different sizes and shapes consisting of equal amounts of 0.5 inch (1.3 cm) balls, 0.5 inch (1.3 cm) cylinders, and 0.75 inch (1.9 cm) cylinders). However, the media are all of the same alumina composition. Use of mixed sizes of milling media bodies of the same composition have been repeatedly mentioned, for example in U.S. Pat. Nos. 5,902,711, 5,834,025, 5,747,001, 5,718,919, 5,718,388, 5,679,138, 5,565,188, 5,513,803, and 5,500,331.

Media load effects both the grinding time and power absorbed in a milling process. When the media occupies 50% of the total mill volume, the grinding time is minimized and power adsorbed is maximized. When a milling chamber is loaded with 50 to 55% by volume with milling media, as a general rule the media charge should consist of 25% of small size milling media balls, 50% of medium size milling media balls, and 25% of large size milling media balls for maximum grinding efficiency.

The simultaneous use in a mill of milling media bodies of mixed compositions has been reported. For example, U.S. Pat. No. 5,022,592 discloses a magnetic media mill that can simultaneously use a combination of magnetic and non-magnetic media. The media can comprise some media which are not magnetic or magnetizable. In addition, individual media particles can comprise both magnetizable and non-magnetizable material.

U.S. Pat. No. 3,521,825 discloses a method of providing a homogeneous dispersion into a matrix of a first material such as a tungsten powder of one or more very fine second phase materials such as alumina ($Al_2O_3$) or thoria ($ThO_2$) derived from milling balls composed of the second phase materials through a milling process which causes abrasion of the second phase material of the milling balls. However, the tungsten powder in the milling process is not reduced in size in this process.

U.S. Pat. No. 5,139,719 discloses a method of preparing sintered silicon carbide/boride materials in which silicon carbide and a boron-containing material are wet milled with elemental carbon or with an organic polymer or resin decomposable to give elemental carbon on sintering, dried, and dry milled to produce a homogeneous powder. The elemental carbon acts as a sintering aid.

Contamination of pharmaceutical materials by fragments of grinding media has been recognized, and media selection to minimize or keep levels of contamination to acceptable levels has been reported. Liversidge et al. in U.S. Pat. No. 5,552,160 state that selection of material for the grinding media is not believed to be critical. They also state that zirconium oxide stabilized with magnesia, zirconium silicate, and glass grinding media provide particles having levels of contamination which are believed to be acceptable for the preparation of pharmaceutical compositions.

Bruno et al. in U.S. patent application Ser. No. 07/981,639 filed Nov. 25, 1992 (abandoned) disclose polymeric grinding media for fine grinding pharmaceutical compositions.

U.S. Pat. No. 5,662,279 describes the milling of a slurry of a compound using rigid milling media bodies to reduce the particle size of the compound wherein removal of the product from the milling media bodies was done in a subsequent step by vacuum filtration through a removable filter probe attached to a conduit immersed in the slurry.

U.S. Pat. No. 5,585,108 discloses the formation of particles of oral gastrointestinal therapeutic agents in combination with pharmaceutically acceptable clays including 1 to 2% of a montmorillonite, beidelite, nontronite, hectorite and saponite which contain aluminium, iron, magnesium and silicon as oxides and hydrates.

U.S. Pat. Nos. 5,470,583 and 5,336,507 disclosed methods for preparation of nanoparticles using a charged phospholipid as a cloud point modifier and one type of media in a milling process.

U.S. Pat. No. 5,302,401 disclosed compositions and methods for forming nanoparticles with a surface modifier and a cryoprotectant adsorbed thereon using one type of media in a milling process.

U.S. Pat. No. 5,478,705 disclosed a process for the preparation of solid particles of a compound useful in photographic, electrophotographic, or thermal transfer imaging elements having an average particle size of less than 1 micron which comprises milling the compound in the presence of milling media bodies comprising a polymeric resin.

U.S. Pat. No. 5,500,331 discloses a method of preparing submicron particles which comprises milling in the presence of milling media having a mean particle size of less than about 100 microns. The milling media are of a chemically and physically inert polymeric resin of sufficient hardness and friability to enable them to avoid being chipped or crushed during milling. Polystyrene media of sizes 5, 25, 50, 75, and 450 microns are disclosed.

Efforts to reduce the level of undesired contaminants introduced into milled particles by milling media have been described. U.S. Pat. No. 5,679,138 compares the relatively high level of trace metal ion contaminants introduced by ceramic zirconium silicate bead milling media versus that found when polystyrene beads were used to produce ink jet ink concentrate.

U.S. Pat. No. 5,718,919 discloses a microprecipitation method for preparing small particles of a drug where the product is free of heavy metal contaminants arising from milling media that must be removed due to their toxicity before the product is formulated.

U.S. Pat. No. 4,775,393 discloses a method of milling silicon carbide to a submicron powder using silicon carbide grinding media that avoids introduction of iron, alumina, and boron impurities found in non-silicon carbide media.

U.S. Pat. No. 5,518,187 discloses a method of preparing particles of a drug substance or diagnostic imaging agent by grinding in the presence of a polymeric resin grinding media.

U.S. Pat. No. 5,534,270 discloses a method of preparing sterilized nanoparticulate crystalline drug particles using rigid grinding media having an average particle size less than 3 mm. Wet grinding of the drug substance was done to maintain an effective average particle size of less than 400 nm using zirconium silicate beads, zirconium oxide stabilized with magnesia, or glass beads.

U.S. Pat. No. 5,657,931 discloses a process for the preparation of an aqueous dispersion of a substantially water-insoluble non-polymeric organic compound by forming a coarse aqueous slurry of solid particles of compound and an amphipathic water-soluble or water-dispersible block polymeric dispersant and then milling the slurry to provide particles of less than 0.5 micron.

U.S. Pat. No. 5,704,556 discloses a media milling process for producing colloidal particles using ceramic beads of zircon, glass, and yttrium toughened zirconium oxide less than 100 microns in diameter in which the diameter of the ceramic milling media beads is no more than about one hundred times the average particle size of the feedstock particles.

U.S. Pat. No. 5,862,999 discloses a method of grinding particles of a therapeutic or diagnostic agent in the presence of rigid grinding media having a mean particle size of less than about 100 microns. The particles produced have an average particle size of less than about 500 nm and are free of unacceptable contamination caused by the media deterioration.

U.S. Pat. No. 5,902,711 discloses a process of forming milled solid particles of an electrophotographic toner pigment compound by milling in a liquid organic medium continuous phase in the presence of polymeric milling media. The compound particles are milled to an average particle size of less than 100 nm.

U.S. Pat. No. 4,880,634 describes a method of production of an excipient system containing a pharmacologically active substance for peroral administration comprised of lipid nano-pellets in an aqueous, colloidal suspension. The method comprises forming a melt of a mixture of at least one surfactant, a pharmacologically active substance, and at least one lipid, dispersing the molten mixture within an aqueous solution at a temperature above the melting point of the lipid to form lipid nano-pellets, and cooling the suspension below the melting point of the lipid.

U.S. Pat. No. 5,922,355 discloses a method for preparing submicron size microparticles by particle size reduction methods in which a solid material is reduced in size over a period of time while continuously below the melting point of the material or by precipitation while the particles are stabilized with phospholipids as surface active substances in combination with other surface modifiers to control growth of particle size and enhance storage stability. The use of one or more surface modifiers in addition to a phospholipid provides volume weighted mean particle size values that are much smaller than what can be achieved using phospholipid alone without the use of an additional surface active substance (surfactant) with the same energy input while providing compositions resistant to particle size growth on storage. The phospholipid and the surfactant are both present at the time of particle size reduction.

U.S. Pat. Nos. 5,091,187 and 5,091,188 disclose water-insoluble drugs that can be injectable as aqueous dispersions of phospholipid-coated microcrystals. The crystalline drug is reduced to 50 nm to 10 micrometers processes inducing high shear in the presence of phospholipid or other membrane-forming amphipathic lipid.

U.S. Pat. No. 5,700,471 discloses a process for the micronization of compounds having low solubility in water by exposing them briefly to a temperature above their respective melting points, dispersing them with turbulence in an aqueous or organic phase, and subsequently cooling the phase to form a fine particle dispersion.

International Patent Application WO 99/39700 describes the preparation of submicron nanoparticles from a pharmacologically active principle and a composite material consisting of at least one lipidic substance and at least one amphiphilic substance using high pressure homogenization to form a microemulsion of the composite material at a temperature higher than the melting temperature of at least one of the materials forming the composite and in the presence of one or more aqueous surfactants as surface active substances and then cooling the microemulsion to form a dispersion of solid particles.

WO 97/14407 discloses particles of water insoluble biologically active compounds with an average size of 100 nm to 300 nm that are prepared by dissolving the compound in a solution and then spraying the solution into compressed gas, liquid, or supercritical fluid in the presence of appropriate surface modifiers.

OBJECTIVES OF THE INVENTION

While the incorporation of milling media body fragments during a milling process into milled product particles has found use when the fragments are beneficial to or exhibit no undesired or adverse effects in a milled solid, a method is needed to beneficially increase the incorporation of such materials into milled solids. It is therefore an object of this invention to provide such a method for the beneficial incorporation of milling media particulates into a milled solid, and to provide novel compositions comprising particles of milled solid materials and particulates of milling media.

It is another object of this invention to provide a method for the preparation of a pharmaceutical composition comprising particles of a milled pharmaceutical agent and biocompatible particulates of milling media.

It is another object of this invention to provide compositions and methods for the formation of a plurality of small particles of a solid substrate that have particulates of milling media uniformly dispersed among the small particles.

It is another object of this invention to provide an improved milling process wherein a solid substrate is efficiently reduced in size to a plurality of small particles by contact with milling media bodies in a media mill, which milling media bodies provide by their fragmentation small particulates or fragments of milling bodies that remain distributed among and are not detrimental to the use of the plurality of small particles of solid substrate.

It is another object of this invention to provide compositions and methods for the preparation of a synergetic commixture of small particles of a solid substrate and small particulates of milling bodies.

BRIEF SUMMARY OF THE INVENTION

We have discovered a process for milling a solid substrate in the milling chamber of a media mill to a desired size in the presence of two or more compositions of milling media bodies wherein all milling media bodies contribute to the grinding or milling of the solid substrate and wherein at least one composition of media bodies provides fragments or particulates that are of said desired size and are retained, partially or completely, with the milled solid substrate particles as a synergetic commixture produced in the milling process. Such particulates are produced primarily by the kinetic interaction of milling bodies with other components present in the milling chamber. In one aspect, the particulates are produced primarily by the kinetic interaction of milling bodies of a first composition with other components present in the milling chamber and in particular with milling bodies of a second composition. In one preferred aspect, the particulates are inert or benign with respect to a subsequent use of compositions comprising the milled solid particles and particulates produced in the milling process. In another preferred aspect, the fragments or particulates are beneficial to a subsequent use of compositions comprising milled solid particles and particulates produced in the milling process. In another preferred aspect, the solid is a poorly soluble pharmaceutical agent, and the particulates are inert with respect to a subsequent use of a formulation comprising the milled solid particles of pharmaceutical agent and particulates produced in the milling process. In yet another preferred aspect, the solid is a pharmaceutical agent, and the particulates are beneficial with respect to a subsequent use of a formulation comprising the milled solid particles of pharmaceutical agent and particulates produced in the milling process. In a most preferred aspect, the solid is a poorly water soluble pharmaceutical agent and the particulates of fragmented milling media are an excipient material in a formulation or part of a formulation of a dosage form comprising small particles of a poorly water soluble pharmaceutical agent and particulates of milling media bodies produced in the milling process.

In this invention the fragments of milling media bodies distributed among the particles of solid substrate are not detrimental to the use of the milled solid particles. In one aspect the fragments of milling media bodies distributed among the particles of solid substrate are inert with respect to the therapeutic activity or therapeutic application of a dosage form of the small particles of drug and do not interfere with any aspect of formation of a dosage form or do not exhibit detrimental effects such as toxic effects when administered to a patient as part of a dosage form. In another aspect the fragments of milling media bodies distributed among the particles of solid substrate are beneficial with respect to the therapeutic activity or therapeutic application of a dosage form of the small particles of drug and can supplement or assist or augment or are synergetic in some manner with at least one property of the small particles. In this regard, the fragments of milling media bodies as excipients in a formulation can aid in formation of a dosage form such as a tablet or capsule or powder or wafer containing the drug and optionally additional excipients, can aid in the redispersal of the small particles into a liquid such as water or an aqueous liquid that is part of or administered with a dosage form of the drug or into a liquid in a patient such as gastrointestinal fluid, urine, lymph, ascites fluid, mucous, and the like.

More specifically, we have discovered a process for preparing a synergetic commixture comprising small particles of a solid substrate and small particulates of a first material of a desired size, said process comprising the steps of:

(a) providing to the milling chamber of a media mill a contents comprising a pre-mix of a solid substrate, a fluid carrier, a plurality of milling bodies of a first material, and a plurality of milling bodies of a second material;

(b) operating said media mill to grind said solid substrate and degrade at least a portion of said milling bodies of first material to produce a dispersion in said fluid carrier comprising a synergetic commixture of small particulates of said first material and small particles of said solid substrate having a desired size equal to or less than a size Sp;

(c) separating said dispersion from any residual milling body, piece of milling body, and solid substrate having a size larger than Sp; and (d) optionally removing said fluid carrier from said dispersion to form a dry synergetic commixture comprising said particles and said small particulates; wherein, the milling bodies of said first material are fractured and eroded by the milling bodies of said second material, the milling bodies of said second material are essentially substantially resistant to fracture and erosion in the milling process, and Sp is smaller than the size of the milling media bodies of the second material.

In another embodiment of this invention, we have discovered a process for preparing a synergetic commixture comprising small particles of a solid substrate and small particulates of a first material of a desired size, said process comprising the steps of:

(a) providing to the milling chamber of a media mill a contents comprising a pre-mix of a solid substrate, a fluid carrier, a plurality of milling bodies of a first material having a fracture toughness $K_{C1}$, and a plurality of milling bodies of a second material having a fracture toughness $K_{C2}$;

(b) operating said media mill to grind said solid substrate and degrade at least a portion of said milling bodies of first material to produce a dispersion in said fluid carrier comprising a synergetic commixture of small particulates of said first material and small particles of said solid substrate having a desired size equal to or less than a size Sp;

(c) separating said dispersion from any residual milling body, piece of milling body, and solid substrate having a size larger than $S_p$; and (d) optionally removing said fluid carrier from said dispersion to form a synergetic commiixture free of fluid and comprising said particles and said small particulates;

wherein $K_{C2}$ is greater than $K_{C1}$.

In another embodiment of this invention, the milling media bodies can comprise a mixture of media bodies of a first material having a fracture toughness $K_{C1}$ and milling media bodies of a second material having a fracture toughness $K_{C2}$ wherein $K_{C1}$ is less than $K_{C2}$ and the size of the media bodies of the first material is larger than the size of the media bodies of the second material.

In yet another embodiment of this invention, the milling media bodies can comprise a mixture of milling media bodies of a first material having a fracture toughness $K_{C1}$ and milling media bodies of a second material having a fracture toughness $K_{C2}$ wherein $K_{C2}$ is greater than $K_{C1}$ and the size of the media of the first material is smaller than the size of the milling media bodies of the second material.

In yet another embodiment of this invention, the milling media bodies can comprise a mixture of media of a first material having a fracture toughness $K_{C1}$ and media of a second material having a fracture toughness $K_{C2}$ wherein $K_{C2}$ is greater than $K_{C1}$ and the size of the media of the first material is the same as the size of the media of the second material.

In yet another embodiment of this invention, the milling media bodies can comprise a mixture of media of a first material having a brittleness index $B_{1L}$ and a second material having a brittleness index $B_{2L}$, wherein $B_{1L}$ is less than $B_{2L}$, and $B_{1L}$ and $B_{2L}$ are less than about 5.5.

In yet another embodiment of this invention, the milling media bodies can comprise a mixture of media of a first material having a brittleness index $B_{1H}$ and a second material having a brittleness index $B_{2H}$, wherein $B_{1H}$ is greater than $B_{2H}$ and both $B_{1H}$ and $B_{2H}$ are greater than about 5.5.

In yet another embodiment of this invention, the milling media bodies can comprise a mixture of media of a first material having a hardness $H_1$ and a second material having a hardness $H_2$, wherein $H_1$ is less than $H_2$.

In preferred embodiments of the invention, milling is performed by high speed mixing of a premix comprising a solid substrate together with a plurality of milling bodies of a first material and a plurality of milling bodies of a second material dispersed in a fluid carrier in the milling chamber of a media mill.

In a preferred embodiment the milling bodies of the first material are smaller than the milling bodies of the second material and equal to or less than the size of the desired small particles of solid produced in the milling process; the milling bodies of the second material are larger than the milling bodies of the first material and larger than the size of the desired small particles of solid produced in the milling process; and the milling bodies of the second material are harder, have a higher fracture toughness, and are less friable than the milling bodies of the first material.

In another preferred embodiment, the milling bodies of the first material are initially larger than the milling bodies of the second material. The milling bodies of the first material are spalled during the milling process, and the sizes of the fragments or pieces of milling media bodies of the first material generated in such spalling are equal to or less than the size of the desired small particles of solid produced in the milling process. The milling bodies of the second material are smaller than the milling bodies of the first material but are larger than the size of the desired small particles of solid produced in the milling process. The residual second milling material and any large size media of the first material can be separated from the product particles and synergetic media particulates by a size dependent method such as filtration. The milling bodies of the second material in this preferred aspect are hard, essentially non-eroding, and have a higher fracture toughness and are less friable than the milling bodies of the first material.

The process is applicable to the wide variety of solid substrates, and to a wide variety of commercially available milling media bodies of a wide range of size, a wide range of hardness, and a wide range of fracture toughness as described below. In a preferred embodiment, the process is applicable to the preparation of particles of a poorly soluble solid pharmaceutical agent and particulates of a milling material that are compatible with the use of the particles of the solid substrate. In a preferred example, particulates of milling media bodies can be incorporated into a formulation or dosage form of particles (such as nanoparticles and microparticles) of a poorly water-soluble drug where both the particulates of the milling media bodies and particles of the poorly water-soluble drug are produced in a milling process.

It is an advantageous feature of this invention that there is provided a milling method which enables the use of ultra-fine milling media, e.g., of a particle size less than 350 micrometers, in a continuous or batch milling process.

It is a particularly advantageous feature of this invention that there is provided a method of preparing extremely fine particles of pharmaceutical agents, particularly poorly water soluble or water-insoluble therapeutic and diagnostic agents.

It is another advantageous feature of this invention that there is provided a grinding method which enables the use of ultra-fine grinding media, e.g., of a particle size less than 350 micrometers, in a grinding process.

Other advantageous features will become readily apparent upon reference to the following description of preferred embodiments.

DETAILED DESCRIPTION OF THE INVENTION

In accordance with this invention, a process is disclosed for preparing a synergetic commixture comprising small particles of a solid substrate and small particulates of a first material of a desired size, said process comprising the steps of:

(a) providing to the milling chamber of a media mill a contents comprising a pre-mix of a solid substrate, a fluid carrier, a plurality of milling bodies of a first material, and a plurality of milling bodies of a second material;

(b) operating said media mill to grind said solid substrate and degrade at least a portion of said milling bodies of first material to produce a dispersion in said fluid carrier comprising a synergetic commixture of small particulates of said first material and small particles of said solid substrate having a desired size equal to or less than a size Sp;

(c) separating said dispersion from any residual milling body, piece of milling body, and solid substrate having a size larger than Sp; and (d) optionally removing said fluid carrier from said dispersion to form a dry synergetic commixture comprising said particles and said small particulates;

wherein, the milling bodies of said first material are fractured and eroded by the milling bodies of said second material, the milling bodies of said second material are essentially substantially resistant to fracture and erosion in the milling process, and Sp is smaller than the size of the milling media bodies of the second material.

In another embodiment of this invention, we have discovered a process for preparing a synergetic commixture comprising small particles of a solid substrate and small particulates of a first material of a desired size, said process comprising the steps of:

(a) providing to the milling chamber of a media mill a contents comprising a pre-mix of a solid substrate, a fluid carrier, a plurality of milling bodies of a first material having a fracture toughness $K_{C1}$, and a plurality of milling bodies of a second material having a fracture toughness $K_{C2}$;

(b) operating said media mill to grind said solid substrate and degrade at least a portion of said milling bodies of first material to produce a dispersion in said fluid carrier comprising a synergetic commixture of small particulates of said first material and small particles of said solid substrate having a desired size equal to or less than a size Sp;

(c) separating said dispersion from any residual milling body, piece of milling body, and solid substrate having a size larger than $S_p$; and (d) optionally removing said fluid carrier from said dispersion to form a synergetic commixture free of fluid and comprising said particles and said small particulates;

wherein $K_{C2}$ is greater than $K_{C1}$.

In another embodiment of this invention, the milling media bodies can comprise a mixture of media of a first material having a fracture toughness $K_{C1}$ and milling media bodies of a second material having a fracture toughness $K_{C2}$ wherein $K_{C1}$ is less than $K_{C2}$ and the size of the media of the first material is larger than the size of the media of the second material.

In yet another embodiment of this invention, the milling media bodies can comprise a mixture of milling media bodies of a first material having a fracture toughness $K_{C1}$ and milling media bodies of a second material having a fracture toughness $K_{C2}$ wherein $K_{C2}$ is greater than $K_{C1}$ and the size of the media of the first material is smaller than the size of the milling media bodies of the second material.

In yet another embodiment of this invention, the milling media bodies can comprise a mixture of media of a first material having a fracture toughness $K_{C1}$ and media of a second material having a fracture toughness $K_{C2}$ wherein $K_{C2}$ is greater than $K_{C1}$ and the size of the media of the first material is the same as the size of the media of the second material.

In yet another embodiment of this invention, the milling media bodies can comprise a mixture of media of a first material having a brittleness index $B_{1L}$ and a second material having a brittleness index $B_{2L}$, wherein $B_{1L}$ is less than $B_{2L}$, and $B_{1L}$ and B2L are less than about 5.5.

In yet another embodiment of this invention, the milling media bodies can comprise a mixture of media of a first material having a brittleness index $B_{1H}$ and a second material having a brittleness index $B_{2H}$, wherein $B_{1H}$ is greater than $B_{2H}$ and both $B_{1H}$ and $B_{2H}$ are greater than about 5.5.

In yet another embodiment of this invention, the milling media bodies can comprise a mixture of media of a first material having a hardness $H_1$ and a second material having a hardness $H_2$, wherein $H_1$ is less than $H_2$.

A synergetic commixture as used herein denotes a composition comprising a first component (for example, particles of a solid substrate) having associated therewith a chemical or physical property (such as particle dispersibility), use (such as a therapeutic agent), or function (such as a therapeutic effect) and a second component (such as particulates of a milling media body) that does not have the same chemical or physical property, use or function as the first component, wherein the commixture composition as a mixture of the first and second component has associated therewith the property, use, or function of the first component in a manner equal to or improved over the level or amount of said property, use, or function of the first component, or the composition has associated therewith a new property, use, or function that is not associated with the first component in the absence of the second component or with the second component in the absence of the first component.

In a communition or media milling process, grinding aids or milling media (also referred to herein as milling media bodies or media bodies) are combined with a solid to be milled and mechanical energy is applied. Repeated collisions of milling media bodies with a solid material being milled, sometimes referred to as the milled solid substrate, result in repeated fracturing, chipping or breaking (i.e., spalling) of the substrate leading to substrate particle size reduction to a desired size smaller than the size of the solid substrate before milling. When a media milling process is used to reduce the size of particles of a solid substrate to a desired size, the process is usually carried out in a milling chamber of a media mill. The milling chamber is provided with a contents comprising milling or grinding media, a pre-mix of a solid material (or solid substrate) which is to be milled, and a liquid or gaseous fluid carrier in which the media and substrate can be suspended. Optionally, one or more additional components such as a polymer, surfactant or surface active agent, viscosity modifying agent, buffering agent, pH controlling agent, chelating agent, bulking agent, excipient agent, ionic strength adjusting agent, coloring agent, and the like can be added to the milling chamber.

A media mill such as an agitator ball mill, an attrition mill, or a stirred mill, has several advantages including high energy efficiency, high solids handling, narrow size distribution of the product output, and the ability to produce homogeneous slurries in the fluid carrier. The major variables in using an agitator ball mill are agitator speed, suspension flow rate, residence time, slurry viscosity, solid size of the in-feed, milling media size and desired product size of the solid substrate being milled. Agitator mills can grind particles to a mean particle size approximately 1/1000 of the size of the milling media bodies in an efficient operation. While the desired size, $S_p$, (also sometimes referred to as the desired size distribution or size range) of particles of solid substrate being milled depends on the intended application, Sp is preferably less than 1 mm, and more preferably less than 100 micrometers. In some embodiments Sp is less than 10 micrometers, and more preferably less than 2 micrometers such as for particles of poorly water soluble or insoluble drugs where preferably the size is less than one or two micrometers or even less than 0.5 micrometers. In one aspect in order to obtain mean particle sizes on the order of 0.05 micrometer to 0.5 micrometer, milling media having a size of less than 0.45 or 0.5 mm can be used. Milling media bodies having diameters of about 0.2 mm and about 0.6 mm are available for example from Tosoh Ceramics, Bound Brook, N.J. To optimize milling, it is desirable to use milling media bodies approximately 1000 times the desired size or desired size distribution, $S_p$, of the particle. This minimizes the time required for milling.

In one aspect, a desired size or desired size range of milled substrate can be from about 0.05 micrometers to about 1 mm, preferably from about 0.1 micrometers to about 0.5 mm, more preferably from about 100 nanometers to about 100 micrometers, sometimes from about 200 nanometers to about 50 micrometers, or from about 400 nanometers to about 10 micrometers, or from about 500 nanometers to about 7 micrometers.

If the desired size of the solid particles produced in a milling process of this invention is very small, it is often necessary to provide one or more surface active substance in the media chamber. One or more surface active substance can be added separately, as a solid or liquid, as a mixture, as a solution, as a suspension, as a dispersion in a fluid carrier or in a component of a fluid carrier, or as a mixture with a solid substrate to be milled as part of the pre-mix. One or more surface active substance can be added batchwise at the beginning of the milling process or during the milling process, and mixing can occur in the milling chamber. Alternatively, one or more surface active substance can be added continuously during the milling process, for example, as a solution or a dispersion in a fluid carrier. Alternatively, one or more surface active substance can be added at different times during the milling process, for example, to the premix before milling, to the premix during the start of milling, during the milling process, and/or near or at the end of the milling process. Different surface active substances can be added at different times, or mixtures of different surface active substances can be added at different times. The composition of such mixtures can be the same or can be different during the period of addition, for example from about 1 second to about 10 hours or up to about 100 hours. As an example, in a two surface active substance system, one component substance can vary in mole fraction from zero to one while the other component substance can vary from one to zero during the period of addition. Both stepwise and continuous variations as well as random or partial variations of concentration can be applicable in surfactant addtion, such as for example addition of a constant amount of one or first surface active substance and a variable amount of another or second surface active substance.

In the milling process, the contents of the milling chamber are stirred or agitated with a stirrer or agitator, which transfers energy to the milling media. The accelerated media collide with the solid substrate and with other solids in the media chamber in energetic collisions that can fracture, chip, or shatter the solid substrate material. The accelerated media can also collide with the substrate and can compress substrate between media particles and between media particles and components of the milling chamber. These two-, three-, and multi-body collisions lead to reduction in substrate particle size and eventually lead to a reduction in solid substrate size to a size equal to or less than a desired size, $S_p$. The accelerated media can also collide and otherwise similarly kinetically interact with each other and with components of the milling vessel. Depending on the hardness, brittleness index, and fracture toughness of the media and on the kinetic energies involved, such collisions can cause individual media bodies to break, chip, shatter, or fracture (i.e., spall) into two or more pieces or fragments. Milling media bodies with low fracture toughness values will spall much more readily than media with high fracture toughness values. Media should be tougher than the substrate being milled in order to produce small particles of substrate in the milling process.

A fragment or a piece of a milling media body may be large, i.e., substantially the same size as the antecedent milling body from which it is derived, or a fragment may be small such as a chip or molecular cluster and can be of a size substantially equal to or smaller than the desired size, SP, of the particles of solid substrate produced in the milling process. Large fragments of milling bodies and unfragmented milling bodies may continue to be fragmented or chipped in the milling process to produce small particulates of milling bodies. In the presence of small sized milling media bodies, large size milling media bodies of the same composition can be chipped or fractured in a milling media process to provide additional small particulates of media. If the small particulates are too small to be removed by size dependent separation methods such as filtration which can remove relatively large milling bodies as well as relatively large fragments of milling bodies (i.e., greater than Sp) from small particles of substrate of desired size produced in the milling process, then the particulates can remain and be incorporated as a mixture with the small particles. Particulates of milling media bodies of a first material of this invention are produced in the milling process from milling media bodies of said first material. In this invention, particulates of milling media bodies of a first material of a size equal to or smaller than the desired size of the particles of solid being milled form a synergetic commixture with said particles of solid formed in the milling process. The composition of the milling media bodies of a first material of this invention can be selected such that the particulates derived from said media are synergetic to a property, use, or function of the particles of solid milled to a desired size, $S_p$, in this invention.

An example of a synergetic commixture prepared according to this invention comprises a commixture of small particles of a solid pharmaceutical agent of a desired size and small particulates of an excipient material, which particulates are generated from a first milling media material by interaction with a second milling material. The solid pharmaceutical agent can be a solid poorly water soluble drug, for example such as fenofibrate. The desired size of the particles of drug produced in the milling process can be of a size distribution or size range from about 0.05 micrometers to about 10 micrometers, preferably from about 0.1 micrometers to about 5 micrometers, more preferably from about 0.1 micrometers to about 2 micrometers, and more preferably from about 0.1 micrometers to about 1 micrometer with a more desired size from about 0.5 micrometers to about 1 micrometers. The size or size range of the particulates of excipient material is less than or equal to the desired size of the particles produced in the milling process. An example of a suitable first milling material that can serve as a source of particulates of excipient in the presence of a second, harder and tougher milling material is colloidal silicon dioxide. The particulates are derived from a plurality of colloidal silica milling bodies such as those described herein. The particulates are produced in a milling process that produces particles of the solid drug (for example, fenofibrate or itraconazole or miconazole) in the presence of a plurality of milling bodies of a second material, said second material being a harder material such as zirconium oxide. The second milling material, zirconium oxide in this example, can be selected to be larger (for example, from about 2 to about 1000 times larger) than the size of the particles and particulates produced in the milling process. The milling process can comprise the use of a fluid or fluid carrier. In one aspect of a preferred embodiment for pharmaceutical use, the fluid carrier can be selected from the group consisting of water, a solution of a salt in water, a solution of a carbohydrate in water, and a mixture thereof. The fluid (e.g., water) can be removed from the suspension of particles and particulates in a drying process (e.g., freeze drying, spray drying, fluid bed drying, evaporation, distillation, sublimation, and the like). The larger-in-size second milling material can be removed from the particles and particulates of desired size along with any residual silica materials and any residual solid materials that are larger in size than the desired size of the particles, for example by filtration prior to removal of fluid. Both the first milling material, silica, and the second milling material, zirconium oxide, contribute to the size reduction of the solid in the premix in the process of this invention. The commixture of particles and particulates produced in the milling process is synergetic because the silica particulates are a useful excipient in a formulation of a dosage form comprising the solid drug particles. Typical dosage forms include tablets, capsules, creams, powders, ointments, suppositories, and the like comprising particles of the solid poorly water soluble drug and particulates of silica milling media. The synergetic commixture can provide a more stable dosage form, for example with respect to agglomeration of the particles of solid over a storage period (which may be from about 10 minutes to about 2 years, often from about 10 minutes to about one month, or from about 10 minutes to about 7 days, or from about 10 minutes to about 48 hours) than an otherwise similar dosage form absent the particulates.

Milling or grinding media suitable for use in this invention can be selected from a variety of known and commercially available materials. The media can be made of a number of materials well known in the art including dense and hard materials having a range of fracture toughness such as sand, steel, silicon carbide, ceramics, silicon oxide, silicon nitride, zirconium silicate, zirconium and yttrium oxide, glass, alumina, alpha-alumina, aluminum oxide, titanium, certain polymeric resins such as crosslinked polystyrene and methyl methacrylate, and biodegradable polymers. Composites of inorganic media covered with organic polymers such as crosslinked organic polymers such as crosslinked polystyrene are also useful. In one embodiment, the media can be preferably substantially spherical in shape such as beads. Examples of additional media materials are listed in Tables 1, 2, 3, and 4 below.

Media geometries may vary depending on the application. Examples of media geometries or shapes include spherical or cylindrical beads, rods, tetrahedra, cubes, torroids, and elipsoids.

Milling media bodies can be of various sizes and size distributions that include large milling media particles and smaller milling media particles. The size distribution of the milling media bodies can be narrow (for example, all media are within a size range around a mean size m +/-1% of the mean size or +/-5% of the mean size or +/-10% of the mean size or +/-15% of the mean size or +/-20% of a mean size) in which case the media are substantially uniform or nearly uniform in size. Alternatively, more than one narrow size distribution of media can be used. If two substantially different media sizes are used wherein substantially all of the media can be classified as being of either one or the other size, then the size distribution of the milling media bodies can be described as being bimodal. Polymodal size distributions, for example of three or more distinct and separate size ranges, wherein substantially all of the media can be classified among three or more separate sizes can also be used. In a bimodal distribution, two milling media body size ranges occur with means $m_1$ and $m_2$ and size ranges around the means of $(m_1+/-x_1)$ and $(m_2+/-x_2)$ where all bodies in the range $(m_1+/-x_1)$ are greater than $(m_2+/-x_2)$ where $x_1$ and $x_2$ are percentages of the mean size, for example as above. In a trimodal distribution, three milling media body size ranges occur with means $m_1$ and $m_2$ and $m_3$ and size ranges around the means of $(m_1+/-x_1)$ and $(m_2+/-x_2)$ and $(m_3+/-x_3)$ where all bodies in the range $(m_1+/-x_1)$ are greater than $(m_2+/-x_2)$ and all bodies in the size range $(m_2+/-x_2)$ are greater than $(m_3+/-x_3)$ where $x_1$ and $x_2$ and $X_3$ are percentages of the mean size value, for example as above. Depending on the application, mean sizes can be in the range from 10 cm to 1 cm, from 10 cm to 5 mm, from 5 mm to 1 mm, from 1 mm to 0.5 mm, from 0.5 mm to about 0.1 mm, and from 0.1 mm to about 0.01 mm.

Useful milling media bodies include silicon dioxide in various forms such as glass beads and colloidal silica. Colloidal silica can be obtained in a number of size ranges. For example, basic colloidal silica with an average particle size of 5 nm at 15% solids and containing 0.75% $Na_2O$ is commercially available from Eka Nobel, Inc. of Augusta, Ga. under the trade designation "NYACOL 215." Basic colloidal silica with an average particle size of 5 nm at 15% solids and containing 0.75% $Na_2O$ is commercially available from Nalco Products, Inc. of Naperville, Ill. under the trade designation "NALCO 1115." Basic colloidal silica with an average particle size of 5 nm at 15% solids and containing $NH_3$ is commercially available from Nalco Products, Inc. under the trade designation "NALCO 2326." Basic colloidal silica with an average particle size of S nm at 30% solids and containing 0.65% $Na_2O$ is commercially available from Nalco Products, Inc. under the trade designation "NALCO 1130." Acidic colloidal silica with an average particle size of 20 nm at 34% by weight solids is commercially available from Nalco Products, Inc. under the trade designation "NALCOAG 1034A." Acidic alumina-coated colloidal silica with an average particle size of 20 nm as 20% $SiO_2$ and 4% $Al_2O_3$ is commercially available from Nalco Products, Inc. under the trade designation "NALCOAG 1SJ613." Colloidal silica with an average particle size of 50 nm at 50% by weight solids is commercially available from Nyacol Products, Inc. under the trade designation "NYACOL 5050." Colloidal silica with an average particle size of 99 nm at 50% by weight solids is commercially available from Nyacol Products, Inc. under the trade designation "NYACOL 9950."

Colloidal silica can be used as milling media of a first material according to this invention together with milling media of a second material having a higher fracture toughness, for example as described in Tables 1, 2, 3 and 4 herein or having greater resistance to fracture and erosion or are harder than the first material. In one aspect, it is possible to use one size distribution of silica as a component in the milling process according to this invention, wherein small particulates of silica are synergetically incorporated into a suspension of small particles of a substrate, for example a poorly water soluble drug, said particulates of silica being usefully incorporated into a composition or formulation of poorly water soluble drug particles as a pharmaceutically acceptable excipient, such as an excipient useful in a tablet, capsule, or powdered formulation of the drug particles after removal of the fluid carrier liquid. The mixture of tableted drug particles or drug particles before formulation and the silica particulates can optionally contain other pharmaceutically acceptable excipients and optionally contain additionally added silica or excipient such as one or more sugars, surfactants, release agents, binding agents and the like. The mixture of drug particles and excipients can be administered in a dosage form for example as a tablet or capsule to a patient for the treatment or therapy of a disease or malady or diagnostic imaging procedure at a pharmaceutically useful dose level or amount for which the drug is indicated. When the fragments of milling media are excipients in a formulation of a poorly water-soluble drug, and the formulation disperses in a volume of liquid without agglomeration because of the presence of the excipient, the fragments of excipient can contribute to enhanced bioavailability of the drug in the particles.

In another aspect, milling media bodies of a first material and milling media bodies of a second material can comprise substantially the same composition such as silica but differ in fracture toughness, for example due to differences in porosity (porous media bodies are less tough than non-porous media bodies of the same composition), or size, or added doping agent that has been added in the process of manufacture of the media bodies, or degree of hydration, or crosslinking of the media bodies.

Doping agents in milling media bodies can be substantially uniformly distributed in a milling media body or can be localized as a concentrated cluster of molecules in one or more regions in a milling body. Doping agents can be present at from about 0.5% to about 50% of the composition of the milling media body. Doping agents can be embedded by entrapment without uniform or non-uniform dissolution into the media milling body as very small particulates in a milling media body. Doping agents included in the media composition such as alumina in a silica media body can optionally be synergetically incorporated as fragments or particulates of media bodies into the final composition as a mixture with the solid substrate particles in addition to particulates of silica milling media bodies.

In yet another aspect, three kinds of milling media bodies can be used. Bodies of milling media of a first material, for example silica, and bodies of milling media of a second material, for example aluminum oxide doped silica can have fracture toughness values that are both less than that of milling media bodies of a third material such as zirconia. In this aspect, when milling media bodies of a third material are harder and exhibit a higher fracture toughness value than that of the first and the second material comprising the mixture of compositions, the bodies of third material can chip or fragment or spall the milling media bodies of the first material and the second material to form particulates. The particulates thus can comprise a mixture of fragments of milling media bodies, and when the mixture is made according to this invention, such a mixture is synergetic with the particles of substrate, for example when the mixture of particulates comprise an excipient in a drug formulation wherein the milled particles comprise a drug such as a water insoluble drug. Both the fragments of silica milling media bodies and of aluminum oxide doped silica milling media bodies can be pharmaceutically acceptable excipients in a formulation of particles of a solid drug substance such as fenofibrate.

Silica can also be in the form of glass beads. For example, U.S. Pat. No. 5,674,616 discloses glass beads with improved fracture toughness suitable for use as reflective elements in roadway markings and as media in shot-peening metal cleaning procedures. Glass beads that are smooth and non-porous are tougher with respect to fracture than amorphous silica or colloidal silicon dioxide.

In addition to the milling media mentioned previously, zirconium silicate milling media bodies, chrome steel milling media bodies, carbon steel milling media bodies, zirconium oxide milling media bodies, and glass bead milling media bodies are available commercially from Fox Industries, Fairfield, N.J., USA. Diamond powder media are available from Warren Diamond Powder Company, Olyphant, Pa., USA. Yttria stabilized tetragonal zirconia polycrystal milling media bodies having fracture toughness of 8.5 $MPa(m)^{1/2}$ are available from Norton Advanced Ceramics, Colo. Springs, Colo., USA. High density milling media bodies are more resistant to wear and impact than milling media bodies that contain cavities and pores. High density zirconium silicate milling media beads such as those available from Fox Industries Inc., Fairfield N.J., USA can have a density of about 4.55 grams/$cm^3$ and a crushing strength on a 2 mm bead of 85 kg with a sphericity over 0.8 for 96%. Size ranges for such beads are typically 0.6 to 2.8 mm. These can produce particles of a desired size of about $\frac{1}{1000}$ of these sizes. Such beads typically contain about 64% $ZrO_2$, about 33% $SiO_2$, about 2% MgO, and about 1% $Al_2O_3$. Other beads such as those made from melted droplets may not be fully solid and may contain air pockets rendering them more fragile and more readily broken or fragmented on impact. In a rapid solidification process, a hard microstructure consisting of zirconia and amorphous silica can produce lower density beads that are less wear resistant and more readily broken on impact. Other compositions of milling media bodies can have similar or analogous physical structures, i.e. they can contain pores and voids and air pockets. A range in wear resistance values, friabilities, fracture toughnesses, hardnesses, and brittleness index values can be obtained.

In one embodiment, milling media bodies in the form of spherical and non-spherical shapes are expected to be useful in the practice of this invention. Non-spherical shapes include cylindrical and torroidal shapes as well as elipsoids, cubes, and irregular shapes. Combinations of grinding media with different shapes are contemplated to be advantageous. For example, grinding media of a first material can comprise torroidal grinding media and/or spherical beads and/or cylinders and be used in conjunction with milling media bodies of a second material that can be spherical, cylindrical, or torroidal shaped or combinations of different shapes. Preferably, the milling media bodies of the second material are spherical in shape.

Depending on the relative hardness and toughness of the media and the relative hardness and toughness of the substrate to be milled, the surfaces of the media of the first material and of the media of the second material can both be smooth or they can both be roughened or ridged or one can be smooth and the other can be roughened or ridged. When a solid is substantially less tough and more brittle than the milling media bodies of the first material, said milling media bodies can be roughened or ridged or can be smooth, and milling media bodies of the second material can be roughened or ridged or smooth or non-porous. Relatively smooth, relatively hard, and relatively tough milling media bodies are preferred for second milling media material.

For a mixture of milling media bodies of a first material and milling media bodies of a second material where the first material and the second material are of substantially identical composition (such as two types of silica milling media, e.g., amorphous silica and hardened silica or two sizes of amorphous silica materials), the less tough media will be spalled by the more tough media. Smooth media can be tougher and less readily spalled than roughened media of the same chemical composition. Milling bodies of a first material can be roughened or porous and can be less tough than milling bodies of a second material when the materials are chemically similar or identical and milling bodies of the second material are smooth and non-porous.

Milling media bodies may be natural or synthetic, and in one aspect may be chosen from among the mineral salts and/or oxides containing at least one metallic element. Examples of mineral milling media materials include the alkaline earth carbonates such as calcium carbonate; marble; magnesium carbonate; zinc carbonate; dolomite; lime; magnesia; barium sulfate, calcium sulfate; aluminum hydroxides, silica, argils, and other silico-aluminous materials such as kaolin, talc, and mica; metal oxides such as zinc oxide, iron oxides, titanium oxides; glass fibers and glass microspheres; and wollastonite. Examples of organic materials of natural or synthetic origin include colorants, starch, cellulose fibers and granules, and carbon fibers.

Grinding media bodies comprising polymeric resins are suitable for use in this invention for media of either the first type or of the second type of material. Preferably, for media bodies of a second material such resins can be chemically and physically inert, substantially free of metals, solvent and monomers, and of sufficient hardness and fracture toughness to enable them to avoid being chipped or crushed during grinding.

Suitable polymeric resins include crosslinked polystyrenes, such as polystyrene crosslinked with divinylbenzene and/or trivinylbenzene, styrene copolymers, polyacrylates such as polymethyl methylcrylate, polycarbonates, polyacetals, such as Delrin™, vinyl chloride polymers and copolymers, polyurethanes, polyamides, poly(tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like.

In another aspect, the grinding media bodies can comprise an ion exchange resin. Suitable ion exchange resins include crosslinked polymeric resins containing cationic or anionic groups bound to the resin, especially at the surface of the resin. Preferred ion exchange resins for use in this invention are not substantially swollen by the fluid carrier or other components of the premix so that they remain hard and tough and capable of spalling the solid substrate in the milling process. Suitable ion exchange resins comprise polystyrene crosslinked throughout with from about 3 to about 20% by weight of a crosslinking agent such as divinylbenzene, trivinylbenzene, ethyleneglycol dimethacrylate, and the like, and surface-modified such as by chloromethylation and then quaternization with an amine such as trimethylamine, a tertiary amine, to form a quaternary ammonium-surface-modified, non-swelling, tough, hard ion exchange resin capable of binding anions and capable of spalling the solid substrate in the milling process, or such as by sulfonation with chlorosulfonic acid followed by treatment with a base such as sodium hydroxide to form a sulfonate-surface-modified, non-swelling, tough, hard ion exchange resin capable of binding cations and capable of spalling the solid substrate in the milling process. Such ion exchange resins as milling media bodies can both mill solid substrate and exchange ions that may be present or encountered in subsequent use of the syergetic comixture or that may be generated for example by fragmentation and leaching from other milling media bodies in the milling process or that may be subsequently encountered in a formulation or product derived from or comprising the mixture of milled substrate particles and particulates of ion exchange resin milling media. By way of illustration, the substrate may comprise a water insoluble drug and the milling media bodies of the first material may be a positively charged ion exchange resin. In an oral dosage form of the synergetic commixture of small particles of drug and particulates of the ion exchange resin, the ion exchange resin can adsorb anionic components encountered in the gastrointestinal system such as anionic bile acid salts that may interfere with or that may accelerate the bioavailability of the drug. The positively charged ion exchange resin is also capable of generating a high local concentration of anions proximal to the resin, and this high concentration of anions can be useful in hydrolytic cleavage of prodrugs comprising amides, esters, and the like. Positively charged ion exchange milling media particulates can also bind negatively charged drugs or negatively charged drugs generated from prodrugs and alter the bioavailability such as by prolonging or delaying release of the drug in a dosage form, modulating a bolus effect or delaying or controlling release of the drug into the body of a patient undergoing treatment or diagnosis with the drug.

In one aspect, particulates of ion exchange milling media bodies can have a fracture toughness lower and be more easily eroded or spalled than milling media bodies of a second material such as a yttrium-containing zirconium silicate ceramic bead material, and being less tough than the ceramic can be spalled at least in part to form particulates of a synergetic commixture with particles of solid substrate formed in the milling process of this invention. Ion exchange milling media bodies of a size larger than a desired size of particles of milled solid can be removed from a dispersion of particles and particulates formed in the milling process by a filtration or separation method.

In another aspect, as a second milling material in this invention, ion exchange media can have a fracture toughness larger than and be less brittle and less easily eroded than that of a first milling media material such as a colloidal silica or a calcium carbonate. The harder and tougher ion exchange media can spall the less tough and more easily eroded milling media material and also remove by ion exchange undesireable metal ions such as heavy metal ions, for example lead or yttrium that can be present or be generated in the milling process. The larger milling media bodies can then be removed from a dispersion of a synergetic commixture by a size separation method such as a filtration or sieving or other separation method.

Another useful feature of ion exchange resin milling media bodies in the process of this invention is their capacity to act as acids or bases in the milling process. As such, they are capable of initiating or catalyzing acid or base sensitive reactions such as condensation reactions, polymerization reactions, elimination reactions, precipitation reactions, hydrolysis reactions, esterification reactions, and the like. Ion exchange resin milling media bodies in this embodiment can comprise milling media bodies of a first material or milling media bodies of a second material or a mixture of both.

In another aspect, the polymeric material of which grinding or milling media bodies are comprised, and especially grinding media of a first material of this invention, can be biodegradable. The milling media bodies can comprise a single biodegradable polymer or a composite or mixture of two or more biodegradable polymers. Exemplary biodegradable polymers include poly(lactides), poly(glycolide) copolymers of lactides and glycolide, polyanhydrides, poly(hydroxyethyl methacrylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). When milling media bodies of a first material comprise biodegradable polymeric materials, the particulates of milling media bodies produced in the milling process of this invention are biodegradable as a component of the synergetic commixture.

Particulates of milling media bodies of biodegradable polymers advantageously can metabolize in vivo into biologically acceptable products which can be eliminated from the body of a mammal. In one aspect, biodegradable milling media bodies are preferred in the milling of solid substrates such as pharmaceuticals, ingredients in pharmaceutical formulations such as excipients, food additives, ingredients in food such as colorants, vitamins, mineral additives, and cosmetic ingredients including those used in cosmetics applied to the lips, eyes, and skin, including sunscreen formulations and cosmetic and decorative skin paints.

In yet another aspect, the material of which grinding media are comprised, and especially grinding media of a first material of this invention, can be biocompatible. When milling media bodies of a first material comprise biocompatible polymeric materials such as single biocompatible polymeric material or a composite of two or more biocompatible materials, the particulates of milling media bodies produced in the milling process of this invention are biocompatible as a component of the synergetic commixture. Exemplary biocompatible materials include biodegradable polymers as well as pharmaceutically acceptable excipient materials such as titanium dioxide, magnesium oxide, shellac, silicon dioxide, starch, povidone, sugar spheres, crosslinked sugar spheres, and certain waxes which can for example form physiologically tolerable compositions and formulations with pharmaceutical agents such as drugs and diagnostic imaging agents. Degradation of grinding media comprised in whole or in part of one or more than one acceptable excipient material can provide a source of such excipient material into a formulation of, for example a drug, a food material, or a cosmetic. Formulations of drugs can be administered by pharmaceutically acceptable means such as by oral, injectable, transmucosal, transdermal, and other means. In this regard, augmentation of a formulation by degraded media is useful and acceptable as a means to introduce excipients into a pharmaceutical formulation. Characteristics of these and other acceptable excipient materials are listed in "The Handbook of Pharmaceutical Excipients," $2^{nd}$ Edition, Edited by Wade and Weller, The Pharmaceutical Press, London, 1994, which is hereby incorporated by reference.

A polymeric milling media resin can have a density from 0.8 to about 3 $g/cm^3$. Higher density resins are preferred because they can provide more efficient particle size reduction. The use of polymeric resins can also enable improved pH control, for example when they can act as buffer materials with a broad pKa range or as a source of $H^+$ or $OH^-$ ions. Harder and tougher milling media bodies can be used to degrade less tough, more brittle and more easily spalled polymeric milling media bodies to form particulates of polymeric milling media. When the polymeric milling media bodies are biocompatible or biodegradable, the particulates of polymeric milling media bodies are also biocompatible or biodegradable.

Various inorganic grinding media prepared in the appropriate particle size are suitable for use in this invention. Such media include zirconium oxide, such as 95% ZrO stabilized with magnesia, zirconium silicate, glass, stainless steel, titania, alumina, and 95% ZrO stabilized with yttrium. Other media materials can be found in Tables 1, 2, 3, and 4.

While the size of the milling media bodies can range up to about 1000 times the desired size of the particles of milled substrate, in one aspect milling media bodies of a first material of this invention can range in size up to about 2000 micrometers. However, it is particularly advantageous that the invention enables the use of grinding media having a particle size of less than about 350 micrometers. More preferably, the media is less than about 100 micrometers, and, most preferably, less than about 75 micrometers, in size. This is especially true in the milling of drugs, photographic materials, semi-conductor materials and precursors, and other substances where a very small particle size is desired.

In one embodiment, milling media bodies of a second material of this invention can comprise particles, preferably substantially spherical in shape, e.g., beads, consisting essentially of a polymeric resin. Alternatively, the milling media bodies of a second material of this invention can comprise particles comprising a core having a coating of the polymeric resin adhered thereon.

A preferred method of making polymeric beads and torroidal grinding media, especially large size torroidal grinding media, is by polymerization of acrylic and vinylbenzene or styrenyl monomers such as styrene, divinylbenzene, and trivinyl benzene. Methyl methacrylate and styrene are preferred monomers because they are inexpensive, commercially available materials which make acceptable polymeric grinding media. Other acrylic and styrenic monomers are also known to work in grinding media. Styrene is preferred. However, free radical addition polymerization in general, and suspension polymerization in particular, can not be carried to 100% completion. Residual monomers can remain in the beads and torroids and can leach out during the milling process and contaminate the product dispersion unless removed, for example by leaching or by steam distillation.

Removal of the residual monomers can be accomplished by any number of methods common to polymer synthesis such as thermal drying, stripping by inert gases such as air or nitrogen, solvent or soxhelet extraction, steam distillation using beads suspended in a boiling aqueous medium or a boiling azeotrope-forming liquid, and the like. Drying and stripping processes are limited by the low vapor pressure of the residual monomers and large bead sizes resulting in long diffusion paths. Solvent extraction is therefore preferred. Any solvent can be used such as acetone, toluene, alcohols such as methanol, alkanes such as hexane, supercritical carbon dioxide and the like as long as the solvent or solvents also can be removed in a subsequent drying step and as long as any trace residual solvent is compatible with the extraction process and with the final product use. Acetone is preferred for crosslinked styrene beads. Solvents, which are effective in removing residual monomers, typically dissolve non-crosslinked polymer made from the monomer, or otherwise make the polymer sticky and difficult to handle. Therefore, it is preferred to crosslink the polymer and make it insoluble in the solvent which has an affinity for the monomer.

Only enough crosslinker to make the polymer insoluble, typically a few percent, is required but any amount can be used as long as the bead performs adequately as a grinding media. Commercially available divinylbenzene (usually containing about 55% divinylbenzene) is known to make beads which break up under milling conditions. This material can be useful in the preparation of milling media bodies of a first material comprising crosslinked polymer where high levels can lead to beads that are brittle and easily spalled. For example, copolymers of divinyl benzene with substituted styrenes such as chloromethylstyrene can be reacted with nucleophiles such as with amines such as secondary or tertiary amines to form tertiary amines and cationic (i.e., quaternary ammonium) crosslinked milling media beads, respectively, which can spall under the milling conditions of this invention. Chloromethyl-substituted styrenes are known to react with a number of nucleophiles such as with primary and secondary amines to provide aminomethyl-substituted styrenes; and with tertiary amines to provide quaternary ammonium chloride substituted styrenes, which chlorides can be converted by ion exchange to other salts such as hydroxide, sulfate, nitrate, phosphate, carboxylate, drug-containing anionic species, and other anionic salts of the quaternary ammonium polymer; with thiols or sulhydryls or sulfide anions to form sulfide or thio-ether substituted styrenes. Chloromethyl groups can be converted by chemical reactions to other functional groups on the resin, such as hydroxymethyl groups, aldehyde groups, ethers, carboxylic acids, and carboxylate-substituted groups, methylene phosphate groups, sulfanatomethyl groups, methylene sulfate groups, methylene hydroxylamine groups, and the like by well known methods in synthetic polymer chemistry. As subsequently spalled milling media particulates, the particulates contain these functional groups. The particulates can form a commixture, i.e., a commixture of particulates of the first material with the particles of solid substrate produced in the process of this invention.

Particulates of tertiary amine and quaternary ammonium ion-containing beads can act in many ways in a synergetic comixture. For example, they can act as ion exchange materials; as catalysts such as when they contain hydroxyl counterions for base catalyzed reactions such as hydrolysis of amides and esters; as adsorbants and/or mordants, for example as mordants for anionic materials such as dyes including infrared laser dyes, metal chelated dyes, anionic metal chelated dyes, brighteners such as fabric brighteners that can be used, for example, in soap or detergent formulations; as adsorbants for silicates and other anionic inorganic ions; as antibacterial or antifungal agents that can induce cytotoxic events such as cell wall rupture in bacteria and fungi; as binding agents for cells such as binding agents that can optionally separate blood cells from plasma, for example in a diagnostic procedure; as surface modifying agents that can control or modulate or modify the rate of penetration of water or other fluids such as gastrointestinal fluids into a formulation of a drug; and other ways such as chemically releasing amine or hydroxylamine under base catalysis or nucleophilic displacement or pyrolytic cleavage or oxidative elimination, for example via an N-oxide followed by pyrolysis. Particulates containing phenolic components such as vicinally t-butyl-substituted or alkyl-substituted hydroxybenzene materials or tetramethylpiperidinyl substituted derivatives can act as antioxidant components in a synergetic commixture of this invention, especially when the particles are drug, food, or cosmetic materials. For crosslinked polymeric milling media, any monomer with more than one ethylenically unsaturated group can be used such as divinylbenzene and ethylene glycol dimethacrylate. Divinylbenzene is preferred and a copolymer of 20% styrene, 80% commercial divinylbenzene (55% divinylbenzene) is especially preferred. Such polymers can also be sulfonated or oxidized to hydroxyl containing materials (e.g., to polymer bound phenolic materials). Anionic resin milling media body particulates can be useful in a synergetic commixture where they can bind cationic materials such as metal ions to control or modify their concentration or scavenge them, bind cationic dyes to provide color or light absorption or fluorescent emission, bind cationic drug materials for controlled or modified release and bioavailability. They can also provide nucleation sites such as in electroless plating of a metal onto a surface, which metal plated surface can subsequently act as a catalyst such as a hydrogenation or oxidation catalyst. They can also provide sites for binding of radionuclides useful in imaging and therapy of disease such as cancer.

To make spherical polymeric beads, suspension polymerization is preferred. To make large torroidal grinding media, large bead particles such as spherical particles can be individually milled or drilled into the shape of a torroid. Alternatively, a liner rod of a polymer prepared by extrusion of a bulk polymer through an orifice or hole in a die can be cut to size, softened by heating, and looped into the form of a torroid and then cooled. Optionally, the polymer in the loop can contain crosslinkable sites such as residual olefinic sites that can be irradiated with light to further crosslink and harden the large torroidal or bead milling media. Additionally, the polymer in the torroid can be swollen with a crosslinkable monomer such as divinylbenzene and trivinylbenzene, optionally together with an initiator such as a radical initiator, and then irradiated or heated to activate a crosslinking reaction that will essentially fix the shape of the torroid and prevent it from changing shape substantially from that of a torroid during use.

Another method useful to produce torroidal milling media bodies is to thermally extrude a polymer such as polystyrene from a die to form an extruded polymer in the form of a tube and then cut or slice the tube into torroid shapes that can be cooled to provide torroidal milling media. These polystyrene tubes can then be further treated with for example additional monomers such as styrene and crosslinking monomers that can coat the surfaces of the torroid and then be polymerized and crosslinked to provide torroids that are suitable for use as milling media. Media containing voids are expected to be less tough and more easily spalled than similar media without voids.

The size of the torroid can depend on the method of its production. For example, if derived from a polymer in the form of a tube that is sliced into torroids, the thickness of the tube wall, the width of the slice of the tube and the external and internal diameters dictate the dimensions of the torroid. Tubing with an external diameter that is from 1.1 to about 100 times the internal diameter can be used to produce torroids. Slice thickness can be from 0.1 to about 20 times the external diameter of the tube to form a useful torroid. Tubing cut larger than about 20 times the external diameter can be used, but such shapes can then be called hollow cylinders. These shapes will also be useful as milling media bodies in this invention.

Optionally, the tubing can be unsymmetrically stretched or distorted to form other than a right circular torroid or cylindrical shape for example by heating to soften the torroid and then pulling the walls of the torroid in two opposite directions to provide an oval distortion that is maintained on cooling. The distorted torrid can then be cooled and further crosslinked as above to provide large size grinding media useful in this invention. The tubing can optionally be filled with a second material such as a biodegradable or biocompatible polymer, for example by coextrusion of the polymers. Alternatively, rods of polymers can be used in the same procedure to form torroidal milling media.

The invention can be practiced in conjunction with various inorganic milling media bodies prepared in the appropriate particle size. Such media include zirconium oxide, such as 95% zirconium oxide stabilized with magnesia, zirconium silicate, glass, stainless steel, titania, alumina, and 95% zirconium oxide stabilized with yttrium. Inorganic milling media bodies can serve as core material when formed into shapes such as spheres and torroids and can be coated with polymer such as crosslinked polystyrene or crosslinked polymethylmethacrylate or a biocompatible polymer.

The core material preferably can be selected from materials known to be useful as grinding media when fabricated as spheres or particles. Suitable core materials include zirconium oxides (such as 95% zirconium oxide stabilized with magnesia or yttrium), zirconium silicate, glass, stainless steel, titania, alumina, ferrite and the like. Preferred core materials especially in milling media bodies of a second material of this invention have a density greater than about 2.5 g/cm$^3$. The selection of high density core materials is believed to facilitate efficient particle size reduction.

Useful thicknesses of the polymer coating on the core are believed to range from about 1 to about 500 micrometers, although other thicknesses outside this range may be useful in some applications. The thickness of the polymer coating preferably is less than the diameter of the core.

The cores can be coated with the polymeric resin by techniques known in the art. Suitable techniques include spray coating, fluidized bed coating, and melt coating as well as coextrusion of polymer cores and coatings. Adhesion promoting or tie layers can optionally be provided to improve the adhesion between the core material and the resin coating. The adhesion of the polymer coating to the core material can be enhanced by treating the core material to adhesion promoting procedures, such as roughening of the core surface, corona discharge treatment, and the like. Milling media bodies comprising biocompatible polymer can be roughened or ridged or made porous such as by leaching or by compounding with soluble inorganic salts or soluble organic compounds then forming beads from the compounded polymer, and then leaching the soluble material to leave pores in the beads. Alternatively, the soluble material can be left in the beads. Beads containing pores or beads comprising a composite of biocompatible polymer and soluble substance such as a salt or organic compound or soluble polymer can be used as milling media bodies of the first material in this invention when such material is less tough and more readily spalled than milling media bodies of the second material.

When the fluid carrier is a liquid, the milling process can be described as a wet milling process. When the fluid carrier is a gas, the milling process can be described as a dry milling process. In the case of dry milling where the fluid carrier is a gas such as an inert or non-reactive gas or a reactive gas or a mixture of such gases, the substrates must be capable of being formed into solid particles in the presence of two or more milling media materials. Reactive gases will react with ions or radicals formed in the milling of substrates. Reactive gases include oxygen as an oxidizing gas, air which contains oxygen, air enriched with additional oxygen or air partially depleted of oxygen, hydrogen as a reducing gas, olefinic and unsaturated gases such as ethylene and propylene, and carbon dioxide which can react in water to form carbonic acid and with base to form carbonate, a chlorofluorocarbon gas such as chlorotrifluoromethane which can react to transfer chlorine to the substrate, and dimethyl ether which can react to transfer hydrogen to the substrate. Preferred reactive gases as fluid carriers include air and carbon dioxide. Non-reactive gases are gases that will not readily react as oxidizing or reducing agents in the presence of ions or radicals formed in the milling of substrates. Non-reactive gases include air depleted of oxygen, nitrogen, argon which is an inert gas, helium, xenon, a perfluorocarbon gas such as perfluorpropane, a saturated hydrocarbon gas such as a normal hydrocarbon gas such as propane, and mixtures of these gases. Preferred non-reactive gases are nitrogen and air depleted of oxygen. A preferred inert gas is argon.

In the case of a wet milling process where the fluid carrier is a liquid, the substrates must be poorly soluble and dispersible in at least one liquid medium. The choice of fluid can depend primarily on the solid substrate and also on the composition of the milling media. A liquid fluid carrier should not be a good solvent for the solid being milled or the milling media. A wide variety of liquids can be used in a wet milling process of this invention, and the choice of fluid can be dictated by cost, ease of recovery, compatibility with components in the milling process, toxicity concerns, safety concerns, end use residual solvent concerns, and the like. For poorly water soluble solids such as poorly water soluble drugs, useful liquid fluid carriers include water, sterile water, water for injection, aqueous solutions of one or more salts such as PBS, solutions of aqueous buffers, aqueous phosphate buffered saline, buffered aqueous solutions, aqueous solutions containing proteins such as albumin, sugar-containing water, aqueous solutions of one or more pharmaceutical excipients as described herein including aqueous solutions of gelatin, aqueous solutions of one or more carbohydrates and aqueous solutions of one or more polymers such as PEG and poly(ethylene oxide) and poly (ethylene oxide) esters and poly(ethylene oxide) ethers as well as PVP and polyvinylpyrrolidone, aqueous solutions of carbohydrates such as those comprising from 1% to 25% of one or more carbohydrates, aqueous solutions of one or more than one surface active substance, liquid surface active substances, aqueous solutions of one or more surface active substances mixed with one or more undissolved surface active substances that may be a liquid, and compatible mixtures thereof. Additionally, the invention can be practiced with other liquid media. Other useful fluid carriers include ethanol, methanol, butanol, hexane, hydrocarbons, kerosene, PEG-containing water, glycol, toluene, xylene, glyme, petroleum-based solvents, ligroin, mixtures of aromatic solvents such as xylenes and toluene, heptane, mixtures of water miscible solvents and water, DMSO, DMF, glycerol, liquid paraffin, petroleum distillates, fish oils, vegetable oils, mixtures of solvents such as those listed herein, and the like.

By "poorly soluble" it is meant that the substrate has a solubility in the liquid dispersion medium, e.g., water, of less than about 10 mg/ml, and preferably of less than about 1 mg/ml. A preferred liquid dispersion medium is selected from the group consisting of water, a solution of one or more salt in water, a solution of one or more sugar in water, a solution of one or more surface active agent optionally in the presence of excess surface active agent in water, a solution of a polymer in water, and combinations thereof. In this regard, preferred salts are sodium chloride and phosphoric acid salts.

In one aspect where pharmaceutical agents are substrates in the invention, preferred liquid carriers include water, sterile water, water for injection, aqueous salt solutions such as PBS, aqueous buffer solutions, aqueous solutions containing proteins such as albumin, aqueous phosphate buffered saline, buffered aqueous solutions, sugar-containing water, aqueous solutions of one or more pharmaceutical excipients including pharmaceutically acceptable salts, buffers, gelatin, carbohydrates and polymers, aqueous solutions of carbohydrates such as those comprising from 1% to 50% of one or more carbohydrates (preferably 1% to 30% of one or more carbohydrates), aqueous solutions of one or more than one surface active substance, aqueous solutions of one or more surface active substances mixed with one or more undissolved surface active substances that may be a liquid such as a surface active substance that melts at a temperature below the temperature used in the process of this invention, PEG-containing water, ethanol, and mixtures of these liquid carriers.

Wet grinding can be accomplished in conjunction with a liquid fluid carrier and one or more than one surface active substance. Useful liquid fluid carriers include water, aqueous salt solutions, aqueous sugar solutions, aqueous polymer solutions such as polyalkyleneoxide solutions, ethanol, butanol, hexane, glycol and the like. The surface active substance can be selected from known organic and inorganic pharmaceutical excipients and can be present in an amount of 0.1–90%, preferably 1–80% by weight based on the total weight of the dry substrate. Preferred surface active substances are phospholipids and lecithins.

In another aspect, the fluid carrier can be a single component or mixture or solution of one or more liquefied or compressed gas or subcritical or supercritical fluid such as liquefied compressed nitrogen or argon, or the fluid carrier can be a gas maintained under pressure in the form of a subcritical or supercritical fluid. Many types of milling media bodies can become more brittle and more easily shattered and fractured and spalled at low temperatures such as at liquid nitrogen or liquid ammonia temperatures. Examples of supercritical fluids include supercritical carbon dioxide, supercritical dimethyl ether, supercritical hydrocarbons such as supercritical methane, supercritical ethane, and supercritical propane and mixtures of supercritical fluids. The fluid carrier can also comprise a subcritical or supercritical fluid containing one or more dissolved materials such as one or more excipients, one or more surface active substances, and the like. The fluid carrier can also comprise a solution of a solvent in a subcritical or supercritical fluid or a solution of a supercritical fluid in a solvent. Solutions of such materials and solutions of mixtures of such materials can range from about 0.01% by weight of fluid up to the saturation point of the solubility of the materials in a supercritical fluid being employed according to this invention. Preferred concentrations of surface active substance material in a supercritical fluid range from about 0.01% up to about 10% when such solubilities can be achieved.

The solid substrate used in this invention can comprise any crystalline or amorphous solid material that can be milled in a media mill as well as mixtures of two of more solids that can be milled in a media mill. The premix generally consists of a solid substrate to be milled in the form of a powder, a glass, an amorphous or crystalline solid, a distribution of particles that can range in size from smaller than the desired size of the particles to the size of the entry port in the media mill. With respect to the milling process of this invention, the premix is generally a solid that may be a single crystalline form, a mixture of crystalline forms, an amorphous solid, or a mixture of solids to be milled. The size of at least some of the components of the solid is generally larger than the size of small particles produced in this invention, although the premix may contain a range of sizes including some very small particles that can form a dispersion in the fluid carrier. Such particles are, however, generally produced in the process of the invention by media milling and size reduction of the solid substrate in the premix. The solid substrate may be in the form of any shape that is suitable for milling and size reduction to form particles, especially very small particles. The premix may be a precipitated solid, a recrystallized solid, a partially milled solid such as a previously media milled solid, a jet milled solid, a partially ground solid, a micronized solid, a pulverized solid, a ball milled solid, a triturated solid, a sublimed solid, a residue from an evaporation, a solid derived from a synthetic process, a solid derived from an extract such as an organic solvent extraction or supercritical fluid extraction from a mixture such as reaction product or plant or tissue extract.

The substrates can be organic solids either crystalline or amorphous materials, or they may be inorganic solids as long as they can be reduced in size by the milling process. Organic solids can be single compounds or mixtures of compounds, enantiomers, optical isomers, racemic mixtures, diastereomers, isomers, blends, glasses, separate crystal forms of a single substance, eutectic mixtures, or formulations of different compounds such as a drug substance and a surface active substance.

Examples of a solid material include a solid pigment; a solid photographic material such as a solid dye; a solid cosmetic ingredient; a solid chemical such as a solid inorganic compound or a mixture of solid inorganic compounds such as carbonate salts or sulfate salts or oxides of metals or solid organic compounds such as crystalline organic compounds or a solid organic compound having from about 3 to about 100 carbon atoms or an enantiomer of such a compound; a solid metal powder; a solid catalyst material; a solid support material for a catalyst; a solid stationary phase or support material useful in analytical and preparative chromatography; a solid toner material, black or colored, useful in xerographic and printing applications including laser printing; a solid grinding material and a precursor to a grinding material, and a ceramic material such as can be used in sols and prior to sintering; an alloy; a metal; and a solid pharmaceutical agent such as a water soluble, water insoluble, or poorly water soluble therapeutic agent or diagnostic imaging agent, a medicinally active agent, a medicament, a plant or herbal extract, a drug, a pro-drug, a solid drug formulation, a diagnostic imaging agent, and the like. Preferred solid materials are pharmaceutical agents, and most preferred are poorly water-soluble and water-insoluble pharmaceutical agents.

Polymeric milling media particles can be prepared by known methods including suspension bead polymerization, latex polymerization, swelling of latex polymer particles with additional styrene or methacrylate monomers optionally including crosslinking monomers followed by polymerization, spray drying of solutions of polymers optionally followed by crosslinking, and other known methods used to prepare small particle milling media. Small particle milling media bodies can also comprise inorganic materials in their entirety or in part, the latter also comprising coatings of organic polymer prepared according to well known methods. When used as milling media bodies of a second material according to this invention, the milling media bodies are preferably spherical or bead shaped media.

Grinding or milling media bodies useful for milling include balls, cylinders and other shapes of steel, corundum, porcelain, steatite, alumina, mixed oxides and quartz such as those having a diameter of from 0.05 to 20 mm. The grinding media having a pore-free smooth surface are tougher and less easily spalled than grinding media having a porous surface or a rough surface of the same composition.

Milling temperatures can be controlled for optimum performance of the media mill and brittleness of the milled solid and milling media, which can become more elastic and resistant to particle size reduction at higher temperatures. Milling temperatures can range from as low as liquid air, liquid nitrogen, or liquid argon temperatures, but are more commonly from about −80° C. to about 300° C. For organic materials, the range is preferably from about −80° C. to about 250° C. Preferably the temperature is below the temperature of thermal degradation of the solid being milled. For pharmaceutical solids, the range is preferably from about −80° C. to about 180° C. Preferably the temperature is below the melting temperature of the solid being milled.

In preferred embodiments where the solid substrate is a pharmaceutical agent, the process can be carried out within a wide range of temperatures and pressures. The process preferably is carried out at a temperature below that which can cause the substrate to degrade. For many substrates, ambient temperatures are appropriate. Temperatures of less than about 30° C. to 40° C. are typically preferred. Control of the temperature, e.g., by jacketing or immersion of the milling chamber in cold water, ice water, liquid ammonia, liquid nitrogen, liquid ethylene glycol water mixtures or other antifreeze solutions, salt water, liquid sodium, a heated or cooled air bath, and by electrical resistance heating are contemplated. Processing pressures from about 1 psi up to about 500 psi are contemplated in most situations, although pressures as high as 500 bar can be encountered, for example in the presence of liquified gases, subcritical and supercritical fluids. Processing pressures from about 10 psi to about 300 psi are typical in most situations.

The duration of milling depends on the desired size or fineness of the solid being milled, and on its toughness and pulverulence and ease of fracture as well as on the milling media bodies being spalled. The residence time in the milling chamber in a media mill is usually between 1 and 100 hours, but longer times are sometimes needed. A duration of from I to 15 hours is advantageous, preferably from 2 to 8 hours.

The attrition time can vary widely and depends primarily upon the particular solid substrate in the premix which in preferred embodiments is a therapeutic or diagnostic agent to be milled, energy transfer efficiency in the media mill, mill residence conditions selected, the initial and desired final particle and particulate sizes, relative media size distributions, relative media fracture toughnesses, hardnesses, brittleness indexes, and so forth. Residence times of less than about ten hours are generally required using high energy media mills.

Hardness of milling media materials can be quantified according to several known standard test methods and related scales. For example, these include the Mohs, Vickers, Rockwell, and the Knoop hardness tests. Typical values for the relative hardness and fracture toughness of a selection of useful milling media materials are shown in Table 1. The materials listed in Table 1 are meant to be representative and non-limiting. Use of milling media bodies composed of materials not listed in Table 1 according to this invention is also contemplated. Harder and tougher milling media bodies will spall less tough milling media.

TABLE 1

Relative Hardness and Toughness Scales for Representative Milling Media

| Milling Media Material | Fracture Toughness $K_c$ MPa(m)$^{1/2}$ | Mohs Hardness (original) | Mohs Hardness (modified) | Vickers Scale $H_v$ Kg/mm$^2$ | Knoop Scale $H_K$ |
|---|---|---|---|---|---|
| Talc 3MgO.4SiO$_2$.H$_2$O | | 1 | 1 | | |
| Gypsum CaSO$_4$.2H$_2$O | | 2 | 2 | | 32 |
| Silver Ag | | | | | 60 |
| Zinc Zn | | | | | 119 |
| Calcite CaCO$_3$ | | 3 | 3 | | 135 |
| Fluorite CaF$_2$ | | 4 | 4 | | 163 |
| Copper Cu | | | | | 163 |
| Magnesia MgO | | | | | 370 |
| Apatite CaF$_2$.3Ca$_3$(PO$_4$)$_2$ | | 5 | 5 | | 430 |
| Pumice | | 5–6 | | | 430–560 |
| Soda Lime Glass | | | | | 530 |
| Nickel Ni | | | | | 557 |
| Orthoclase or Feldspar K$_2$O.Al$_2$O$_3$.6SiO$_2$ | | 6 | 6 | | 560 |
| Vitreous silica | | | 7 | | |
| Quartz SiO$_2$ | | 7 | 8 | 1100 | 820 |
| 125 μm SiO$_2$ | 1.37 | | | | |
| 600 μm SiO$_2$ | 1.60 | | | | |
| Zirconium Silicate ZrSiO$_4$ | | 7.7 | | 820–920 | |
| Flint | | 7 | | 900–1100 | 700–800 |
| Silicon | 3.0–6.0 | | | | 1150 |
| Emery | | 7–8 | | 1600 | 800–1800 |
| Topaz (AlF)$_2$SiO$_4$ | | 8 | 9 | | 1340 |
| Garnet Al$_2$O$_3$.3FeO.3SiO$_2$ | | 7–8 | 10 | 1100–1300 | 1300–1360 |
| Chromium Cr | | | | | 935 |
| Zirconia TZP | 7–13 | | | | 1300–1600 |
| Zirconia fused ZrO$_2$ | | | 11 | | 1160 |
| Zirconia PSZ | 12 | | | | 1120–1300 |
| Beryllia BeO | | | | | 1250 |
| Tungsten Carbide alloy WC, Co | | | | | 1400–1800 |
| Zirconium Boride ZrB$_2$ | | | | | 1550 |
| Zirconia toughened alumina ZTA | 5–7 | | | | 1750–2100 |
| Sialon | 5.5–7.5 | | | | 1600–1800 |
| Titanium Nitride TiN | | | 9 | | 1800 |
| Tungsten Carbide WC | | | | | 1880 |
| Tantalum Carbide TaC | | | | | 2000 |
| Zirconium Carbide ZrC | | | | | 2100 |
| Alumina fused Al$_2$O$_3$ | 2.5–3.36 | 9 | 12 | 2200 | 2000–2600 |
| Alumina (Al$_2$O$_3$)99.5% | 4.3 | | | | 2000 |
| Beryllium Carbide Be$_2$C | | | | | 2410 |
| Titanium Carbide TiC | | | | | 2470 |
| Silicon Carbide SiC | 3.52 | 9 | 13 | 2800–3300 | 2000–3700 |
| Corundum | | | 9 | | 2200 | 1600–2100 |
| Aluminum Boride AlB | | | | | 2500 |

TABLE 1-continued

Relative Hardness and Toughness Scales for Representative Milling Media

| Milling Media Material | Fracture Toughness $K_c$ MPa(m)$^{1/2}$ | Mohs Hardness (original) | Mohs Hardness (modified) | Vickers Scale $H_v$ Kg/mm$^2$ | Knoop Scale $H_K$ |
|---|---|---|---|---|---|
| Boron Carbide B$_4$C | 3.37 | 9–10 | 14 | 3300–4300 | 2200–5100 |
| Boron nitride - cubic BN | | 10 | | 7300–10000 | 4700–10000 |
| Diamond-natural C | | 10 | 15 | 10000 | 8000 |
| Diamond-synthetic C | | 10 | 15 | 10000 | 8000–10000 |

As illustrated in Table 1, fracture toughness, $K_C$, can range from 1.37 for silica to 13 for zirconia in MPa(m)$^{1/2}$. Mohs hardness (original) can range from 1 for talc to 10 for diamond, and Mohs hardness (modified) can range from 1 for talc to 15 for diamond. The range of the Knoop scale, $H_K$, runs from about 32 for gypsum to 10000 for diamond and boron nitride. Examples of milling media material include talc (3MgO.4SiO$_2$.H$_2$O), gypsum (CaSO$_4$.2H$_2$O), silver (Knoop scale 60), zinc (Knoop scale 119), calcite CaCO$_3$ (Knoop scale 135), fluorite CaF$_2$ (Knoop scale 163), copper (Knoop scale 163), magnesia (Knoop scale 370), apatite CaF$_2$.3Ca$_3$(PO$_4$)$_2$ (Knoop scale 430), pumice (Knoop scale 430 to 560), soda lime glass (Knoop scale 530), nickel (Knoop scale 557), orthoclase or feldspar K$_2$O.Al$_2$O$_3$.6SiO$_2$ (Knoop scale 560), vitreous silica, quartz (Knoop scale 820), 125 μm silica SiO$_2$ (fracture toughness 1.37), 600 μm silica SiO$_2$ (fracture toughness 1.60), zirconium silicate ZrSiO$_4$, flint (Knoop scale 700 to 800), silicon (Knoop scale 1150), emery (Knoop scale 800 to 1800), topaz (AlF)$_2$SiO$_4$ (Knoop scale 1340), garnet Al$_2$O$_3$.3FeO.3SiO$_2$ (Knoop scale1300 to 1360), chromium (Knoop scale 935), zirconia TZP (Knoop scale 1300 to 1600), fused zirconia ZrO2 (Knoop scale 1160), zirconia PSZ (Knoop scale 1120 to 1300), beryllia BeO(Knoop scale 1250), tungsten carbide alloy WC (Knoop scale 1400 to 1800), zirconium boride (Knoop scale 1550), zirconia toughened alumina (Knoop scale 1750 to 2100), sialon (Knoop scale 1600 to 1800), titanium nitride TiN (Knoop scale 1800), tungsten carbide (Knoop scale 1880), tantalum carbide (Knoop scale 2000), zirconium carbide ZrC (Knoop scale 2100), fused alumina Al$_2$O$_3$ (Knoop scale 2000 to 2600), alumina 99.5% Al$_2$O$_3$ (Knoop scale 2000), berylium carbide Be$_2$C (Knoop scale 2410), titanium carbide TiC (Knoop scale 2470), silicon carbide SiC (Knoop scale 2000 to 3700), corundum (Knoop scale 1600 to 2100), aluminum boride (Knoop scale 2500), boron carbide B$_4$C (Knoop scale 2200 to 5100), boron nitride BN (Knoop scale 4700 to 10000), natural diamond (Knoop scale 8000 to 10000.

Examples of additional materials that can be used in this invention are given in Table 3 together with fracture toughness and fracture energy measured according to the methods cited. The data were taken from the web site of the National Institute of Standards and Technology (NIST), Gaithersburg, Md., internet web site at http://www.ceramics.nist.gov/srd/summary/ftmain.htm.

Mohs hardness is a rough measure of the resistance of a smooth surface to scratching or abrasion, and is expressed as a relative scale devised in 1812 by mineralogist Friedrich Mohs. The Mohs hardness scale is composed of 10 minerals that have been given arbitrary hardness values. The Mohs hardness of a solid such as a mineral or composite material is determined by observing whether its surface is scratched by a substance of known or defined hardness. For example, if a mineral is scratched by orthoclase but not by apatite, its Mohs hardness is between 5 and 6. If the material being tested is fine-grained, friable, or pulverulent, the test may only loosen grains without testing individual surfaces. Certain textures or aggregate forms may hinder or prevent a true hardness determination. Thus the Mohs test is not generally suitable for accurately gauging the hardness of industrial milling materials such as, for example, steel or ceramics but a qualitative approximation can be made. Another disadvantage of the Mohs scale is that it is not linear. Each increment of one unit in the scale does not indicate a proportional increase in hardness. For instance, the progression from calcite to fluorite, or from 3 to 4 on the Mohs scale, reflects an increase in hardness of approximately 25 percent, while the progression from corundum to diamond, or from 9 to 10 on the Mohs scale, reflects a hardness increase of more than 300 percent. Milling media bodies composed of material that exhibit high Mohs hardness values with be harder than milling media bodies composed of material that exhibit lower Mohs hardness values.

The Vickers or diamond pyramid hardness test is a measure of the hardness of a material, calculated from the size of an impression produced under load by a pyramid-shaped diamond indenter. The Vickers hardness test was devised in the 1920s, and permitted the establishment of a continuous scale of comparable numbers that accurately reflected the wide range of hardness found in steels. The indenter often employed in the Vickers test is a square-based pyramid whose opposite sides meet at the apex at an angle of 136°. The diamond is pressed into the surface of the material at loads ranging up to approximately 120 kilograms-force, and the size of the impression is measured with the aid of a calibrated microscope. The Vickers test is considered to be reliable for measuring the relative hardness of metals, ceramic and other materials. The Vickers number, Hv, can be calculated using the following formula: $H_V=1.854(F/D^2)$, where F is the specified applied load measured in kilograms-force, and $D^2$ the area of the indentation measured in square millimeters. Harder milling media materials have higher Vickers hardness numbers than softer milling media materials.

Knoop hardness, devised in 1939, is calculated by measuring the indentation produced by a diamond tip that is pressed onto the surface of a sample. By using lower indentation pressures than the Vickers hardness test, the Knoop test allows the hardness testing of brittle materials such as glass and ceramics. The diamond indenter employed in the Knoop test is in the shape of an elongated four-sided pyramid, with the angle between two of the opposite faces being approximately 170° and the angle between the other two being 130°. Pressed into the material under loads that are often less than one kilogram-force, the indenter leaves a four-sided impression about 0.01 to 0.1 mm in size. The length of the impression is approximately seven times the width, and the depth is 1/30 the length. Given such dimensions, the area of the impression under load can be calculated after measuring only the length of the longest side with the aid of a calibrated microscope. The final Knoop hardness, $H_K$, can be derived from the following formula: $H_K=14.229(F/D^2)$, where F is the applied load measured in kilograms-force, and $D^2$ the area of the indentation measured in square millimeters. Knoop hardness numbers are often cited in conjunction with specific load values. Hardness values of milling media materials can be estimated using objects larger than the milling media bodies but of the same composition. However, when the milling media material is not of uniform composition such as a composite or alloy of two or more pure materials, hardness values of the composite or alloy may vary considerably from the values found for each of the pure materials.

Hardness is related to a material's resistance to deformation, densification, and fracture. It has sometimes been defined as the resistance of a material to plastic deformation by penetration or scratching. Hardness is a crucial property for wear and abrasion-resistant parts and milling media bodies when it is desired to have minimum to zero erosion of the media during a milling process.

A number of empirical and semi-empirical relationships between hardness and fracture toughness are known. In one aspect, hardness can be considered to be a measure of the resistance offered by a substance to displacement of its surface by abrasion, while fracture toughness can be considered to be a measure of the resistance offered by a substance to fracture under impact (see Hubbard P. and Jackson F. H., "Relation between the properties of hardness and toughness of road-building rock", J. Agricultural Research, Vol. V, No. 19, pp 903–907, 1916.) The average hardness of a material can increase with toughness, and the rate of increase can become less as the toughness values becomes larger. In a plot of hardness versus toughness values of a number of milling media materials, individual values of hardness can vary through wide limits for low values of toughness, and variations of hardness from an average value can decrease uniformly with an increase in toughness up to a certain point after which they can remain constant with very little variation from the average value.

A Vickers hardness tester measures Vickers hardness of surfaces and materials by indentation. Indentation also produces radial cracks in the surface of the test material, and properties of the cracks can be related to the fracture toughness of the material. Vickers hardness scales can be expressed in units such as GPa or kgf/mm$^2$ (where 1 GPa~102 kgf/mm$^2$). For example Vickers hardness of zirconia F 1973-98 has an ASTM specification of 11.8 Gpa-1200 kgf/mm$^2$ at a load of 9.8 N (1 kgf). Typically, an indenter tip, normal to a sample surface, with a known geometry is driven into the sample by applying an increasing load up to some preset value. The load is then gradually decreased until partial or complete relaxation of the sample has occurred. The load and displacement can be recorded continuously throughout this process to produce a load displacement curve in which the penetration depth of the indenter tip is an increasing function of the normal load force. Dynamic indentation is a technique used in nano-indentation, and hardness can be calculated from the maximum load divided by the area of contact after unloading. Hardness and Young's modulus can be calculated from the depth versus load curve using well established models. The fracture toughness of a material can be determined by directly measuring Vickers-produced radial cracks as a function of indentation load. The length of the cracks and the indentation half-diagonal size are related to the hardness, elastic modulus, and fracture toughness. At low indentation loads, problems can arise from load dependence of hardness and from measurement uncertainty due to small indentation size. At higher loads, cracking and spalling can occur. An indentation size effect can be observed in which hardness decreases with increasing indentation load. Hardness is inversely proportional to the square of the diagonal length of the indentation.

Within the context of brittle materials, indentation testing is commonly used for evaluating material toughness, i.e., relating the fracture resistance to the scale of the crack pattern. Although easily applicable to bulk materials, the method is also of importance in understanding the build-up of residual stresses in coated systems as a result of the deposition procedure. An equation relating fracture toughness, $K_c$, to post-indentation crack size, c, is given as $K_c = X(P/c^{3/2})$ where P is the applied indentation load and X is a constant which depends on the ratio of Young's modulus to hardness, E/H. Most brittle materials generate radial/median cracks which extend from the corners of the residual impression and downwards from the indenter apex.

Further with respect to the relationship between hardness and fracture toughness, a discrete transition point may be found in a plot of Vickers hardness ($H_V$) versus load or $H_V$ versus diagonal size in Vickers hardness/load curves. At the transition point, hardness changes from being load-dependent to a constant value. The transition point is associated with the onset of extensive cracking around and underneath the indentation. Cracking can be localized at relatively low load levels or cracking can be massive at higher loads to the extent that crushing ensues. The transition point can be related to an index of brittleness which is sometimes defined as $B_1 = HE/(K_{1c})^2$. The brittleness index can be important for predicting wear and erosion resistance in milling media bodies of this invention.

Another brittleness index parameter, B, given by the ratio of hardness to fracture toughness, has been proposed as a parameter for a qualitative assessment of the wear and erosion behavior of ceramic composites. For example, A. R. Boccaccini in "The relationship between wear behavior and brittleness index in engineering ceramics and dispersion-reinforced ceramic composites," Interceram (1999), 48(3), 176–187, herein incorporated by reference, reported a relationship between the wear abrasion and solid-particle erosion resistance and brittleness of engineering ceramics and dispersion reinforced ceramic composite materials. For $0.5 < B < \sim 5\text{-}6$ micrometers$^{-1/2}$, wear resistance increases with increasing B, and both plastic deformation and microfracture are active material-removal mechanisms. For $\sim 5\text{-}6 < B < 9$ micrometers$^{-1/2}$, wear resistance decreases with increasing B.

One aspect of the current invention, comprises a process for preparing a synergetic commixture comprising small particles of a solid substrate and small particulates of a first material of a desired size, said process comprising the steps of:

(a) providing to the milling chamber of a media mill a contents comprising a pre-mix of a solid substrate, a fluid carrier, a plurality of milling bodies of a first material, and a plurality of milling bodies of a second material;

(b) operating said media mill to grind said solid substrate and degrade at least a portion of said milling bodies of first material to produce a dispersion in said fluid carrier comprising a synergetic commixture of small particulates of said first material and small particles of said solid substrate having a desired size equal to or less than a size Sp;

(c) separating said dispersion from any residual milling body, piece of milling body, and solid substrate having a size larger than Sp; and (d) optionally removing said fluid carrier from said dispersion to form a dry synergetic commixture comprising said particles and said small particulates;

wherein, the milling bodies of said first material are fractured and eroded by the milling bodies of said second material, the milling bodies of said second material are essentially substantially resistant to fracture and erosion in the milling process, and Sp is smaller than the size of the milling bodies of the second material.

Furthermore, in one aspect of the current invention, the milling media bodies of a first material can have a brittleness index $B_{1L}$ and the milling media bodies of a second material can have a brittleness index $B_{2L}$, wherein $B_{1L}$ is less than $B_2L$, and $B_{1L}$ and $B_{2L}$ are less than about 5.5. In another aspect of the current invention, the milling media bodies of a first material can have a brittleness index $B_{1H}$ and the milling media bodies of a second material can have a brittleness index $B_{2H}$, wherein $B_{1H}$ is greater than $B_{2H}$ and both $B_{1H}$ and $B_{2H}$ are greater than about 5.5. In yet another aspect of the current invention the milling media bodies of a first material can have a hardness $H_1$ and the milling media bodies of a second material can have a hardness $H_2$, wherein $H_1$ is less than $H_2$.

Brittleness is a measure of the relative susceptibility of a material to deformation and fracture. It can correlate with hardness, which reflects the resistance to deformation in a material, and it can correlate with fracture toughness, which reflects the resistance to fracture in a material. B is known to vary widely, for example B is about 0.1 $\mu m^{-1/2}$ for steels, about from 2 $\mu m^{-1/2}$ to about 9 $\mu m^{-1/2}$ for ceramics, and about 17 $\mu m^{-1/2}$ for mono-crystalline silicon. Table 2 lists brittleness index values, B, for some representative materials that can be used as milling media. Brittleness index values range from 0.91 for magnesium to 15.14 for silicon. Representative materials and respective brittleness index values in brackets include magnesium—PSZ (0.91), soda-lime glass (1.18), magnesium—PSZ (1.40), sintered SiAlON (1.52), fused silica (1.61), glass ceramic (1.69), HP $Al_2O_3$ (1.98), $Si_3N_4$+TiC/TiN (2.00), $Si_3N_4$+TiC/TiN (2.13), $Si_3N_4$ beta (2.20), Sintered $B_4C$ (2.47), $Si_3N_4$ alpha (2.50), SiAlON (2.68), $Si_3N_4$+10 vol % SiC (2.91), $Si_3N_4$+30 vol % SiC (2.91), $Al_2O_3$+$ZrO_2$ (2.96), flint (2.96), $Al_2O_3$ beta (3.00), MgO (3.08), MgO (3.18), $Si_3$N4+20 vol % SiC (3.19), $Si_3$N4 (3.20), sintered $TiO_2$ (3.29), $Al_2O_3$+$ZrO_2$ (3.33), $Si_3$N4+30 vol % SiC (3.38) HP $Si_3N_4$ (3.38), $Si_3N_4$+ 10 vol % TiC (3.49), $Al_2O_3$ (3.62), $Si_3N_4$+20 vol % TiC (3.66), beta SiAlON (3.73), $Al_2O_3$ (3.77), $Si_3N_4$+10 vol % TiC (3.95), $Al_2O_3$—$Zro_2$ (4.12), $Al_2O_3$ (4.20), $Si_3N_4$+20 vol % TiC (4.20), $Si_3N_4$+30 vol % TiC (4.22), $Si_3N_4$+10 vol % SiC (4.22), alpha $SiAlON_9$ (4.29), $Al_2O_3$+$ZrO_2$+TiC/TiN (4.29), $Si_3N_4$+40 vol % TiC (4.36), $Si_3N_4$+20 vol % SiC (4.54), $Si_3N_4$+30 vol % TiC (4.97), $Al_2O_3$ alpha (5.43), $Si_3N_4$+40 vol % TiC (5.43), HP $Al_2O_3$ (5.50), $ZrO_2$ (5.76), $Al_2O_3$ (6.00), SiC beta (6.19), SiC—$TiB_2$ (6.74), HP SiC (7.35), $B_4C$ (8.33), soda lime silica glass (8.40), SiC alpha (8.54), spinel (9.41), sintered $Al_2O_3$ (9.86), sapphire (9.86), silica glass (11.30), and silicon (15.14).

TABLE 2

Brittleness Index Data of Representative Materials Useful as Milling Media

| Material | Brittleness Index, ($\mu m^{-1/2}$) |
|---|---|
| Mg - PSZ | 0.91 |
| Soda-lime glass | 1.18 |
| Mg - PSZ | 1.40 |
| Sintered SiAlON | 1.52 |
| Fused silica | 1.61 |
| Glass - ceramic | 1.69 |
| HP $Al_2O_3$ | 1.98 |
| $Si_3N_4$ + TiC/TiN | 2.00 |
| $Si_3N_4$ + TiC/TiN | 2.13 |
| $Si_3N_4$ beta | 2.20 |
| Sintered $B_4C$ | 2.47 |

TABLE 2-continued

Brittleness Index Data of Representative Materials Useful as Milling Media

| Material | Brittleness Index, ($\mu m^{-1/2}$) |
|---|---|
| $Si_3N_4$ alpha | 2.50 |
| SiAlON | 2.68 |
| $Si_3N_4$ + 10 vol % SiC | 2.91 |
| $Si_3N_4$ + 30 vol % SiC | 2.91 |
| $Al_2O_3$ + $ZrO_2$ | 2.96 |
| Flint | 2.96 |
| $Al_2O_3$ beta | 3.00 |
| MgO | 3.08 |
| MgO | 3.18 |
| $Si_3N_4$ + 20 vol % SiC | 3.19 |
| $Si_3N_4$ | 3.20 |
| Sintered $TiO_2$ | 3.29 |
| $Al_2O_3$ + $ZrO_2$ | 3.33 |
| $Si_3N_4$ + 30 vol % SiC | 3.38 |
| HP $Si_3N_4$ | 3.38 |
| $Si_3N_4$ + 10 vol % TiC | 3.49 |
| $Al_2O_3$ | 3.62 |
| $Si_3N_4$ + 20 vol % TiC | 3.66 |
| Beta SiAlON | 3.73 |
| $Al_2O_3$ | 3.77 |
| $Si_3N_4$ + 10 vol % TiC | 3.95 |
| $Al_2O_3$ - $ZrO_2$ | 4.12 |
| $Al_2O_3$ | 4.20 |
| $Si_3N_4$ + 20 vol % TiC | 4.20 |
| $Si_3N_4$ + 30 vol % TiC | 4.22 |
| $Si_3N_4$ + 10 vol % SiC | 4.22 |
| Alpha SiAlON | 4.29 |
| $Al_2O_3$ + $ZrO_2$ + TiC/TiN | 4.29 |
| $Si_3N_4$ + 40 vol % TiC | 4.36 |
| $Si_3N_4$ + 20 vol % SiC | 4.54 |
| $Si_3N_4$ + 30 vol % TiC | 4.97 |
| $Al_2O_3$ alpha | 5.43 |
| $Si_3N_4$ + 40 vol % TiC | 5.43 |
| HP $Al_2O_3$ | 5.50 |
| $ZrO_2$ | 5.76 |
| $Al_2O_3$ | 6.00 |
| SiC beta | 6.19 |
| SiC – $TiB_2$ | 6.74 |
| HP SiC | 7.35 |
| $B_4C$ | 8.33 |
| Soda lime silica glass | 8.40 |
| SiC alpha | 8.54 |
| Spinel | 9.41 |
| Sintered $Al_2O_3$ | 9.86 |
| Sapphire | 9.86 |
| Silica glass | 11.30 |
| Silicon | 15.14 |

In the context of this invention, when milling media bodies of a first material and milling media bodies of a second material have relative brittleness index values $B_{1L}$ and $B_{2L}$, respectively, that are different from each other with $B_{2L}>B_{1L}$, and both $B_{1L}$ and $B_{2L}$ are less than about 5.5, then the media with the higher brittleness index value, $B_{2L}$, will spall the media with the lower brittleness index value, $B_{1L}$. When milling media bodies of a first material and milling media bodies of a second material have relative brittleness index values $B_{1H}$ and $B_{2H}$, respectively, that are different from each other and are greater than about 5.5 with $B_{2H}<B_{1H}$, then the media with the lower brittleness index value, $B_{2H}$, will spall the media with a higher brittleness index value, $B_{1H}$.

K. Friedrich in "Erosive wear of polymer surfaces by steel ball blasting," J. Mater. Sci. (1986), 21(9), 3317–32 describes the erosion behavior of a variety of polymeric materials using steel balls. Soft polymer materials showed an incubation period prior to stabilizing to a linear erosion rate defined as reduction in thickness per testing time. Polystyrene, a more brittle polymer, showed no incubation time and possessed a relatively high erosion rate in the study.

A brittleness index of the form hardness divided by fracture energy was a good indicator for the erosion resistance of the polymeric materials studied.

In one aspect, fracture strength of milling media materials may be estimated using the fracture toughness value $K_{IC}$, the highest stress intensity that a sample can withstand without fracturing. $K_{IC}$ is a material dependent property. $K_I$, the stress intensity factor which indicates the stress at the tip of a crack, is a stress dependent property. Fracture toughness, $K_{IC}$, increases with decreasing yield strengths of milling media materials.

The hardness of a material can be described as its ability to resist denting or deformation. The toughness of a material can be described as the load per unit area required to initiate a crack when this load is applied to a surface. A measure of the fracture toughness of a material is the critical stress intensity factor. It is calculated from crack lengths derived from the Vickers hardness test, and is a good approximation of the bend strength of a material. Compression strength is the maximum compressive load that can be applied to a material before it crumbles. Milling media bodies can undergo spalling by compression stress in the milling process of this invention.

The wear-resistance of solid milling media material can be broadly defined with respect to the ease of progressive removal of material from its surface under operational conditions. The abrasive wear-resistance of a solid milling media material is related to its hardness, its fracture toughness, and its elastic modulus. The harder the milling media material, the more wear-resistant it is, and the longer it will last under operational conditions. With respect to milling media materials, hard and tough material will cause spalling of less tough milling media material. In the context of this invention, it is possible to select milling media bodies of a first material that is less tough than milling media bodies of a second material, for example, by reference to their relative fracture toughness, hardness, and brittleness index values. Fracture toughness values and ranges of fracture toughness values for a non-limiting selection of representative milling media materials are given in Table 3. It is possible to select milling media bodies of a second material of this invention, which material is tougher and harder and less brittle than a first material. The milling media bodies of such a second material will cause spalling of milling media bodies of a first material which is less tough and more easily spalled. The milling media bodies of such a second material will also be essentially resistant to erosion in the milling process of this invention, for example by physical or mechanical means such as by abrasion and spalling, and for example by chemical means such as by etching, by selective solvation in a fluid carrier of one or more components of the second material, by dissolution, by swelling sufficient to render the milling media bodies not useful in this invention, or by other means.

Useful milling media materials include ammonium dihydrogen phosphate, aluminum nitride, alumina ($Al_2O_3$), sapphire, AlSiMag 614, aluminum titanate ($Al_2TiO_5$), barium fluoride, barium titanate, barium ferrite ($BaO.6Fe_2O_3$), barium oxide silicate ($3BaO.SiO_2$), boron carbide, beryllia (BeO), Bi:2212 ($Bi_2Sr_2CaCu_2O_{8+x}$), Bi(Pb) :2223 ($Bi_{2-x}Pb_xSr_2Ca_2Cu_3O_{10+y}$), boron nitride, diamond, calcium fluoride ($CaF_2$ fluorspar), Cervit 126, iron oxide (FeO), manganese zinc ferrite, nickel zinc ferrite, strontium ferrite, gallium nitride, gadolinium gallium garnet, graphite, potassium chloride, lithium silicate glass ($Li_2O.2SiO_2$), magnesium aluminate ($MgAl_2O_4$), magnesium fluoride, magnesium oxide, magnesium dititanate, mullite, pyroceram 9606, lead zirconate titanate ($PbZr_xTi_yO_3$), silicon, sialon, silicon carbide, silicon nitride ($Si_3N_4$), silicon oxynitride ($Si_2N_2O$), silicon dioxide, magnesium aluminate ($MgAl_2O_4$), strontium fluoride, strontium ferrite, strontium zirconate, thorium dioxide, titanium diboride, titanium carbide, titanium nitride, titanium dioxide, uranium dioxide, vanadium carbide, tungsten carbide, Y:123 $YBa_2Cu_3O_{7-x}$, yttrium aluminum oxide ($Y_3Al_5O_{12}$), yttrium oxide, zinc sulfide, zinc selenide, zirconium nitride, and zirconia.

TABLE 3

Representative Fracture Toughness and Fracture Energy Data of Representative Materials that can be used as milling media bodies according to this invention. Data are extracted from the NIST web site at http://www.ceramics.nist.gov/srd/summary/ftmain.htm

| Material | Fracture Toughness [$MPa \cdot m^{1/2}$] | Fracture Energy [$J/m^2$] | Method | Manufacturer |
|---|---|---|---|---|
| Ammonium Dihydrogen Phosphate (ADP) ($NH_4)H_2PO_4$) | | 2 | AMDCB | NRL E = 9 GPa |
| Aluminum Nitride (AlN) | 2.79 | | | Dow Chemical |
| Alumina ($Al_2O_3$) | | 25–54 | WOF | Smith Industries, NRL (99% $Al_2O_3$), Avco Corp. (98.7% $Al_2O_3$) |
| | 2.70–6.4 | | DCB | |
| | 2.1–6.81 | | DT | |
| | 3.0–5.0 | | SEPB | |
| | 2.68–6.25 | 20–42.2 | SENB | |
| | | 4.6–22.5 | AMDCB | |
| | 2.77–5.01 | | CT | |
| | 1.68–4.38 | | ICS | |
| | 3.75–5.45 | | IS | |
| | 2.5–4.6 | | CF | |
| Beta Alumina ($Al_2O_3$) | | 13 | AMDCB | NRL, Union Carbide: (93.6% $Al_2O_3$, 6.4% $Na_2O$), Cerametec: (90.55% $Al_2O_3$, 8.7% $Na_2O$, 0.75% $Li_2O$) |
| | 0.16–1.98 | | ICS | |
| Sapphire ($Al_2O_3$) | | 7 | AMDCB | Union Carbide |
| | 2.38–4.54 | | CF | |
| | | 6.0–7.3 | DCB | |
| | 1.89–2.1 | | ICS | |
| | 2.55 | | IS | |

TABLE 3-continued

Representative Fracture Toughness and Fracture Energy Data of Representative Materials that can be used as milling media bodies according to this invention. Data are extracted from the NIST web site at http://www.ceramics.nist.gov/srd/summary/ftmain.htm

| Material | Fracture Toughness [MPa · m$^{1/2}$] | Fracture Energy [J/m$^2$] | Method | Manufacturer |
|---|---|---|---|---|
| AD-85 (Al$_2$O$_3$) | 3.0 | 20 | AMDCB | Coors Porcelain Co. (85% Al$_2$O$_3$) |
|  | 2.98 |  | SR |  |
|  |  | 20.7 | DCB |  |
| AD-90 (Al$_2$O$_3$) | 2.9 |  | DCB | Coors Porcelain Co. (90% Al$_2$O$_3$) |
|  | 2.83 |  | ICS |  |
|  | 2.54 |  | IS |  |
|  | 3.06 |  | SR |  |
| AD-94 (Al$_2$O$_3$) | 3.8 |  | SCF | Coors Porcelain Co. (94% Al$_2$O$_3$) |
| AD-96 (Al$_2$O$_3$) | 3.31 |  | SR | Coors Porcelain Co. (96% Al$_2$O$_3$) |
|  | 3.27 |  | SEPB |  |
| AD-995 (Al$_2$O$_3$) | 3.7 | 19 | AMDCB | Coors Porcelain Co. (99.5% Al$_2$O$_3$) |
|  | 4.08 |  | SR |  |
| AD-999 (Al$_2$O$_3$) |  | 19.7 | SENB | Coors Porcelain Co. (99.9% Al$_2$O$_3$) |
|  | 3.9 | 19.05–24.3 | DCB |  |
|  | 3.32 |  | ICS |  |
|  | 3.09 |  | IS |  |
|  | 3.12 |  | SR |  |
|  | 3.39–3.6 |  | SCF |  |
| AlSiMag 614 (Al$_2$O$_3$) | 3.2 | 17–20 | AMDCB | Am. Lava Corp.(96% Al$_2$O$_3$), |
|  |  | 23.2 | SENB | Am. Lav. Corp. (Al$_2$O$_3$), |
|  | 3.49 |  | CNB | 3M Co. (96% Al$_2$O$_3$), |
|  | 3.3 |  | CNDCT | 3M Co (Al$_2$O$_3$) |
| GMB-352 (Al$_2$O$_3$) | 4.7 | 32 | AMDCB | Gladding McBean (99.3% Al$_2$O$_3$) |
| GMB-395 (Al$_2$O$_3$) | 4.9 | 44 | AMDCB | Gladding McBean (95% Al$_2$O$_3$) |
| Lucalox (Al$_2$O$_3$) | 4.1 | 22 | AMDCB | GE (99.9% Al$_2$O$_3$) |
|  |  | 20.3 | SENB |  |
|  | 3.38–5.25 | 18–46 | DCB |  |
|  | 5.25 |  | ICS |  |
| Lucalox-HS (Al$_2$O$_3$) | 3.7–5.0 | 18–32 | AMDCB | GE (99.9% Al$_2$O$_3$) |
| McDanel 998 (Al$_2$O$_3$) | 4.9 | 35 | AMDCB | McDanel Refractory Porcelain Co (99.8% Al$_2$O$_3$) |
| Monofrax A (Al$_2$O$_3$) | 2.47 | 13.25 | AMDCB |  |
| Monofrax M (Al$_2$O$_3$) | 1.09 | 3.3 | AMDCB |  |
| Vistal (Al$_2$O$_3$) | 4.41 |  | SR | Coors Porcelain Co. (99.9% Al$_2$O$_3$) |
| XA16 (Al$_2$O$_3$) |  | 11.5–47.3 | WOF | Alcoa |
|  |  | 10–43.2 | SENB |  |
|  |  | 20.8–38.8 | DCB |  |
| Aluminum Titanate (Al$_2$TiO$_5$) |  | 1–2 | WOF |  |
| Barium Fluoride (BaF$_2$) |  | 0.35 | AMDCB |  |
| Barium Titanate (BaTiO$_3$) | 1.05 | 4.5–6 | AMDCB | Channel Industries, Clevite Corp., NRL |
| Barium Ferrite | 0.96 | 2.82 | CF |  |
| BaO.6Fe$_2$O$_3$ | 1.57 | 6.35 |  |  |
|  | 2.83 | 11.92 |  |  |
| Barium Oxide Silicate (3BaO.SiO$_2$) |  | 17 | AMBDC | NRL |
| Boron Carbide |  | 15 | AMDCB | Norton Co., |
| (B$_4$C) | 3.2–3.7 | 11.8 | SENB | ESK, |
|  | 1.8 |  | DT | Ceradyne |
|  | 4.2 |  | ICS |  |
|  | 3.08 |  | SCF |  |
| Beryllia |  | 15 | WOF | AERE Harwell |
| (BeO) | 3.58 |  | AMDCB |  |
|  |  | 32.3 | DCB |  |
| Bi:2212 (Bi$_2$Sr$_2$CaCu$_2$O$_{8+x}$) | 1.2–3.9 |  | SENB |  |
| Bi(Pb):2223 (Bi$_{2-x}$Pb$_x$Sr$_2$Ca$_2$Cu$_3$O$_{10+y}$) | 0.3–2.6 |  | SENB |  |
| Boron Nitride (BN) | 5.0 |  | ICS |  |
| Diamond (C) | 5.3–14.0 |  | ICS | Natural specimen |
| Calcium Fluoride (CaF$_2$) fluorspar |  | 0.51–3.6 | AMDCB | Harshaw Co., Eastman Kodak Co. |
| Cervit 126 |  | 17 | AMDCB | Owens Illinois |
| Iron Oxide (FeO) |  | 6.8–8.2 | DCB |  |
| Manganese Zinc Ferrite Mn—Zn—Fe$_2$O$_3$ |  | 1.40–1.54 | SENB |  |
| Nickel Zinc Ferrite Ni—Zn—Fe$_2$O$_3$ | 1.36–1.42 |  | SENB |  |
| Strontium Ferrite (SrO.6Fe$_2$O$_3$) | 1.71–1.80 |  | SENB |  |
| Gallium Nitride (GaN) | 0.8 |  | ICS |  |
| Gadolinium Gallium Garnet (Gd$_3$Ga$_5$O$_{12}$) | 1.2 |  | ICS |  |
| Graphite (C) |  | 85 | AMDCB | Poco Graphite Inc. |
| HPD-1 (Graphite C) |  | 68.1 | DCB | Poco Graphite Inc. |
| Potassium Chloride (KCl) |  | 0.14–0.27 | AMDCB |  |
| Lithium Silicate Glass (Li$_2$O.2SiO$_2$) |  | 34–95 | AMDCB | NRL |
| Magnesium Aluminate | 1.0–1.7 | 7–8 | AMDCB |  |
| (MgAl$_2$O$_4$) | 1.18–1.98 |  | CF |  |

TABLE 3-continued

Representative Fracture Toughness and Fracture Energy Data of Representative Materials that can be used as milling media bodies according to this invention. Data are extracted from the NIST web site at http://www.ceramics.nist.gov/srd/summary/ftmain.htm

| Material | Fracture Toughness [MPa · m$^{1/2}$] | Fracture Energy [J/m$^2$] | Method | Manufacturer |
|---|---|---|---|---|
| | | 9.1–16.9 | DCB | |
| | 1.3 | | ICS | |
| | 1.5 | | DT | |
| | 3.0 | | SENB | |
| Magnesium Fluoride | | 4 | AMDCB | Kodak |
| (MgF$_2$) | 0.98 | | SCF | |
| Magnesium Oxide | | 0.9–35 | WOF | Thermal Syndicate Ltd., |
| (MgO) | | 3–18 | AMBCB | Eastman Kodak, |
| | 1.3–2.0 | | CNB | Norton |
| Magnesium Dititanate (MgTi$_2$O$_5$) | | 11–39 | WOF | |
| Mullite 3Al$_2$O$_3$.2SiO$_2$ | | 11 | AMDCB | |
| | 2.45–2.83 | | SENB | |
| | 2.7 | | ICS | |
| | 1.8 | | CF | |
| Pyroceram 9606 | 2.5 | | DCB | Corning Glass |
| | 2.8–3.17 | | ICS | |
| | 2.5–2.69 | | IS | |
| | 2.14 | | CNB | |
| | 2.07 | | CNDC | |
| | | 24.8 | SENB | |
| | 2.25 | | SCF | |
| Lead Zirconate Titanate (PbZr$_x$Ti$_y$O$_3$) | 0.75–0.81 | 4 | AMDCB | Channel Ind., |
| | 1.35–1.52 | | DT | Morgan |
| | 0.70–1.82 | | ICS | |
| | 0.86–1.08 | | SCF | |
| Silicon | 0.79 | | ICS | Texas Instruments |
| (Si) | 0.95 | | IS | |
| | | 2.7 | TDCB | |
| Sialon Si$_{6-x}$Al$_x$O$_x$N$_{8-x}$ | 2.65–4.65 | 55.4–87.9 | ICS | |
| Silicon Carbide | 3.3 | 15.2–27 | SENB | UKAEA Springfields Lab., |
| (SiC) | | 15–32.4 | DCB | Carborundum Co., |
| | | 18–25.5 | AMDCB | Norton Co., |
| | 3.1–4.0 | | ICS | General Electric |
| Alpha Silicon Carbide | 4.6 | | DT | Carborundum |
| (SiC) | 3.47 | | DCB | |
| | 2.96 | | CNB | |
| | 4.78 | | SENB | |
| | 3.31 | | CF | |
| | 1.10–3.65 | | ICS | |
| Beta Silicon Carbide (SiC) | 2.0 | | ICS | General Electric Co. |
| CVD Silicon Carbide (SiC) | | 16–21 | AMDCB | Composites and Deposits |
| Ceralloy 146I (SiC) | | 13.41–24 | AMDCB | Ceradyne Corp. |
| Hexoloy SA | 2.6–3 8 | | CF | Carborundum Co. |
| (SiC) | 2.91 | | CN | SiC (alpha) + 0.4% B + 0.5% free C |
| | 3.31–3.88 | | SENB | |
| | 3.4 | | ICS | |
| | 3.01 | | SCF | |
| HP-D | | 44.6 | DCB | Norton Co. |
| (SiC) | | 35.7 | SENB | |
| | | 83.3 | WOF | |
| KT (SiC) | | 19 | AMDCB | Norton Co. |
| NC-203 | | 18.52–19 | AMDCB | Norton Co. |
| (SiC) | 3.38 | | ICS | |
| | 4.42 | | IS | |
| | 3.85–4.37 | | SCF | |
| NC-430 (SiC) | 4.3 | | CNB | Norton Co. |
| NC-435 (SiC) | 3.7 | | SCF | Norton Co. |
| RS-E | | 30.7 | DCB | Carborundum Co. |
| (SiC) | | 19.0 | SENB | |
| | | 23.5 | WOF | |
| RX-A | | 14.7 | DCB | Norton Co. |
| (SiC) | | 15.8 | SENB | |
| | | 11.1 | WOF | |
| RX-B | | 15.0 | DCB | Norton Co. |
| (SiC) | | 14.4 | SENB | |
| | | 12.2 | WOF | |
| RX-C | | 29.6 | DCB | Norton Co. |
| (SiC) | | 24.5 | SENB | |
| | | 26.5 | WOF | |
| SCRB210 (SiC) | 5.3 | | SENB | Coors Porcelain Co. |
| Silicon Nitride | 7.2–8.3 | 52–110 | AMDCB | NRL, |

TABLE 3-continued

Representative Fracture Toughness and Fracture Energy Data of Representative Materials that can be used as milling media bodies according to this invention. Data are extracted from the NIST web site at http://www.ceramics.nist.gov/srd/summary/ftmain.htm

| Material | Fracture Toughness [MPa · m$^{1/2}$] | Fracture Energy [J/m$^2$] | Method | Manufacturer |
|---|---|---|---|---|
| (Si$_3$N$_4$) | 3.2–7.81 | | SENB | Toshiba, |
| | | 16.5–67.8 | WOF | AMMRC, |
| | 3.12–4.9 | | ICS | KBI, |
| | | 15.8–69.5 | DCB | Norton Co., |
| | 2.7–6.75 | | SCF | Dow Chemical |
| | 4.5 | | CNB | |
| Beta Silicon Nitride (Si$_3$N$_4$) | | 30 | AMDCB | Beckwith, Inc. |
| Ceralloy 147 (Si$_3$N$_4$) | 4.6–7.2 | 34–83 | AMDCB | Cerdyne Corp. (Si$_3$N$_4$ + 1% MgO and Si$_3$N$_4$ + 15% Y$_2$O$_3$) |
| EC-141 (Si$_3$N$_4$) | 5.22 | | SCF | NTR |
| HS-110 (Si$_3$N$_4$) | | 45 | AMDCB | Norton Co. |
| HS-130 (Si$_3$N$_4$) | 4.5 | | SENB | Norton Co. |
| | | 43–45 | AMDCB | |
| NAV-4 (Si$_3$N$_4$) | | 58 | AMDCB | Norton Co. |
| NAV-5 (Si$_3$N$_4$) | | 38 | AMDCB | Norton Co. |
| NAV-7 (Si$_3$N$_4$) | | 62 | AMDCB | Norton Co |
| NAV-8 (Si$_3$N$_4$) | 5.5 | 49 | AMDCB | Norton Co |
| NBD-200 (Si$_3$N$_4$) | 5.4 | | SCF | Cerbec |
| NC-132 (Si$_3$N$_4$) | 4 | 17–26 | AMDCB | Norton Co. |
| | 4.36 | 40.1–61.3 | SENB | |
| | 4.0 | | DCB | |
| | 4.98 | | ICS | |
| | 5.25 | | IS | |
| | 4.6 | | SCF | |
| NC-350 | 2.71 | | ICS | Norton Co |
| (Si$_3$N$_4$) | 2.13 | | IS | |
| | 1.65 | | SCF | |
| NCX-34 (Si$_3$N$_4$) | 6.35 | | SCF | Norton Co. |
| NCX-5102 (Si$_3$N$_4$) | 5.36 | | SCF | Norton Co. |
| | 6.0 | | SEPB | |
| NT-154 | 3.8 | | ICS | Norton/TRW |
| (Si$_3$N$_4$) | 3.2 | | CF | |
| | 3.7 | | SCF | |
| NT-164 (Si$_3$N$_4$) | 4.0 | | ICS | Norton/TRW |
| SNW-1000 | 4.0 | | CF | GTE Sylvania |
| (Si$_3$N$_4$) | 4.7–6.4 | | SCF | |
| Silicon Oxyntride (Si$_2$N$_2$O) | 3.2 | | ICS | |
| Silicon Dioxide (SiO$_2$) | 0.85–1.15 | | CF | |
| Magnesium Aluminate | 1.0–1.7 | 7–8 | AMDCB | Compositions: |
| (MgAl$_2$O$_4$) | 1.18–1.98 | | CF | MgAl$_2$O$_4$; |
| | | 9.1–16.9 | DCB | MgO.Al$_2$O$_3$; |
| | 1.3 | | ICS | MgO.3.5Al$_2$O$_3$; |
| | 1.5 | | DT | MgAl$_2$O$_4$ + 0.01% CaZrO$_4$ |
| | 3.0 | | SENB | |
| Strontium Fluoride | | 0.42 | AMDCB | Harshaw Chemical Co. |
| (SrF$_2$) | | 0.36 | DCB | |
| Strontium Ferrite SrO.6Fe$_2$O$_3$ | 1.71–1.80 | | SENB | |
| Strontium Zirconate (SrZrO$_3$) | | 6 | AMDCB | |
| Thorium Dioxide (ThO$_2$) | 1.07 | 2.5 | HI | |
| Titanium Diboride | 2.3–6.4 | | ICS | ORNL compositions: |
| (TiB$_2$) | 4.87 | | DT | TiB$_2$; TiB$_2$ + 7.9% Ni; |
| | 5.14–5.36 | | SCF | TiB$_2$ +1.4% Ni; Sylvania: |
| | 5.0 | | SENB | (compositions: TiB$_2$) |
| | 4.6 | | IS | |
| Titanium Carbide | 3.8 | | SENB | |
| (TiC) | 1.7–3.0 | | ICS | |
| Titanium Nitride | 3.4–5.5 | | SENB | Compositions: TiN; TiN + 5% Al$_2$O$_3$; TiN + 5% MgO; TiN + 5% Y$_2$O$_3$ |
| (TiN) | | | | |
| Titanium Dioxide | 5.1 | | DT | |
| (TiO$_2$) | 2.8 | | ICS | |
| Uranium Dioxide (UO$_2$) | | 3.5–6.5 | SENB | UKAEA Springfields Lab |
| Vanadium Carbide (VC) | | 1.3–1.9 | CF | |
| Tungsten Carbide (WC) | 7.5–8.9 | | SENB | Ugine Carbone, Inc. compositions: WC and WC + 0.5% Co. |
| Y:123 YBa$_2$Cu$_3$O$_{7-x}$ | 0.24–1.85 | | ICS | |
| | 1.05–1.4 | | CNB | |
| | 0.5–3.1 | | SENB | |
| Yttrium Aluminum Oxide (Y$_3$Al$_5$O$_{12}$) | 2.2 | | SENB | |
| Yttrium Oxide | | 3.8–5.2 | SENB | Raytheon Research Division |
| (Y$_2$O$_3$) | 0.71 | | ICS | |
| Zinc Sulfide (ZnS) | 0.75 | | ER | Raytheon |

TABLE 3-continued

Representative Fracture Toughness and Fracture Energy Data of Representative Materials that can be used as milling media bodies according to this invention. Data are extracted from the NIST web site at http://www.ceramics.nist.gov/srd/summary/ftmain.htm

| Material | Fracture Toughness [MPa · m$^{1/2}$] | Fracture Energy [J/m$^2$] | Method | Manufacturer |
|---|---|---|---|---|
| Zinc Selenide (ZnSe) | 1.0 | | ISC | |
| | 0.9 | | ICS | Raytheon |
| | | 4 | AMDCB | |
| Zirconium Nitride (ZnN) | 3.6–6.2 | 48 | SENB | |
| Zirconia (cubic) | 2.5 | | NDC | Compositions: $ZrO_2.xY_2O_3$ and $ZrO_2.xCeO_2$ |
| ($ZrO_2$) | 1.6–2.5 | | ICS | |
| Zirconia (PSZ) | 4.8–12.3 | | SENB | Compositions: $ZrO_2.xMgO$; |
| ($ZrO_2$) | 4.0–4.8 | | ICS | $ZrO_2.xY_2O_3$; and $ZrO_2.xCaO$ |
| ZirconiaTZP ($ZrO_2$) | 11.6 | | NDC | Compositions: $ZrO_2.xY_2O_3$; $ZrO_2.xCeO_2$ |
| | 4.4 | | SCF | (up to 48%); $ZrO_2.3\%\ Y_2O_3$ |
| (Fracture toughness varies inversely with | 2.0–17.2 | | SENB | |
| the amount of $CeO_2$) | 4.4–36.0 | | ICS | |
| Zircar ($ZrO_2$) | | 70 | AMDCB | Union Carbide |
| Zyttrite ($ZrO_2$) | | 13 | AMDCB | AFML |

Measurement Method Abbreviations:
AMDCB = Applied Moment Double Cantilever Beam;
CF = Controlled Flaw;
CNB = Chevron Notch Beam;
DCB = Double Cantilever Beam;
DT = Double Torsion;
HI = Hettzian Indentation;
ICS = Indentation Crack Size;
IS = Indentation Strength;
NDC = Notched Diametral Compression;
SCF = Surface Crack in Flexure;
SENB = Single-Edge Norched-Beam;
SEPB = Single-Edge Precracked Beam;
SR = Short Rod;
TDCB = Tapered Double Cantilever Beam;
WOF = Work of Fracture.
Property Abbreviations:
E = elastic modulus (Young's modulus);
H = hardness (Vickers hardness unless noted otherwise);
nu = Poisson's ratio

TABLE 4

Example illustrating how fracture toughness of a milling media body material ($ZrO_2$) can change when doped with a second material ($CeO_2$ in this example) in a composite of at least two materials.

| Zirconia TZP ($ZrO_2$) plus: | | | Fracture Toughness [MPa · m$^{1/2}$] | Method |
|---|---|---|---|---|
| 3% | $Y_2O_3$ | | 11.6 | NDC |
| 3% | $Y_2O_3$ | | 4.4 | SCF |
| 2.0% | $Y_2O_3$ | 1.4 micron grain size | 17.2 | SENB |
| 2.5% | $Y_2O_3$ | 1.4 micron grain size | 11.2 | SENB |
| 3% | $Y_2O_3$ | 1.3 micron grain size | 12.3 | SENB |
| 2.6% | $Y_2O_3$ | | 9.5 | SENB |
| 2.6% | $Y_2O_3$ | | 5.6 | SENE |
| 3% | $Y_2O_3$ | | 10.6 | SENB |
| 3% | $Y_2O_3$ | | 4.7 | SENB |
| 10% | $CeO_2$ | | 10 | SENB |
| 12% | $CeO_2$ | | 8.5 | SENB |
| 14% | $CeO_2$ | | 4.4 | SENB |
| 16% | $CeO_2$ | | 4.3 | SENB |
| 24% | $CeO_2$ | | 4.0 | SENB |
| 32% | $CeO_2$ | | 3.2 | SENB |
| 40% | $CeO_2$ | | 2.6 | SENB |
| 48% | $CeO_2$ | | 2.0 | SENB |
| 8.6% | $CeO_2$ | 0.5 micron grain size | 17.1 | ICS |
| 9.5% | $CeO_2$ | 0.5 micron grain size | 16.9 | ICS |
| 10.8% | $CeO_2$ | 0.5 micron grain size | 12.6 | ICS |
| 12.2% | $CeO_2$ | 0.5 micron grain size | 9.5 | ICS |
| 15.8% | $CeO_2$ | 0.5 micron grain size | 5.8 | ICS |
| 8.6% | $CeO_2$ | 2.5 micron grain size | 8.7 | ICS |
| 9.5% | $CeO_2$ | 2.5 micron grain size | 6.4 | ICS |
| 10.8% | $CeO_2$ | 2.5 micron grain size | 5.3 | ICS |
| 12.2% | $CeO_2$ | 2.5 micron grain size | 4.9 | ICS |
| 15.8% | $CeO_2$ | 2.5 micron grain size | 4.4 | ICS |
| 12% | $CeO_2$ | 0.5 micron grain size | 23.0 | ICS |
| 14% | $CeO_2$ | 0.5 micron grain size | 8.0 | ICS |
| 16% | $CeO_2$ | 0.5 micron grain size | 4.0 | ICS |
| 12% | $CeO_2$ | 1.0 micron grain size | 36.0 | ICS |
| 14% | $CeO_2$ | 1.0 micron grain size | 9.0 | ICS |
| 16% | $CeO_2$ | 1.0 micron grain size | 5.0 | ICS |

It is possible to adjust the fracture toughness of a composite of two or more ceramic materials by increasing the percentage of one component and decreasing the percentage of another component in the composite. Fracture toughness of zirconium oxide or zirconia varies inversely with the amount of cerium oxide in the composition of milling media bodies of zirconium oxide and cerium oxide. As the percentage of cerium oxide increases from 8.6% to 15.8% in a 0.5 micron body of zirconium oxide and cerium oxide, the fracture toughness decreases from 17.1 to 5.8 MPa m$^{1/2}$. As the percentage of cerium oxide increases from 8.6% to 15.8% in a 2.5 micron body of zirconium oxide and cerium oxide, the fracture toughness decreases from 8.7 to 4.4 MPa$^{1/2}$.

Fracture toughness of a material and its ability to be spalled by tougher and harder material is a function of porosity and also a function of added ingredients. Porous materials tend to be less tough than non porous materials of the same composition. In this invention, porosity of a given material can be increased by methods known in the art to render the material less tough and therefore more readily spalled by tougher milling media bodies according to this invention. Composite materials comprising a mixture of materials can also be prepared by known methods to provide milling media bodies with altered fracture toughness as a function of the composition. For example, when a material having a high fracture toughness is doped with a second material that does not fit molecularly exactly into the crystal structure or packing structure of the first material as a solid, or if domains of different material phase-separate from each other in the composite, then the fracture toughness of the first material can change, often decreasing, as a function of the amount of the second material doped into the composition. This can alter the fracture toughness, hardness, and brittleness index to provide milling media bodies that are useful as milling media bodies of a first material according to this invention.

Milling media bodies can be designed and prepared with fracture toughness values that permit the media to be spalled in the milling process by media of higher fracture toughness, i.e, more tough and less readily spalled. The spalled material can then be incorporated as a synergetic component in the milled substrate material. A representative and non-limiting example that demonstrates alteration of fracture toughness in a material as a major component (zirconia in this case) of a composite material with varying amounts of a second material (cerium oxide or yttrium oxide in this example) is presented in Table 4. The data are taken from the NIST web site noted previously. Such composite materials, i.e., composite materials comprising a major material and one or more doping materials, can be tailored to have fracture toughness values, hardness values, and brittleness index values suitable for use according to this invention when used as milling media bodies to grind a substrate while being spalled and incorporated as a synergetic component of the milled substrate.

The data in the Tables also demonstrate that measured fracture toughness, hardness, and calculated brittleness indexes of a given composition is a function of the method used to measure fracture toughness and hardness values and of the size of the material on which the measurement is made. For a given method and conditions of measuring the fracture toughness and hardness of a materials of a given composition useful as milling media bodies in this invention, increasing the size of the media particles can sometimes provide material that exhibits a decreased fracture toughness when compared to the media particles of the same material but of a smaller size.

Fracture toughness or body strength characteristics are significant to milling media function and behavior. A milling media particle can undergo breakdown or fragmentation and expose a new edge or surface within the same particle. In synthetic media it is possible to achieve some degree of control over this property, for example by varying grain shape during crushing, milling, or sizing operations in the preparation of the media, by introduction of impurities into the crystal structure as crystal growth modifiers, by modification of the compositional purity of the media, by alloying media, and by controlling the crystal structure or morphology within media grains.

In one aspect of this invention for each combination of solid to be milled by milling bodies (or milling media) of a first material and milling bodies (or milling media) of a second material, the fracture toughness of milling bodies of the second material is higher than the fracture toughness of milling bodies of the first material. Milling bodies of the second material are tougher than milling bodies of the first material. Methods used to determine fracture toughness are known to have difficult-to-quantify influences on the measured values found especially with respect to the measurement of fracture toughness of small milling media. Values of fracture toughness determined by different measuring techniques can be compared qualitatively with one another in order to select a milling media of a first material and a milling media of a second material where both types of media (of the first material and of the second material) will act as milling media in the milling process of this invention to reduce the size of a solid substrate in a premix to small particles of a desired size, where milling bodies of the second material will spall (i.e., fracture or chip) the milling bodies of the first material, and where particulates derived from milling bodies of the first material form a synergetic commixture with the particles of the solid. Fracture toughness values measured according to the same method can be useful to quantify the relative tendency of milling bodies of a first material to be spalled by milling bodies of a second material to produce particulates of milling media according to this invention.

The extent of interaction among various milling media particles and between milling media particles of a first and second type and a solid substrate being ground or milled can vary from system to system. For example, when silicon carbide media (an example of a harder, tougher, less brittle second type of media) are used in the presence of steel media (an example of a less tough first type of media), or when alumina media (an example of a harder, second type of media) are used in the presence of glass or silica media (an example of less tough, first type of media), spalling or fragmentation or chipping of the weaker, less tough media into very small particulates can take place during milling operations. The amount of fragmentation or breakage of one type of milling particle by another is related to the attrition resistance between the two materials, their relative toughness, and their relative hardness.

Fracture toughness of a solid can be related to how readily a solid can be fractured under the application of a pressure. For example, Shipway and Hutchings in "The influence of particle properties on the erosive wear of sintered boron carbide," Wear of Materials (1991), 8th(Vol. 1), 63–70 reported results of erosion of sintered boron carbide ceramic by silica, alumina, and silicon carbide, and suggested that separate mechanisms involving lateral cracking and large scale fracture (by relatively hard silicon carbide) and small-scale chipping (by relatively less hard silica and alumina) were operative as an inverse function of relative Vickers hardness values, $H_V$, of the materials. Fracture toughness, $K_C$, can be correlated with the indentation load, P, the indent diagonal half length, a, the Young modulus, E, and the radial crack length, c, according to the following equation: $K_C = 0.0141(P/a^{3/2})(EHv)^{2/5} \log_{10}(8.4a/c)$. At constant load, Vickers hardness, $H_V$, for 125 μm SiC was 33.41 GPa, for 125 μm Al$_2$O$_3$ was 26.50 GPa, for larger 600 μm SiO$_2$ was 12.77 GPa, and for smaller 125 μm SiO$_2$ was 12.77 GPa.

The square of the brittleness index, $(K_C/H_V)^2$, has units of length (meters), and can be taken to indicate a dimension of the deformation zone at which transition between ductile and brittle behavior will occur. A silica erodent can be fragmented by boron carbide by a minor chipping cleavage fracture mechanism to give small particulates of silica. In addition, although alumina has a fracture toughness value comparable to boron carbide, boron carbide can cause minor chipping of alumina milling media particles similar to that of silica. As the velocity of impact increases, the degree of fragmentation of silica by the harder and tougher material increases. There can be a tendency of a relatively soft particle such as silica to deform plastically on impact with a harder material such as boron carbide leading to the production of small chips of silica particles. Small silica particles can be harder than larger silica particles, and larger silica particles can have higher fracture toughness values than smaller silica particles. Small silica particles are sometimes about 1.15 or more times tougher than large silica particles. In the process of this invention, tougher particles can have a fracture toughness, $K_{C2}$, greater than 1.1 times the fracture toughness of the less tough particles with a fracture toughness of $K_{C1}$.

Mechanisms of interactions between particles leading to their chips, fractures, and disintegrations (spalling) especially of chips, fractures, and disintegrations of a first type of milling media bodies caused by collision with a second type of milling media bodies depend on the composition and structure of the media particles. For some combinations of kinetic second milling media particles having a hardness value $H_{V2}$ and first milling media particles having a hardness value $H_{V1}$, the erosion rate of the less hard media can be approximated as an empirical function of the relative hardnesses of the materials impinging upon each other. In this regard, Erosion rate $\sim(H_{V2}/H_{V1})^w$, where w is an empirical exponent approximately equal to 2. Relative hardness values are given in Table 1 for materials that can be used in combination as milling media bodies of first materials and second materials.

Tougher and harder milling media bodies will fracture and/or chip and/or abrade and/or erode less tough and less hard milling media particles in a milling process wherein the particles collide with each other. However, milling media bodies that are soft will deform elastically. Relatively hard and more tough milling media bodies will fracture relatively more brittle and less tough milling media particles. Milling at low temperatures can sometimes increase the brittleness of soft milling media.

The spalling of milling media bodies of a first type of material by milling media bodies of a second type of material can be described as a function of the relative fracture toughnesses, $K_{C2}/K_{C1}$, of the impinging materials.

In another aspect, the spalling of brittle materials such as milling media bodies of a first type by milling media bodies of a second type can be approximated as a relationship between an erosion rate, E, of a first material and the velocity of impingement of an erodent comprised of a second material, v, given by $E=v^n$, where n is a constant known as the velocity exponent.

Verspui et al in Rev. Sci. Instrum. (1997), 68(3), 1553–1556 identified three types of failure in stressed alumina particles that are relevant to spalling of milling media. These are chipping of the particles wherein small pieces are detached from the particles; breaking, wherein a particle breaks into a few (about 2 or 3) large pieces; and fragmentation, wherein a particle breaks into many small pieces.

Chipping, breaking, and fragmentation are often referred to as spalling, and milling media bodies of a tough material can spall milling media bodies of a less tough material. Particulates of milling media bodies less than or equal to a desired size can be derived from milling media bodies of a first material when these media are spalled by milling media bodies of a second material. In this regard, the milling media bodies of the second material have a higher fracture toughness than the milling media bodies of the first material. In one aspect of this invention, particulates of milling media bodies are defined as chips, fragments, or pieces of milling media bodies of a size less than a desired size Sp, together with any milling media bodies whose size has not been altered during a milling process and which has size less than Sp.

In another aspect of this invention, when two compositions of milling media bodies or types of milling media bodies having different fracture toughnesses $K_{C1}$ and $K_{C2}$ are present in the milling chamber of a media mill together with a solid substrate as a premix optionally including one or more surface active substances in a fluid carrier, the solid and the less tough and more easily spalled milling media bodies with fracture toughness $K_{C1}$ are reduced in size in the milling process to form a synergetic commixture comprising small particles of solid and small particulates of milling media. Both types of media, the media having lower fracture toughness $K_{C1}$ (i.e., the less tough media) and the media having a higher fracture toughness $K_{C2}$ (i.e, the more tough media) contribute to the milling and size reduction of the solid substrate. In addition, the less tough milling media bodies also experiences size reduction to form particulates of milling media. In this aspect of the invention, the ratio of fracture toughness of milling media bodies of a second material to the fracture toughness of milling media bodies of a first material, i.e., $K_{C2}/K_{C1}$ is greater than 1.1, preferably greater than 1.3 and most preferably greater than 1.5. Tough materials such as yttrium-containing zirconium silicate ceramics can readily spall less tough materials such as marble or calcium carbonate. Fracture toughness values for some milling media materials are given in Tables 1 and 2. When milling media bodies of a first material have a fracture toughness $K_{C1}$ of less than 1, then a preferred second material can have a fracture toughness $K_{C2}$ of greater than 1.5 and preferably greater than 2. When milling media bodies of a first material have a fracture toughness $K_{C1}$ of less than 1.5, then a preferred second material can have a fracture toughness $K_{C2}$ of greater than 2.25 and preferably greater than 2.5. When milling media bodies of a first material have a fracture toughness $K_{C1}$ of less than 2, then a preferred second material can have a fracture toughness $K_{C2}$ of greater than 3 and preferably greater than 3.5. Preferably, $K_{C2}$ is at least 1.1 times larger than $K_{C1}$, more preferably at least 1.3 times larger than $K_{C1}$, and most preferably at least 1.5 times larger than $K_{C1}$.

As the solid is reduced to a desired size, the small particles of solid can form a dispersion in the fluid carrier. In addition, small particulates of the less tough milling media bodies are dispersed with the particles of solid to form a synergetic commixture comprising particles of solid substrate and particulates of less tough milling media bodies equal to or less than a desired size, Sp. Particles of material larger than Sp, for example particles of the solid substrate or premix larger in size than Sp, less tough milling media bodies larger in size than Sp, pieces of less tough milling media bodies larger in size than Sp, and tougher milling media bodies larger in size than Sp can be removed from the dispersion comprising the commixture of small particles of solid substrate and small particulates of milling media bodies by a filtration or separation step. The separation of the dispersion comprising the synergetic commixture of small particles of solid substrate and small particulates of milling media bodies can be done in the mill using a size dependent separation device such as a filter, a filtration device, or media separator well known in the art. Alternatively, the dispersion and residual large size materials present in the milling chamber can be removed from the milling chamber and separated, the small size dispersion from the large size residual solid substrate and milling agents, by a filtration or separation process. The synergetic commixture can then optionally be dried such as by spray drying, lyophilization, distillation, evaporation, and other methods known in the art to produce a synergetic commixture free of fluid and comprising small particles of solid substrate and small particulates of milling media.

Particulates of milling media bodies of a first material that are produced in the milling process of this invention that form a synergetic commixture with particles of the solid being milled can comprise from about 0.01% to 100% of the amount of milling media bodies of said first material present in the milling process. The portion of the milling bodies that can be degraded or spalled to form particulates can be from 0.01% to 100% of the milling media bodies of the first material in the process of this invention, preferably from about 0.1% to about 100%, and more preferably from about 1% to about 100%. In one aspect, the milling media bodies of a first material can be smaller than the desired size of the particles of solid being milled. In this embodiment, particulates of milling media bodies comprise spalled milling media bodies of the first material and unspalled milling media bodies of the first material. The size distribution of the plurality of milling bodies present before spalling is smaller than the desired size of particles of solid and becomes smaller as spalling occurs. When the size distribution of milling media bodies of a second material are larger than the desired size of particles and particulates in the synergetic commixture, the larger media can be removed from the dispersion of the commixture by a number of means including size dependent separation techniques such as by filtration or by sieving or screening using for example separation devices in a media mill.

In this invention, in the absence of particulates of milling media bodies of a first material, the small particles of solid substrate otherwise present in a synergetic commixture have associated therewith a property, use, or function. In a synergetic commixture of small particles of solid substrate and small particulates of milling media bodies in this invention, said property, use, or function of the small particles of solid substrate is equal to or improved over said property use of function of the small particles of solid substrate exhibited in the absence of small particulates of milling media. Alternatively, in this invention the synergetic commixture has associated therewith a new property, use, or function that is not associated with the small particles of solid substrate alone or in the absence of the small particulates of milling media bodies or a new property, use, or function that is not associated with the small particulates of milling media bodies alone in the absence of the small particles of solid substrate.

Examples of synergetic commixtures include small particles of a pharmaceutical agent such as a poorly water soluble drug and particulates of milling media bodies that comprise an excipient such as silica in a formulation of said pharmaceutical agent which excipient affects the tableting integrity or rate of release of the particles of drug from tablets made from the commixture; small particles of portland cement and small particulates of sand where the commixture can be used in the formation of concrete in which the concrete is stronger and has a setting time different from that of the cement alone; and small particles of aluminum oxide and small particulates of alpha-alumina that can seed the crystallization of the aluminum oxide into alpha alumina grinding materials. Additional examples of synergetic commixtures include the addition of dyes and pigmented media particulates to uniformly distribute into a cosmetic ointment or cream or into a photographic element comprising a dye such as a filter dye.

Diverse industrial applications of solid materials as small particles as a synergetic commixture with particulates of milling media bodies include the production of paints (particles of pigment and particulates of an ultraviolet light-absorbing dye); pigments; photographic materials; cosmetics (particles of pigment and particulates of zinc oxide); chemicals; cements such as portland cement; black powder explosives and glazed black powder explosives (particles of carbon and particulates of an oxidation catalyst such as a nitrate salt); metal powders useful as catalysts and supports (particles of a first metal and particulates of a second metal or metal oxide); grinding and abrasion media; stationary phase particles useful in analytical and preparative chromatographic separations of chemical compounds and mixtures such as those encountered in forensic science, food, cosmetics, chemical, and pharmaceutical studies; powdered toners, both black and colored, useful in xerographic and printing applications including laser printing; and small particles of solid pharmaceutical agents including water soluble, water insoluble, and poorly water soluble therapeutic and diagnostic imaging agents; medicinally active agents; medicaments; plant and herbal extracts; drugs; pro-drugs; drug formulations; dosage forms including pharmaceutical pastes such as those containing calcium carbonate, talc, zinc oxide and other fine solid materials; controlled release agents; timed release agents; matrix release agents: diagnostic agents; tablets; pills; creams; ointments; suppositories; pessaries; powders; pastes; jellies; capsules; granules; cachets; lozenges; and pastilles. In the case of a pharmaceutical agent such as a drug used in therapeutic treatment of a disease or a drug used in a diagnostic process, formulation of the agent in the form of small particles can provide altered and often increased microscopic properties such as increased bioavailability of the agent, increased rate of dissolution of the agent, increased rate of absorption of the agent, improved dosage profiles, and concomitant reduction in weight of agent dosed or administered to a patient undergoing a treatment or diagnosis involving the agent.

Examples of surface active substances which are incorporated herein by reference are listed in McCutcheon's, Volume 1: Emulsifiers and Detergents, 1994 International Edition; McCutcheon's, Volume 1: Emulsifiers and Detergents, 1994 North American Edition; and McCutcheon's, Volume 2: Functional Materials, 1994 North American Edition, all available from McCutcheon Division, MC Publishing Co., 175 Rock Road, N.J. 07452.

Examples of some suitable surface active substances that are useful in this invention especially when the solid or the premix comprises a pharmaceutical agent include: (a) natural surfactants such as casein, gelatin, tragacanth, waxes, enteric resins, paraffin, acacia, gelatin, cholesterol esters, triglycerides, lecithins, and phospholipids (b) nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylammonium bromide, chitosans and lauryldimethylbenzylammonium chloride, (e) colloidal clays such as bentonite and veegum. A detailed description of these surfactants may be found in Remington's Pharmaceutical Sciences, and Theory and Practice of Industrial Pharmacy, Lachman et al, 1986.

More specifically, examples of suitable surface active substances include one or combinations of the following: polaxomers, such as Pluronic™ F68, F108 and F127, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylene-diamine available from BASF, Triton™ X-200, which is an alkyl aryl polyether sulfonate, available from Rohm and Haas. Tween 20, 40, 60 and 80, which are polyoxyethylene sorbitan fatty acid esters, available from ICI Speciality Chemicals, Carbowax™ 3550 and 934, which are polyethylene glycols available from Union Carbide, hydroxy propylmethylcellulose, dimyristoyl phosphatidylglycerol sodium salt, sodium dodecylsulfate, sodium deoxycholate, cetyltrimethylammonium bromide, and one or more phospholipids.

Preferred surface active substances are phospholipid surface active substances and mixtures comprising phospholipid surface active substances. Suitable phospholipids include animal and plant phospholipids; egg phospholipids; soya bean phospholipids; corn phospholipids; wheat germ, flax, cotton, and sunflower seed phospholipids; milk fat phospholipids; glycerophospholipids; sphingophospholipids; phosphatides; phospholipids containing fatty acid esters including palmitate, stearate, oleate, linoleate, and arachidonate which esters can be mixtures and mixtures of isomers in the phospholipids; phospholipids composed of fatty acids containing one or more than one double bond such as dioleoyl phosphatidyicholine and egg phosphatidyicholine that are not stable as powders but are hygroscopic and can absorb moisture and become gummy; phospholipids composed of saturated fatty acids that are stable as powders and are less amenable to absorption of moisture; phosphatidylserines; phosphatidyicholines; phosphatidylethanolamines; phosphatidylinositols; phosphatidylglycerols such as dimyristoyl phosphatidylglycerol, L-alpha-dimyristoyl phosphatidylglycerol also known as 1,2-dimyristoyl-sn-glycero-3-phospho(rac-1-glycerol) and also known as DMPG; phosphatidic acid; hydrogenated natural phospholipids; and commercially available phospholipids such as those available from Avanti Polar Lipids, Inc. of Alabaster, Ala., USA. In the absence of an internal counterion in the phospholipid, a preferred counterion is a monovalent cation such as sodium ion. The phospholipid may be salted or desalted, hydrogenated, partially hydrogenated, or unsaturated, natural, synthetic, or semisynthetic.

Preferred phospholipids include Lipoid E80, Lipoid EPC, Lipoid SPC, DMPG, Phospholipon 100H a hydrogenated soybean phosphatidylcholine, Phospholipon 90H, Lipoid SPC-3, and a mixture thereof. A currently most preferred phospholipid is Lipoid E80.

The concentration of surface active substance that can be added to the solid substrate to be milled or in a premix of solid substrate to be milled according to this invention can be present in the range of 0.1 to 50%, preferably 0.2 to 20%, and more preferably 0.5 to 10%.

The total concentration of one or of more than one surface active substance that can be added to the formulations prepared according to this invention can be in the range of 0.01 to 50%, preferably 0.1 to 50%, preferably 0.2 to 20%, and more preferably 0.5 to 10%.

By small particles of a milled solid is meant particles of solid contained in the premix that have been milled to a desired size equal to or less than a size Sp. Although desired sizes can have a broad range and the particles can be relatively large, preferred desired size is in the range of about 0.005 micrometer to 200 micrometers in average diameter (also sometimes identified as volume weighted average size) in which Sp is 200 micrometers, preferably in the range of 0.01 to 50 micrometers in which Sp is 50 micrometers, more preferably in the range of 0.05 to 20 micrometers in which Sp is 20 micrometers, and most preferably in the range of 0.05 to 5 micrometers in which Sp is 5 micrometers. Depending on the intended use of the product of this invention, small particles of a milled solid can comprise an amorphous or crystalline solid or a mixture of both an amorphous or crystalline solid or a specific crystalline structure such as, for example, an alpha-alumina structure, a graphite structure, an allotropic crystalline structure, and optionally one or more surface active substances. The product of the milling process of this invention comprises a synergetic commixture of small particles of a milled solid together with small particulates of milling media.

As an illustration, by small particles of a poorly water soluble drug is meant particles in the range of about 0.005 micrometer to 20 micrometers in average diameter comprising a poorly water soluble drug in which Sp is 20 micrometers, preferably in the range of 0.01 to 5 micrometers in which Sp is 5 micrometers, more preferably in the range of 0.05 to 3 micrometers in which Sp is 3 micrometers, and most preferably in the range of 0.05 to 1 micrometer in which Sp is 1 micrometers. Small particles of a solid drug can comprise the drug as an amorphous or crystalline solid and optionally one or more biocompatible surface active substance. Very small particles and particulates can be smaller than 500 nanometers in which Sp is 500 nanometers, preferably smaller than 400 nanometers in which Sp is 400 nanometers, more preferably smaller than 300 nanometers in which Sp is 300 nanometers, and most preferably smaller than 200 nanometers in which Sp is 200 nanometers. Particles and particulates in the range from about 5 nanometers to about 100 to 200 nanometers are considered to be in this range in which Sp is 200 nanometers. In this invention, all particles and particulates can be smaller than a desired size Sp. For example, particles and particulates in the range from about 5 nanometers to about 100 nanometers can be obtained from the process of this invention and the desired size can be less than Sp=200 nanometers.

The invention may be applied to a very wide variety of solids which may be slurried with a wide range of liquids. Solids which may be milled include pharmaceutical agents such as drugs and diagnostic imaging contrast agents, iron oxide, talc, silica and other minerals like chalk, zinc oxide, boric oxide, borax, zinc borate, pigments, carbon black, various metals, solid organic compounds, e.g. terephthalic acid, and mixtures thereof, as well as solids previously mentioned. The liquid may be chosen from water, volatile non-aqueous liquids such as hydrocarbons, tetrahydrofuran, dioxan, alcohols and esters, and non-volatile solvents such as phthalates, polyvinylchloride plastisols and waxes, and other solvents previously mentioned. Non-volatile liquids may be used when the slurry is to be used subsequently in liquid form, without drying, for example as plastisols or in certain pharmaceutical preparations. The slurry may include one or more additives to aid milling or to assist later processing such as for example a dispersant or surface active substance, such as a phospholipid which forms a coating on the particles.

The premix preferably ranges from 1 to 70 weight percent of the substrate to be milled. The ratio of fluid carrier to substrate to be milled preferably ranges from less than about 0.01 to about 10. Substrates to be milled are generally solid, and in one aspect are preferably crystalline.

In one embodiment, the premix can comprise a solid to be milled and optionally one or more surface active substances. The milling process of this invention provides a composition comprising small particles of milled solid of desired size as a synergetic commixture with small particulates of milling media bodies of a first material of desired size.

In another embodiment, the premix can comprise a first solid to be milled and a second solid to be milled and optionally one or more surface active substances. The milling process provides a composition comprising a synergetic commixture of small particles of desired size of the first milled solid, optionally small particles of desired size of the second milled solid, and small particulates of desired size of milling media bodies of a first material.

In one aspect of this invention, the process can be used to prepare abrasive grain. Certain embodiments of abrasive grain that contain silica are known to possess improved hardness and/or toughness compared to conventional abrasive grain that do not contain silica. Abrasive grain has been employed in abrasive products for centuries. These abrasive products include bonded abrasives such as grinding wheels, coated abrasives such as sandpapers, and nonwoven abrasives such as cutting wires. Preferred aggressive abrasive grain is typically tough, hard, and chemically resistant to the workpiece being abraded. Tough abrasive grain is generally strong and fracture resistant. Hard abrasive grain generally does not yield or dull from the forces of grinding. If the abrasive grain does yield or dull, this typically leads to decreased abrading performance.

One common type of aggressive abrasive grain is fused alumina. Fused alumina can be formed by heating a source of aluminum oxide to a molten state, rapidly cooling, and then crushing. This type of abrasive grain is hard, tough, and chemically resistant. A more recently developed type of abrasive grain is often referred to as alpha alumina-based ceramic abrasive grain. This type of abrasive grain can be made by a sol-gel process, wherein, for example, a dispersion comprising a liquid medium such as water, alpha alumina monohydrate, often in the presence of a peptizing agent such as nitric acid, and optionally in the presence of additive metal oxide precursors such as magnesium nitrate, is dried, crushed, calcined, and then sintered. The resultant ceramic abrasive grain can be tougher than fused alumina abrasive grain, and can exhibit superior performance in abrading operations. Fused alumina abrasive grain can be prepared according to this invention by milling alumina in the presence of a milling media bodies of a first material comprising alpha alumina and a milling media bodies of a second material selected from the tables herein that will spall the first material. The synergetic commixture of alumina and alpha alumina can be fused to form fused alumina that is mostly or all alpha alumina. Milling media particulates can catalyze the formation of alpha alumina in the fusing step. Alpha alumina comprises a preferred crystal structure.

In one aspect metal oxides such as, for example, MgO should not be present in alpha alumina-based ceramic abrasive grain above levels that result from minor contaminants in precursor materials used in their preparation such as boehmite, iron oxide, and silica. Such levels are preferably about 0.01–25 wt-%, more preferably about 0.01–10 wt-%, and most preferably, about 0.01–1.0 wt-%. Preferred embodiments of the abrasive grain are essentially free of metal oxides. Certain sources of these metal oxides such as soluble salts including nitrate salts can migrate during drying to give a compositionally heterogeneous abrasive grain. Although some of these metal oxides, such as MgO, can increase the amount of the transgranular fracture of the resultant abrasive grain, they also may cause a decrease in the hardness and toughness of the abrasive grain. Silica, however, when used in combination with $Fe_2O_3$ and prepared according to the present invention using milling media bodies of these materials, can increase the amount of transgranular fracture of the resulting abrasive grain. Furthermore hardness, toughness, and grinding performance of abrasive grain prepared according to this invention can be retained and even improved.

Alpha alumina-based ceramic abrasive grain prepared according to the present invention from alumina, milling media bodies of alpha alumina, and a harder and tougher milling media bodies selected from Tables 1, 2, 3, or 4 such as tungsten carbide milling media, can have a density of at least about 3.5 $g/cm^3$, more preferably, at least about 3.7 $g/cm^3$, and most preferably, at least about 3.8 $g/cm^3$. In general, the abrasive grain can be essentially resistant to deformation (i.e, hard) and essentially resistant to fracture (i.e., tough). Abrasive grain prepared according to this invention can have an average hardness (i.e., resistance to deformation) of at least about 16 GPa. Preferably, the average hardness is at least about 18 GPa, more preferably at least about 20 GPa, and most preferably at least about 22 GPa. In another aspect, sintered abrasive grain typically has an average toughness (i.e., resistance to fracture) of at least about 2.5 $MPa/m^{1/2}$. Preferably, the average toughness is at least about 3.0 $MPa/m^{1/2}$, more preferably at least about 3.5 $MPa/m^{1/2}$, and most preferably at least about 4.0 $MPa/m^{1/2}$. A particularly preferred abrasive grain has an average hardness of at least 23 GPa and an average toughness of at least 3.3 $MPa/m^{1/2}$.

Abrasive grains which have little or no glassy phases exhibit transgranular fracture, as opposed to intergranular fracture, when the abrasive grain has been sintered to a real density of at least 90% of theoretical. A very porous abrasive grain (e.g., one having continuous porosity wherein the internal and external pores are connected such as is found in materials having a vennicular or porous non-seeded microstructure) will have a very high "apparent" density and a very high (e.g., greater than about 70%) amount of transgranular fracture. In this case, the amount of transgranular fracture is meaningless as porous material tends to fracture in a transgranular manner. Abrasive grain according to the present invention has a seeded and dense microstructure with very few pores, both external and internal. For such nonporous abrasive grain, a high amount of transgranular fracture can indicate a tougher abrasive grain which will have a generally better grinding performance.

Microhardness can be measured by mounting loose milling media bodies in "EPOMET" mounting resin (from Buehler Ltd., Lake Bluff, Ill.) to form a cylinder containing media measuring 1 inch (2.5 cm) in diameter and 0.75 inch (1.9 cm) tall. The mounted samples can be polished using an "EPOMET" grinder/polisher (from Buehler Ltd.) using "METADI" diamond slurries (from Buehler Ltd.) to obtain polished cross-sections of the samples. The final polishing step can use a 1 micrometer "METADI" diamond slurry. The hardness measurements can be made using a "Mitutoyo MVK-VL" hardness tester (from Mitutoyo Corp of Tokyo, Japan) fitted with a Vickers indenter using a 500-gram indent load. The hardness measurements can be made according to the guidelines stated in ASTM Test Method E384 Test Methods for Microhardness of Materials (1991), the disclosure of which is incorporated herein by reference. Measurement can be made of hardness values in GPa units as an average of five measurements.

The amount of transgranular fracture in the alpha alumina ceramic abrasive grain can be evaluated by hand crushing a small number of abrasive grain (approximately 10–25) using tungsten carbide lined mortar and pestle (SPEX Catalog No. 3203, SPEX Industries, Edison, N.J.). The crushed abrasive grain can then be secured to an SEM sample stub using conductive carbon paste, conductively coated with Au-Pd using an "Anitech Hummer VI Sputtering System" (Anitech Ltd., Springfield, Va.) and examined under a "JEOL 840A" scanning electron microscope (JEOL USA, Peabody, Mass.) at magnifications greater than 10,000× to identify and photograph the fractured abrasive grain surfaces. Transgranular fracture can be quantified by drawing two diagonal lines each approximately 14.5 cm long from the upper left corner to the lower right corner and from the lower left corner to the upper right corner across an SEM photomicrograph of a fired cross-section of the samples taken at 15,000× magnification. The transgranular fracture can be calculated by measuring the cumulative length of the diagonal line passing through transgranular fracture and dividing it by the length of the diagonal line. The percentage of transgranular fracture is an average of two values obtained for each of the diagonal lines.

Abrasive grain prepared according to this invention can be used in grinding wheels, sandpaper, emery, and other abrasive tools. Abrasive media, with the potential exception of the naturally fine powders such as talc, are typically crushed to the particle size required for use. Sizes in use can vary from about 4 grit or about 6 millimeters in diameter, to as fine as about 900 grit or about six microns. Even finer powders can be required when used for the polishing of scratch-free surfaces on high-quality optical lenses and mirrors for high-power telescopes.

Grinding wheels can be made of abrasive grain and a cohesive binder or "bond" that is molded under pressure and often heated to fuse the material to form a wheel. Sandpapers are coated abrasive materials that consist of a layer of abrasive particles held to a flexible backing material by an adhesive binder.

Emery consists primarily of a mixture of the mineral corundum or aluminum oxide and iron oxides such as magnetite ($Fe_3O_4$) or hematite ($Fe_2O_3$), and sometimes contains diaspore, gibbsite, margarite, chloritoid, and sillimanite. A very fine emery dust is used by lens grinders, lapidaries, and plate-glass manufacturers. Emery wheels can be made by mixing powdered emery with a bonding medium such as clay and firing in a kiln. In emery sticks, emery cloth or crocus cloth, and emery paper, powdered emery is bonded to the backing with adhesive.

Abrasive particles can be used in the form of grains or powders. Many particulate materials can be treated by calcining, by washing with acid, or by heating to make them more suitable for use in other applications such as lapping abrasive or as sandblasting grain. For use in lapping and polishing, the abrasive particles can be mixed with a vehicle such as mineral or seal oil. Polishing sticks can consist of waxes or greases impregnated with various-sized abrasive grains. Glass beads can be pressure blasted onto a surface to remove surface-bound substances such as rust, scale, and carbon.

Examples of mills used to accomplish particle size reduction include colloid mills, swinging mills, ball mills, media mills, dispersion mills, attritor mills, jet mills, and vibratory mills. Size reduction methods are described, e.g., in U.S. Pat. Nos. 4,006,025, 4,294,916, 4,294,917, 4,940,654, 4,950,586 and 4,927,744, and UK 1,570,362. Mechanical grinding can occur in a dispersion mill such as a ball mill, an attrition mill, a vibratory mill, and a media mill such as a sand mill or bead mill.

Mills useful for reducing the particle size of a solid substrate can operate in a batch-wise mode or in a continuous or semi-continuous mode. Mills operating in a continuous mode often incorporate a means for retaining relatively large milling media bodies together with relatively large particles of the solid substrate being milled in the milling zone or milling chamber of the mill while allowing smaller particles of the substrate being milled, i.e., product substrate particles as well as small particulates of media that may be produced, to pass out of the milling chamber in either a recirculation or discrete pass mode. Recirculation is often in the form of a dispersion such as a slurry, suspension, dispersion, or colloid of the substrate suspended in a fluid carrier phase that moves from the milling chamber into an often stirred holding vessel and thence back to the milling chamber, frequently with the aid of a pump. The separator or screen is effectively located at the outlet port of the milling chamber. Such means for simultaneous milling and media separation are referred to as "dynamic media separation".

In another method of continuous milling of a substrate, mills operating in a continuous mode can incorporate a means for retaining relatively large particles of the solid substrate being milled in the milling zone or milling chamber of the mill while allowing smaller particles of the substrate being milled, i.e., product substrate particles, as well as the milling media bodies and small particulates of milling media bodies to pass out of the milling chamber in either a recirculation or discrete pass mode. In recirculation mode, the product substrate particles, small media fragments and the media suspended in a fluid carrier move from the milling chamber through the separator or screen into an often stirred holding vessel and thence back to the milling chamber, frequently with the aid of a pump. A suspension of particles and particulates of a desired size $S_p$ can be separated from larger size materials in a subsequent filtration or other step.

In yet another method of continuous milling of a substrate, mills operating in a continuous mode can incorporate a means for retaining both relatively large particles of the solid substrate being milled and large size milling media bodies in the milling chamber of the mill while allowing smaller particles of the substrate being milled, i.e., product substrate particles, as well as small size milling media bodies and small milling media fragments to pass out of the milling chamber in either a recirculation or discrete pass mode. In recirculation mode, the product substrate particles, the small size media, and small media fragments suspended in a fluid carrier move from the milling chamber through the separator or screen into an often stirred holding vessel and thence back to the milling chamber, frequently with the aid of a pump. A suspension comprising particles and particulates of sizes less than $S_p$ can be subsequently isolated, for example by a filtration step and optionally dried.

In a preferred embodiment, the milling process is a continuous process. A dispersion of a synergetic commixture of ground particles of a solid substrate and particulates of milling media bodies that are ground and spalled small enough to pass through a separator or exit filter in a media mill can be recirculated through the milling chamber as a dispersion in a fluid carrier. Examples of suitable means to effect such recirculation include conventional pumps such as peristaltic pumps, diaphragm pumps, piston pumps, centrifugal pumps and other positive displacement pumps. Optionally, during the recirculation of the fluid carrier dispersion of the synergetic commixture of ground particles of solid substrate and particulates of milling media, the commixture or a portion of the commixture can be isolated or the dispersion can be concentrated to provide the commixture for isolation as desired.

Milling can take place in the milling chamber of any suitable media milling apparatus. Suitable mills include high energy media mills which are preferred when one of the grinding media is a polymeric resin. The media mill can contain a rotating shaft. The invention can also be practiced in conjunction with high speed dispersers such as a Cowles disperser, rotor-stator mixers, or other conventional mixers which can deliver high fluid carrier velocity and high shear.

Preferred vessel geometries include diameter to depth ratios of about 1:1 to 1:10. Vessel volumes may range from less than 1 cc to over 4000 liters. A vessel cover may be used to prevent contamination in the milling chamber and/or allow for pressurization or vacuum. It is preferred that jacketed vessels be used to allow temperature control during milling. Processing temperatures may span the range between the freezing and boiling temperatures of the liquid vehicle used to suspend the particles. Higher pressures may be used to prevent boiling. Common agitator designs may include axial or radial flow impellers, pegs, discs, high-speed dispersers, etc. Mixers employing radial flow are preferred because they provide high media velocity and shear with minimal pumping action which may be detrimental to milling performance. Mixer type and mixer speeds are generally and typically employed according to the manufacturer's recommendations. Mixer speeds of I to 50 m/sec may be used, although speeds of 20 to 40 m/sec are often preferred in simple vessel designs. Milling times may range from about 1 hour to 100 hours or more in such high speed mixing mills, depending on desired particle size, formulations, equipment and processing conditions.

In a batch process, the milling media, the fluid carrier, and the premix comprising substrate being milled remain in the vessel until the fractured substrate particles and milling media particulates have been reduced to the desired size or to a minimum size achievable. Small media fragments can be produced from media that is less tough and more brittle than harder, tougher, and less brittle media. The fluid carrier, the product substrate particles, and small particulates of media are then separated from the media particles with a separator or screen at the outlet port of the milling chamber or separated in a subsequent size separation or filtration step.

Various techniques have been established for retaining media in media mills, including use of separating devices such as a media separators including rotating gap separators, screens, sieves, centrifugally-assisted screens, and similar devices to physically restrict passage of media from the mill. Retention of media arises because the dimensions of the milling media bodies are larger than the dimensions of the openings through which the reduced size substrate particles can pass. Unmilled or partially milled solid substrate with particle size at or above the media size are also retained until reduced in size to small product particles.

In batch processes employing ball mills (e.g. Abbe Ball Mills) or stirred ball mills (e.g. Union Process Attritor) separation of dispersion and milling media bodies is performed after milling is complete, usually through a screen or sieve or filter sized smaller than the milling media. Typically, the screen is affixed to the milling vessel and slurry is removed by gravity drainage or pumped out of the vessel to pass through the filter. Alternatively, the slurry may be forced from the vessel by charging the vessel with compressed gas. However, the use of relatively large size milling media bodies can impose a practical limitation to the final size of the substrate particles produced in the milling process. The desired particle size and particulate size is often about $\frac{1}{1000}^{th}$ the size of the media used to mill the solid to the particle size.

The premix of solid substrate can optionally comprise one or more surface active substance. Surface active substances are known to provide stability to small particles prepared in milling and other size reduction processes.

In a preferred aspect, the solid substrate in the starting premix can comprise a pharmaceutical substance such as a therapeutic or diagnostic agent. When the solid substrate is ground or reduced in size sufficiently to a desired size such as less than 2 micrometers, preferably less than 1 micrometer, and most preferably less than 500 micrometers, and when the milling bodies of the first material have been spalled to form particulates of milling media bodies less than or equal to the desired size, the commixture of product substrate particles and particulates of milling media bodies can be removed from the milling chamber as a dispersion in the fluid carrier. The dispersion can be passed through a suitable separator device such as a filter to remove residual milling media bodies larger than the desired size as well as residual unmilled or partially milled substrate that is too large to pass through the filter. The dispersion of the synergetic commixture of solid product substrate particles and particulates of milling media bodies equal to or less than a desired size are not retained by a filter that permits passage of particles and particulates of a desired size while residual media and residual unmilled or residual partially milled solid substrate particles larger than the desired size are retained by the filter. A suitable filter or separator device useful in a method of separation can be a separator device at the exit port in a media mill or a filter such as a depth filter, a mesh, a screen, a sieve, a milk filter, a bed of particles, and the like.

In one embodiment, the desired size of a synergetic commixture of milled solid substrate particles and particulates of milling media bodies is submicrometer or nanoparticulate size, e.g., less than about 500 nm. Commixtures having an average particle and particulate size of less than 100 nm can be prepared in accordance with the present invention. In preferred embodiments, a synergetic commixture of a therapeutic or diagnostic agent and particulates of milling media bodies that can serve as an excipient or filler in a drug formulation can be prepared in submicrometer or nanoparticulate particle size, e.g., less than about 500 nm. Particles and particulates of the synergetic commixture can be prepared having an average particle size of less than about 300 nm. In certain embodiments, particles and particulates of the synergetic commixture having an average particle size of less than 100 nm can be prepared in accordance with the present invention.

Preferred proportions of the grinding media, solid substrate, fluid carrier, and one or more surface active substance, milling media bodies of a first material, and milling media bodies of a second material present in the milling chamber of a media mill can vary within wide limits and depend, for example, upon the particular substrate such as the kind of solid selected in the premix which in preferred embodiments is a therapeutic or diagnostic agent, and the sizes and densities of the grinding media. Preferred milling media concentrations depend upon the application and can be optimized based on milling performance requirements, and the flow characteristics of the substrate to be milled. Total grinding media concentrations can range from about 10–95%, preferably 20–90% by volume depending on the application and can be optimized based on the above factors, milling performance requirements, and the flow characteristics of the combined grinding media and substrate dispersion. In high energy media mills, it can be desirable to fill 70–90% of the volume of the grinding chamber with grinding media. The ratio of milling media bodies of a first material to milling media bodies of a second material can range from about 1:1000 to about 1000:1, preferably 1:100 to about 100:1, and most preferably from 1:3 to about 10:1.

When two or more size distributions of spherical milling media bodies are used in this invention, for example large size media of a first material and small size media of a second material or large and small size media of a first material and/or large and small size media of a second material, preferably between approximately 30 to 100 percent of the slurry of the premix of solid substrate to be milled resides in the interstitial voids between adjacent media P beads. Where the void volume of randomly-packed spheres is approximated to be about 40 percent, the corresponding preferred volume ratio of small milling media bodies to premix slurry in the milling vessel ranges from 0.5 to 1.6. It is preferred that between 60 to 90 percent of slurry reside in small media voids to maximize milling efficiency. The uniformity of the voids is, of course, distorted by the presence of large and small milling media bodies in the milling chamber. The size of the milling media bodies selected is a function of the desired size of the particles and particulates, and vice versa, the ratio of desired size of particles to the size of the milling media bodies being approximately 1/1000.

In a preferred aspect, the present invention provides an improved process for the preparation of a synergetic commixture comprising small particles of a poorly water soluble drug and small particulates of milling media bodies of a first material. In particular the present invention provides an improved process for the preparation of a synergetic commixture comprising small particles of a poorly water soluble drug and small particulates of milling media bodies of a first material as a dispersion in an aqueous carrier. Furthermore, the present invention provides an improved process for the preparation of a synergetic commixture comprising small particles of a poorly water soluble drug and small particulates of milling media bodies of a first material as a dried synergetic commixture of said small particles of a poorly water soluble drug and said small particulates of milling media bodies of a first material.

As used herein, "small particle" refers to a particle or a distribution of particles having a diameter or an average diameter, respectively, of from nanometers to micrometers. Small particles are microparticles, as used herein, and also refer to solid particles of irregular, non-spherical or spherical shapes.

Formulations containing these synergetic commixtures provide some specific advantages over unformulated non-milled drug particles. These advantages include improved uniformity of dispersed ingredients, improved oral bioavailability of drugs that are poorly absorbed from the GI tract, development of injectable formulations that are currently available only in oral dosage form when all components of the formulation are biocompatible or biodegradable, sustained or delayed release of tableted and encapsulated drug formulations, and preparation of inhaled and ophthalmic formulations of drugs that otherwise could not be formulated for nasal or ocular use.

Water insoluble and poorly water soluble compounds are those having poor solubility in water at or below normal physiological temperatures, that is <5 mg/ml at physiological pH (6.5–7.4). Preferably their water solubility is <1 mg/ml, and more preferably <0.1 mg/ml.

It is desirable that when the solid in the synergetic commixture is a drug or pharmaceutical agent, it should be stable in water as a dispersion. Otherwise or in addition a dried form such as a lyophilized or spray-dried or evaporated or other dry form of synergetic commixture form may be desirable for example for use in formation of drug delivery compositions including capsules, tablets, and formulations with additional excipients and drugs.

In one embodiment, the invention can be practiced with a wide variety of pharmaceutical substrates including therapeutic and diagnostic agents. Examples of some preferred water-insoluble drugs include immunosuppressive and immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antiarrhythmics, antihypertensive agents, antineoplastic agents, hormones, and nutrients. A detailed description of these and other suitable drugs may be found in Remington's Pharmaceutical Sciences, 18th edition, 1990, Mack Publishing Co. Philadelphia, Pa. which is hereby incorporated by reference.

Suitable compounds can have pharmaceutical efficacy in a number of therapeutic an diagnostic imaging areas. Non-limiting classes of compounds and agents from which a poorly water soluble drug that is useful in this invention can be selected include an anesthetic agent, an ace inhibiting agent, an antithrombotic agent, an anti-allergic agent, an antibacterial agent, an antibiotic agent, an anticoagulant agent, an anticancer agent, an antidiabetic agent, an antihypertension agent, an antifungal agent, an antihypotensive agent, an antiinflammatory agent, an antimitotic agent, an antimigraine agent, an antiparkinson agent, an antirheumatic agent, an antithrombin, an antiviral agent, a beta blocking agent, a bronchospasmolytic agent, a calcium antagonist, a cardiovascular agent, a cardiac glycosidic agent, a carotenoid, a cephalosporin, a contraceptive agent, a cytostatic agent, a diagnostic imaging agent, a diuretic agent, an enkephalin, a fibrinolytic agent, a growth hormone, an immunosunpressant, an insulin, an interferon, a lactation inhibiting agent, a lipid-lowering agent, a lymphokine, a neurologic agent, a prostacyclin, a prostaglandin, a psychopharmaceutical agent, a protease inhibitor, a magnetic resonance diagnostic imaging agent, a reproductive control hormone, a sedative agent, a sex hormone, a somatostatin, a steroid hormonal agent, a vaccine, a vasodilating agent, and a vitamin. While a single solid pharmaceutical agent is most frequently incurred in the process of this invention, the use of a mixture of two or more solid pharmaceutical agents in the process of this invention is contemplated. The mixture of more than one agent can be a mixture of solid pharmaceutical agents such as two solid antifungal agents that are insoluble in the fluid carrier or a mixture of a fibrate such as fenofibrate and a statin that is poorly soluble in an aqueous fluid carrier. Alternatively, the mixture can be a mixture of a solid agent that is insoluble or poorly soluble in the fluid carrier (for example, a fibrate such as fenofibrate that is poorly soluble in an aqueous fluid carrier) together with a solid agent that is soluble in the fluid carrier (for example such as a statin that is soluble in an aqueous fluid carrier). The product of a process of this invention employing fenofibrate and a statin can be formulated into an oral dosage form such as a tablet or capsule or freeze dried wafer and can be used for the treatment of hyperlipidemia and conditions related to abnormal or unhealthy elevated lipid concentrations in the blood.

Non-limiting examples of representative poorly soluble drugs useful in this invention include albendazole, albendazole sulfoxide, alfaxalone, acetyl digoxin, acyclovir analogs, alprostadil, aminofostin, anipamil, antithrombin III, atenolol, azidothymidine, beclobrate, beclomethasone, belomycin, benzocaine and derivatives, beta carotene, beta endorphin, beta interferon, bezafibrate, binovum, biperiden, bromazepam, bromocryptine, bucindolol, buflomedil, bupivacaine, busulfan, cadralazine, camptothesin, canthaxanthin, captopril, carbamazepine, carboprost, cefalexin, cefalotin, cefamandole, cefazedone, cefluoroxime, cefinenoxime, cefoperazone, cefotaxime, cefoxitin, cefsulodin, ceftizoxime, chlorambucil, chromoglycinic acid, ciclonicate, ciglitazone, clonidine, cortexolone, corticosterone, cortisol, cortisone, cyclophosphamide, cyclosporin A and other cyclosporins, cytarabine, desocryptin, desogestrel, dexamethasone esters such as the acetate, dezocine, diazepam, diclofenac, dideoxyadenosine, dideoxyinosine, digitoxin, digoxin, dihydroergotamine, dihydroergotoxin, diltiazem, dopamine antagonists, doxorubicin, econazole, endralazine, enkephalin, enalapril, epoprostenol, estradiol, estramustine, etofibrate, etoposide, factor ix, factor viii, felbamate, fenbendazole, fenofibrate, flunarizin, flurbiprofen, 5-fluorouracil, flurazepam, fosfomycin, fosmidomycin, furosemide, gallopamil, gamma interferon, gentamicin, gepefrine, gliclazide, glipizide, griseofulvin, haptoglobulin, hepatitis B vaccine, hydralazine, hydrochlorothiazide, hydrocortisone, ibuprofen, ibuproxam, indinavir, indomethacin, iodinated aromatic x-ray contrast agents such as iodamide, ipratropium bromide, ketoconazole, ketoprofen, ketotifen, ketotifen fumarate, K-strophanthin, labetalol, lactobacillus vaccine, lidocaine, lidoflazin, lisuride, lisuride hydrogen maleate, lorazepam, lovastatin, mefenamic acid, melphalan, memantin, mesulergin, metergoline, methotrexate, methyl digoxin, methylprednisolone, metronidazole, metisoprenol, metipranolol, metkephamide, metolazone, metoprolol, metoprolol tartrate, miconazole, miconazole nitrate, minoxidil, misonidazol, molsidomin, nadolol, nafiverine, nafazatrom, naproxen, natural insulins, nesapidil, nicardipine, nicorandil, nifedipine, niludipin, nimodipine, nitrazepam, nitrendipine, nitrocamptothesin, 9-nitrocamptothesin, oxazepam, oxprenolol, oxytetracycline, penicillins such as penicillin G benethamine, penecillin O, phenylbutazone, picotamide, pindolol, piposulfan, piretanide, piribedil, piroxicam, pirprofen, plasminogenici activator, prednisolone, prednisone, pregnenolone, procarbacin, procaterol, progesterone, proinsulin, propafenone, propanolol, propentofyllin, propofol, propranolol, rifapentin, simvastatin, semi-synthetic insulins, sobrerol, somastotine and its derivatives, somatropin, stilamine, sulfinalol hydrochloride, sulfinpyrazone, suloctidil, suprofen, sulproston, synthetic insulins, talinolol, taxol, taxotere, testosterone, testosterone propionate, testosterone undecanoate, tetracane HI, tiaramide HCl, tolmetin, tranilast, triquilar, tromantadine HCl, urokinase, valium, verapamil, vidarabine, vidarabine phosphate sodium salt, vinblastine, vinburin, vincamine, vincristine, vindesine, vinpocetine, vitamin A, vitamin E succinate, and x-ray contrast agents. Drugs can be neutral species or basic or acidic as well as salts such as exist in the presence of an aqueous buffer.

Non-limiting examples of representative poorly soluble drugs useful in this invention also include acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, dipyridamole, dolasetron, enalapril maleate, enalaprilat, famotidine, felodipine, furazolidone, irbesartan, lansoprazole, loratadine, loxapine, mebendazole, mercaptopurine, milrinone lactate, minocycline, mitoxantrone, nelfinavir mesylate, norfioxacin, olanzapine, omeprazole, penciclovir, pimozide, tacolimus, quazepam, raloxifene, rifabutin, rifampin, risperidone, rizatriptan, saquinavir, sertraline, sildenafil, acetyl-sulfisoxazole, temazepam, thiabendazole, thioguanine, trandolapril, triamterene, trimetrexate, troglitazone, trovafloxacin, vinblastine sulfate, mycophenolate, atovaquone, proguanil, ceftazidime, cefuroxime, terbinafine, thalidomide, fluconazole, amsacrine, dacarbazine, teniposide, and acetylsalicylate.

Suitable pharmaceutical agents as solids in this invention include diagnostic imaging agents such as X-ray contrast agents, magnetic resonance imaging (MRI) contrast agents, light imaging contrast agents, and photoacoustic imaging agents. Useful X-ray contrast agents are, for example, iodinated aromatic acid derivatives such as ethyl-3,5-bisacetoamido-2,4,6-triiodobenzoate, ethyl(3,5-bis(acetylamino)-2,4,6-triodobenzoyloxy) acetate, ethyl-2-(bis(acetylamino)-2,4,6-triodobenzoyloxy)butyrate, 6-ethoxy-6-oxohexyl-3,5-bis(acetylamino)-2,4,6-triiodobenzoate. Useful MRI contrast agents include iron oxide particles. Useful light imaging contrast agents include dyes and pigments including poorly water soluble dyes such as indocyanine green, infrared absorbing dyes, infrared emitting dyes such as infrared laser dyes, fluorescent dyes, and dyes that absorb and/or emit visible light. Dyes that absorb light and convert light to heat are useful as photoacoustic imaging contrast agents.

In a preferred aspect, the present invention provides a process for preparing a synergetic commixture comprising small particles of a solid poorly water soluble pharmaceutical compound and small particulates of a first material of a desired size in a fluid carrier optionally in the presence of a surface active substance, said process comprising the steps of:

(a) providing to the milling chamber of a media mill a contents comprising a pre-mix of a solid poorly water soluble pharmaceutical compound, a fluid carrier, a plurality of milling bodies of a first material, and a plurality of milling bodies of a second material;

(b) operating said media mill to grind said solid substrate and degrade at least a portion of said milling bodies of first material to produce a dispersion in said fluid carrier comprising a synergetic commixture of small particulates of said first material and small particles of said solid poorly water soluble pharmaceutical compound having a desired size equal to or less than a size Sp;

(c) separating said dispersion from any residual milling body, piece of milling body, and solid poorly water soluble pharmaceutical compound having a size larger than $S_p$; and (d) optionally removing said fluid carrier from said dispersion to form a dry synergetic commixture comprising said particles and said small particulates;

wherein the milling bodies of said first material are fractured and eroded by the milling bodies of said second material, the milling bodies of said second material are essentially resistant to fracture and erosion in the milling process, and Sp is smaller than the size of the milling media bodies of the second material.

In another embodiment of this invention, we have discovered a process for preparing a synergetic commixture comprising small particles of a solid poorly water soluble pharmaceutical compound and small particulates of a first material of a desired size, said process comprising the steps of:

(a) providing to the milling chamber of a media mill a contents comprising a pre-mix of a solid poorly water soluble pharmaceutical compound, a fluid carrier, a plurality of milling bodies of a first material having a fracture toughness $K_{C1}$, and a plurality of milling bodies of a second material having a fracture toughness $K_{C2}$;

(b) operating said media mill to grind said solid substrate and degrade at least a portion of said milling bodies of first material to produce a dispersion in said fluid carrier comprising a synergetic commixture of small particulates of said first material and small particles of said solid poorly water soluble pharmaceutical compound having a desired size equal to or less than a size Sp;

(c) separating said dispersion from any residual milling body, piece of milling body, and solid poorly water soluble pharmaceutical compound having a size larger than $S_p$; and (d) optionally removing said fluid carrier from said dispersion to form a synergetic commixture free of fluid and comprising said particles and said small particulates; wherein $K_{C2}$ is greater than $K_{C1}$.

In another embodiment of this invention, the milling media bodies can comprise a mixture of media of a first material having a fracture toughness $K_{C1}$ and milling media bodies of a second material having a fracture toughness $K_{C2}$ wherein $K_{C1}$ is less than $K_{C2}$ and the size of the media of the first material is larger than the size of the media of the second material.

In yet another embodiment of this invention, the milling media bodies can comprise a mixture of milling media bodies of a first material having a fracture toughness $K_{C1}$ and milling media bodies of a second material having a fracture toughness $K_{C2}$ wherein $K_{C2}$ is greater than $K_{C1}$ and the size of the media of the first material is smaller than the size of the milling media bodies of the second material.

In yet another embodiment of this invention, the milling media bodies can comprise a mixture of media of a first material having a fracture toughness $K_{C1}$ and media of a second material having a fracture toughness $K_{C2}$ wherein $K_{C2}$ is greater than $K_{C1}$ and the size of the media of the first material is the same as the size of the media of the second material.

In yet another embodiment of this invention, the milling media bodies can comprise a mixture of media of a first material having a brittleness index $B_{1L}$ and a second material having a brittleness index $B_{2L}$, wherein $B_{1L}$ is less than $B_{2L}$, and $B_{1L}$ and $B_{2L}$ are less than about 5.5.

In yet another embodiment of this invention, the milling media bodies can comprise a mixture of media of a first material having a brittleness index $B_{1H}$ and a second material having a brittleness index $B_{2H}$, wherein $B_{1H}$ is greater than $B_{2H}$ and both $B_{1H}$ and $B_{2H}$ are greater than about 5.5.

In yet another embodiment of this invention, the milling media bodies can comprise a mixture of media of a first material having a hardness $H_1$ and a second material having a hardness $H_2$, wherein $H_1$ is less than $H_2$.

In another preferred aspect, the present invention provides a process for preparing a synergetic commixture comprising small particles of a solid poorly water soluble pharmaceutical compound and small particulates of a first material of a desired size in a fluid carrier optionally in the presence of a surface active substance, said process comprising the steps of:

a) providing to the milling chamber of a media mill a contents comprising a pre-mix of a solid poorly water soluble pharmaceutical compound, a fluid carrier, a plurality of milling bodies of a first material having a fracture toughness $K_{C1}$, and a plurality of milling bodies of a second material having a fracture toughness $K_{C2}$;

b) operating said media mill to grind said solid substrate and degrade at least a portion of said milling bodies of first material to produce a dispersion in said fluid carrier comprising a synergetic commixture of small particulates of said first material and small particles of said solid substrate having a desired average size equal to or less than a size Sp; and c) separating said dispersion from any milling bodies and particles of the solid poorly water soluble pharmaceutical compound having a size larger than $S_p$;

wherein $K_{C2}$ is larger than $K_{C1}$.

In another preferred aspect, the present invention provides a process for preparing a synergetic commixture comprising small particles of a solid poorly water soluble pharmaceutical compound and small particulates of a first material of a desired size optionally in the presence of a surface active substance, said process comprising the steps of:

a) providing to the milling chamber of a media mill a contents comprising a pre-mix of a solid poorly water soluble pharmaceutical compound, a fluid carrier, a plurality of milling bodies of a first material having a fracture toughness $K_{C1}$, and a plurality of milling bodies of a second material having a fracture toughness $K_{C2}$;

b) operating said media mill to grind said solid substrate and degrade at least a portion of said milling bodies of first material to produce a dispersion in said fluid carrier comprising a synergetic commixture of small particulates of said first material and small particles of said solid poorly water soluble pharmaceutical compound having a desired average size equal to or less than a size Sp;

c) separating said dispersion from any milling bodies and particles of the solid poorly water soluble pharmaceutical compound having a size larger than $S_p$; and d) removing said fluid carrier from said dispersion to form a synergetic commixture free of fluid and comprising said particles and said small particulates, wherein $K_{C2}$ is larger than $K_{C1}$.

Small media can range in size from about 0.005 to 3 mm. For fine grinding, small media particles preferably are from 0.005 to 0.5 mm, more preferably, 0.005 to 0.3 mm in size.

Depending on the intended use and on the solid and milling material in the commixture, particles of milled solid and particulates of milling media bodies prepared according to this invention as a synergetic commixture can have particle and particulate size of less than 2 micrometers, preferably less than 1 micrometer, more preferably less than 0.5 micrometer. In some aspects the preferred size of the particles and particulates is more preferably less than 0.4 micrometer, yet more preferably less than 0.3 micrometer, yet more preferably less than 0.2 micrometer, and yet more preferably less than 0.1 micrometer. In still other aspects, the preferred size of the particles and particulates is more preferably less than 0.05 micrometer, and most preferably less than 0.01 micrometers.

A pharmaceutical composition prepared according to this invention as synergetic commixture of small particles of a pharmaceutical agent and small particulates of milling media bodies of a first material can be further formulated for example by mixing with one or more pharmaceutically acceptable carrier such as one or more excipients and binding agents and converted into dosage forms such as a tablet or ointment and the like suitable for administering to a mammal such as man according to methods known in the art for the treatment of a disease or for a diagnostic procedure. Doasage forms can include pharmaceutical pastes such as those containing calcium carbonate, talc, zinc oxide and other fine solid materials; controlled release agents; timed release agents; matrix release agents; patches; transdermal adhesive materials; diagnostic agents; tablets; pills; creams; ointments; suppositories; pessaries; powders; pastes; jellies; capsules; granules; cachets; lozenges; and pastilles.

Methods of administration can include oral administration, topical administration, implantation, and injection into a body undergoing treatment or diagnosis.

The milling compositions and processes of this invention are further described by the following non-limiting examples.

EXAMPLE 1

A Perl Mill PML-H/V media mill with a 0.8 liter grinding vessel or milling chamber is configured with four perforated polyurethane discs, a screen gap of 0.3 mm and 10 gaps in the screen. The media mill vessel and milling chamber is purged with nitrogen and charged with 200 grams of 650 micron (0.65 mm) diameter crosslinked poly(styrene-co-divinylbenzene) beads as large size milling media bodies bodies and 50 grams of 100 microns silicon dioxide (Nyacol 9950 from Nyacol Products Inc.) as small size milling media bodies. A stirred tank reservoir cooled with cold water passing through a jacket connected by a peristaltic pump to the milling chamber of the media mill is charged with a premix of 2 kilograms of water as a fluid carrier, 260 grams of sucrose that is an additional excipient that is soluble in the fluid carrier, 78 grams of Lipoid E-80 as a surface active agent (a lecithin or phospholipid material), and 260 grams of solid fenofibrate as a water-insoluble solid drug substance. The premix slurry to be milled is mixed with an agitator and pumped by the peristaltic pump from a stirred holding vessel into the milling vessel and through the milling chamber with a pump flow rate of about 30 kilogram/hour while the media mill is operated to mill the solid fenofibrate to small particles or microparticles with a volume weighted mean diameter of about 0.84 micrometers as a suspension or slurry in the aqueous fluid. The precooled slurry recirculated through the media mill. The size distribution of the product particles in the fluid carrier in the holding tank is smaller than the small sized beads. At the end of milling process the slurry is filtered through the 0.3 mm screen and the fine suspension of the product along with silica particles is harvested. The suspension contains milled fenofibrate particles. No styrenic milling media bodies are found in the product dispersion suspended in the fluid carrier.

EXAMPLE 2

The process of Example 1 is repeated with 0.26 grams of Pluronic™ F68 added to the premix as a second surface active agent. At the end of milling process the slurry is filtered through the 0.3 mm screen and the fine suspension of the product along with silica particles is harvested. The suspension contains milled fenofibrate particles. No styrenic milling media bodies are found in the product dispersion suspended in the fluid carrier.

EXAMPLE 3

The process of Example 2 is repeated using 100 grams of 100 micron cross-linked polyglutaric-polylactate copolymer beads in place of the silicon dioxide (Nyacol 9950 from Nyacol Products Inc.) as small size milling media bodies. At the end of milling process the slurry is filtered through the 0.3 mm screen and the fine suspension of the product along with cross-linked polyglutaric-polylactate copolymer particles are harvested. No styrenic milling media are found in the product dispersion suspended in the fluid carrier.

What is claimed is:

1. A process for preparing a synergetic commixture comprising small particles of a solid substrate and small particulates of a first material of a desired size, said process comprising:
   a) providing to a milling chamber of a media mill a contents comprising a pre-mix of a solid substrate, a fluid carrier, a plurality of milling bodies of a first material, and a plurality of milling bodies of a second material;
   b) operating said media mill to grind said solid substrate and degrade at least a portion of said milling bodies of the first material to produce a dispersion in said fluid carrier comprising a synergetic commixture of small particulates of said first material and small particles of said solid substrate having a desired size equal to or less than a size $S_p$;
   c) separating said dispersion from any residual milling body, piece of milling body, and solid substrate having a size larger than $S_p$; and
   d) optionally removing said fluid carrier from said dispersion to form a dry synergetic commixture comprising said particles and said small particulates; wherein the milling bodies of said first material are fractured and eroded by the milling bodies of said second material, the milling bodies of said second material are essentially resistant to fracture and erosion in the milling process, and $S_p$ is smaller than the size of the milling bodies of the second material.

2. The process of claim 1, wherein the premix comprises one or more than one surface active substance.

3. The process of claim 1, further comprising the addition of one or more than one surface active substance.

4. The process of claim 3, wherein the one or more than one surface active substance is selected from the group consisting of phospholipids, natural surfactants, nonionic surfactants, anionic surfactants, cationic surfactants, and colloidal clays.

5. The process of claim 3, wherein the one or more than one surface active substance is a phospholipid.

6. The process of claim 5, wherein the phospholipid is selected from the group consisting of egg lecithin, egg phosphatidylcholine, soy phosphatidylcholine, dimyristoyl phosphatidylglycerol, hydrogenated egg phosphatidylcholine, hydrogenated soybean phosphatidylcholine, and combinations thereof.

7. The process of claim 1, wherein the solid substrate is selected from the group consisting of a solid pigment, a solid photographic material, a solid cosmetic ingredient, a solid support material, a solid toner material, a solid grinding material, and a solid pharmaceutical agent.

8. The process of claim 1, wherein the solid substrate is a pharmaceutical agent.

9. The process of claim 8, wherein the pharmaceutical agent is a poorly water soluble or water insoluble drug.

10. The process of claim 8, wherein the pharmaceutical agent is selected from the group consisting of an anesthetic agent, an ace inhibiting agent, an antithrombotic agent, an anti-allergic agent, an antibacterial agent, an antibiotic agent, an anticoagulant agent, an anticancer agent, an antidiabetic agent, an antihypertension agent, an antifungal agent, an antihypotensive agent, an antiinflammatory agent, antimitotic agent, an antimigraine agent, an antiparkinson agent, an antirheumatic agent, an antithrombin, an antiviral agent, a beta blocking agent, a bronchospasmolytic agent, a calcium antagonist, a cardiovascular agent, a cardiac glycosidic agent, a carotenoid, a cephalosporin, a contraceptive agent, a cytostatic agent, a diagnostic imaging agent, a diuretic agent, an enkephalin, a fibrinolytic agent, a growth hormone, an immunosuppressant, an insulin, an interferon, a lactation inhibiting agent, a lipid-lowering agent, a lymphokine, a neurologic agent, a prostacyclin, a prostaglandin, a psycho-pharmaceutical agent, a protease inhibitor, a magnetic resonance diagnostic imaging agent, a reproductive control hormone, a sedative agent, a sex hormone, a somatostatin, a steroid hormonal agent, a vaccine, a vasodilating agent, and a vitamin.

11. The process of claim 8, wherein the pharmaceutical agent is selected from the group consisting of fenofibrate, nitrocamptothecin, and cyclosporin.

12. The process of claim 1, wherein the fluid carrier is selected from the group consisting of water, sterile water, water for injection, an aqueous solution of one or more salts, a solution of one or more aqueous buffers, aqueous phosphate buffered saline, sugar-containing water, an aqueous solution of one or more pharmaceutical excipients, an aqueous solution of one or more carbohydrates, an aqueous solution of one or more polymers, an aqueous solution of one or more surface active substance, a liquid surface active substance, ethanol, PEG-containing water, and mixtures of these carriers.

13. The process of claim 1, wherein the fluid carrier is sterile.

14. The process of claim 2, wherein the one or more than one surface active substance is selected from the group consisting of phospholipids, natural surfactants, nonionic surfactants, anionic surfactants, cationic surfactants, and colloidal clays.

15. The process of claim 2, wherein the one or more than one surface active substance is a phospholipid.

16. The process of claim 15, wherein the phospholipid is selected from the group consisting of egg lecithin, egg phosphatidylcholine, soy phosphatidylcholine, dimyristoyl phosphatidylglycerol, hydrogenated egg phosphatidylcholine, hydrogenated soybean phosphatidylcholine, and combinations thereof.

17. The process of claim 1, wherein the fluid carrier is selected from the group consisting of a gas, a liquefied compressed gas, a supercritical fluid, a supercritical fluid containing one or more dissolved excipients, and a supercritical fluid containing one or more surface active substances.

18. The process of claim 1, wherein the process is batchwise.

19. The process of claim 1, wherein the process is continuous.

20. The process of claim 1, wherein the first material is selected from the group consisting of silica, calcium carbonate, marble, magnesium carbonate, zinc carbonate, dolomite, lime, magnesia, barium sulfate, calcium sulfate, aluminum hydroxide, colloidal silica, zinc oxide, iron oxide, titanium oxide, a biodegradable polymer, a biocompatible polymer, a composite of biocompatible polymers, a composite of biodegradable polymers, a polymeric resin, an ion exchange resin, silicon dioxide, and glass bead.

21. The process of claim 1, wherein the portion of the milling bodies of the first material degraded is from 0.01% to 100%.

22. The process of claim 1, wherein the desired particle size $S_p$, is less than 10 micrometers.

23. The process of claim 1, wherein the desired particle size $S_p$, is less than 5 micrometers.

24. The process of claim 1, wherein the desired particle size $S_p$, is less than 2 micrometers.

25. The process of claim 1, wherein desired particle size $S_p$, is less than 1 micrometer.

26. The process of claim 1, wherein desired particle size $S_p$, is less than 500 nanometers.

27. The process of claim 1, wherein the plurality of milling bodies of first material is from 1:1000 to 1000:1 times the plurality of milling bodies of the second material.

28. The process of claim 1, wherein the plurality of milling bodies of first material is from 1:100 to 100:1 times the plurality of milling bodies of the second material.

29. The process of claim 1, wherein the plurality of milling bodies of first material is from 1:10 to 10:1 times the plurality of milling bodies of the second material.

30. The process of claim 1, wherein the media mill is maintained at a temperature below the melting point of the solid substrate.

31. The process of claim 1, wherein the small particles and small particulates are less than 2 micrometers in size.

32. The process of claim 1, wherein the small particles and small particulates are less than 1 micrometer in size.

33. The process of claim 1, wherein the small particles and small particulates are less than 0.5 micrometer in size.

34. The process of claim 1, wherein the small particles and small particulate are less than 0.4 micrometer in size.

35. The process of claim 1, wherein the separation employs a separating device selected from the group consisting of a filter, a separator in the media mill, a separator at an exit port in the media mill, a depth filter, a mesh, a screen, a sieve, a milk filter, and a bed of particles.

36. The process of claim 1, wherein the first material has a fracture toughness $K_{C1}$ and the second material has a fracture toughness $K_{C2}$, wherein $K_{C1}$ is less than $K_{C2}$.

37. The process of claim 36, wherein $K_{C1}$ is less than 1.
38. The process of claim 36, wherein $KC_1$ is less than 1.5.
39. The process of claim 36, wherein $K_{C1}$ is less than 2.
40. The process of claim 36, wherein $K_{C2}$ is at least 1.1 times larger than $K_{C1}$.
41. The process of claim 36, wherein $K_{C2}$ is at least 1.3 times larger than $K_{C1}$.
42. The process of claim 36, wherein $K_{C2}$ is at least 1.5 times larger than $K_{C1}$.
43. The process of claim 1, wherein the first material has a brittleness index $B_{1L}$ and the second material has a brittleness index $B_{2L}$, wherein $B_{1L}$ is less than $B_{2L}$, and $B_{1L}$ and $B_{2L}$ are less than about 5.5.
44. The process of claim 1, wherein the first material has a brittleness index $B_{1H}$ and the second material has a brittleness index $B_{2H}$, wherein $B_{1H}$ is greater than $B_{2H}$ and both $B_{1H}$ and $B_{2H}$ are greater than about 5.5.
45. The process of claim 1, wherein the first material has a hardness $H_1$ and the second material has a hardness $H_2$, wherein $H_1$ is less than $H_2$.
46. The process of claim 1, wherein the milling bodies of the first material comprise an ion exchange resin.
47. The process of claim 1, wherein the milling bodies of the second material comprise an ion exchange resin.

* * * * *